(12) United States Patent
Geneste et al.

(10) Patent No.: US 10,160,744 B2
(45) Date of Patent: Dec. 25, 2018

(54) QUINOLINE COMPOUNDS SUITABLE FOR TREATING DISORDERS THAT RESPOND TO THE MODULATION OF THE SEROTONIN 5-$HT_6$ RECEPTOR

(71) Applicant: Abbvie Deutschland GmbH & Co. KG, Wiesbaden (DE)

(72) Inventors: Hervé Geneste, Ludwigshafen (DE); Andreas Haupt, Ludwigshafen (DE); Frauke Pohlki, Ludwigshafen (DE); Ana Lucia Relo, Ludwigshafen (DE); Liliane Unger, Ludwigshafen (DE); Karsten Wicke, Ludwigshafen (DE)

(73) Assignee: ABBVIE DEUTSCHLAND GMBH & CO. KG, Wiesbaden (DE)

( * ) Notice: Subject to any disclaimer, the term of this patent is extended or adjusted under 35 U.S.C. 154(b) by 0 days.

(21) Appl. No.: 15/458,534

(22) Filed: Mar. 14, 2017

(65) Prior Publication Data

US 2017/0260158 A1 Sep. 14, 2017

Related U.S. Application Data

(60) Provisional application No. 62/307,823, filed on Mar. 14, 2016.

(51) Int. Cl.
  *C07D 401/04* (2006.01)
  *C07D 401/14* (2006.01)
  *C07D 401/12* (2006.01)

(52) U.S. Cl.
  CPC ......... *C07D 401/04* (2013.01); *C07D 401/12* (2013.01); *C07D 401/14* (2013.01)

(58) Field of Classification Search
  CPC .................................................. C07D 401/04
  USPC ....................................................... 546/152
  See application file for complete search history.

(56) References Cited

U.S. PATENT DOCUMENTS 8,242,102 B2 * 8/2012 Turner ................. C07D 401/04
  514/210.2
2007/0249603 A1 * 10/2007 Johnson ............... C07D 401/04
  514/235.2

FOREIGN PATENT DOCUMENTS

| WO | 2005113539 A1 | 12/2005 |
|---|---|---|
| WO | 2007039219 A1 | 4/2007 |
| WO | 2007039238 A1 | 4/2007 |
| WO | 2009019286 | 2/2009 |
| WO | 03080580 A2 | 10/2013 |

OTHER PUBLICATIONS

Colomb, Journal of Medicinal Chemistry (2014), 57(9), 3884-3890.*
Menses, A., "Role of 5-HT6 Receptors in Memory Formation," Drug News Prospect, 2001, vol. 14(7), pp. 396-400.
Gannon, K.S. et al., "PRX-07034, a Potent and Selective 5-HT6 Receptor Antagonist, Reduces Food Intake and Body Weight in Rats," Journal of Pharmacological Sciences, 2006, vol. 101, p. 124.
Diaz, G. et al., "The [3H]dofetilide binding assay is a predictive screening tool for hERG blockade and proarrhythmia: Comparison of intact cell and membrane preparations and effects of altering [K+]o," Journal of Pharmacological and Toxicologic Methods, 2004, vol. 50, pp. 187-199.

* cited by examiner

*Primary Examiner* — Nizal S Chandrakumar
(74) *Attorney, Agent, or Firm* — Neal, Gerber & Eisenberg LLP

(57) ABSTRACT

The present invention relates to quinoline compounds of formula I

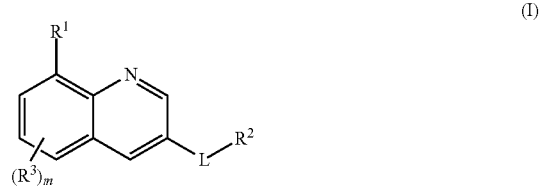

(I)

wherein the variables are defined as in the claims and the description. The invention further relates to a pharmaceutical composition containing such compounds, to their use as modulators of the 5-$HT_6$ receptor, their use for preparing a medicament for the prevention or treatment of conditions and disorders which respond to the modulation of the 5-$HT_6$ receptor, and to methods for preventing or treating conditions and disorders which respond to the modulation of the 5-$HT_6$ receptor.

17 Claims, No Drawings

QUINOLINE COMPOUNDS SUITABLE FOR TREATING DISORDERS THAT RESPOND TO THE MODULATION OF THE SEROTONIN 5-HT$_6$ RECEPTOR

CROSS-REFERENCE TO RELATED APPLICATIONS

This application claims the benefit of U.S. Provisional Application No. 62/307,823, filed Mar. 14, 2016, which is hereby incorporated by reference in its entirety.

FIELD OF THE INVENTION

The present invention relates to specific quinoline compounds, to a pharmaceutical composition containing such compounds, to their use as modulators of the 5-HT$_6$ receptor, their use for preparing a medicament for the prevention or treatment of conditions and disorders which respond to the modulation of 5-HT$_6$ receptor, to methods for preventing or treating conditions and disorders which respond to the modulation of 5-HT$_6$ receptor, and processes for preparing such compounds and compositions.

BACKGROUND OF THE INVENTION

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of either adenylate cyclase or phospholipase Cγ.

The human 5-HT$_6$ receptors are positively coupled to adenylyl cyclase. They are distributed throughout the limbic, striatal and cortical regions of the brain and show a high affinity to antipsychotics.

The modulation of the 5-HT$_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases and obesity (see e.g. A. Meneses, Drug News Perspect 14(7) (2001) pp. 396-400 and literature cited therein; J. Pharmacol. Sci. Vol. 101 (Suppl. 1), 2006, p. 124. Modulators of the 5HT$_6$-receptor such as PRX-07034 (Epix Pharmaceuticals) have been found in preclinical and clinical studies to be particular useful in the treatment of cognitive dysfunctions, in particular associated with Alzheimer's disease or schizophrenia or in the treatment of obesity (see e.g. http://www.epixpharma.com/products/prx-07034.asp).

Compounds with a structural similarity to the compounds of the present invention have been described in WO 03/080580, WO 2005/113539, WO 2007/039219, WO 2007/039238 and WO 2009/019286.

However, there is still an ongoing need for providing compounds having high affinity for the 5-HT$_6$ receptor and which advantageously also show high selectivity to this receptor.

Besides the binding affinity for the 5-HT$_6$ receptor, further properties may be advantageous for the treatment and/or prophylaxis of 5-HT$_6$-dependent disorders, such as, for example:

1.) a selectivity for the 5-HT$_6$ receptor compared with the 5-HT$_{1A}$ receptor, i.e. the quotient of the binding affinity for the 5-HT$_{1A}$ receptor (Ki(5-HT$_{1A}$) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{1A}$)/Ki(5-HT$_6$) means a greater 5-HT$_6$ selectivity;

2.) a selectivity for the 5-HT$_6$ receptor compared with the 5-HT$_{2A}$ receptor, i.e. the quotient of the binding affinity for the 5-HT$_{2A}$ receptor (Ki(5-HT$_{2A}$) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{2A}$)/Ki(5-HT$_6$) means a greater 5-HT$_6$ selectivity.

3.) a selectivity for the 5-HT$_6$ receptor compared with the 5-HT$_{2B}$ receptor, i.e. the quotient of the binding affinity for the 5-HT$_{2B}$ receptor (Ki(5-HT$_{2B}$) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{2B}$)/Ki(5-HT$_6$) means a greater 5-HT$_6$ selectivity.

4.) a low affinity to adrenergic receptors, such as $\alpha_1$-adrenergic receptor, histamine receptors, such as H$_1$-receptor, and dopaminergic receptors, such as D$_2$-receptor, in order to avoid or reduce considerable side effects associated with modulation of these receptors, such as postural hypotension, reflex tachycardia, potentiation of the antihypertensive effect of prazosin, terazosin, doxazosin and labetalol or dizziness associated to the blockade of the $\alpha_1$-adrenergic receptor, weight gain, sedation, drowsiness or potentiation of central depressant drugs associated to the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the D$_2$-receptor.

5.) the metabolic stability, for example determined from the half-lives, measured in vitro, in liver microsomes from various species (e.g. rat or human);

6.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

7.) a suitable solubility in water (in mg/ml);

8.) suitable pharmacokinetics (time course of the concentration of the compound of the invention in plasma or in tissue, for example brain). The pharmacokinetics can be described by the following parameters: half-life (in h), volume of distribution (in $l \cdot kg^{-1}$), plasma clearance (in $l \cdot h^{-1} \cdot kg^{-1}$), AUC (area under the curve, area under the concentration-time curve, in $ng \cdot h \cdot l^{-1}$), oral bioavailability (the dose-normalized ratio of AUC after oral administration and AUC after intravenous administration), the so-called brain-plasma ratio (the ratio of AUC in brain tissue and AUC in plasma);

9.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. Moreover, the blockade of the hERG channel can be measured by electrophysiological experiments on cells which have been transfected with the hERG channel, by so-called whole-cell patch clamping, as shown in the below assay (G. J. Diaz et al., Journal of Pharmacological and Toxicological Methods, 50 (2004), 187-199). The higher the $K_i$ values in the below assay (determined in the unit "micromolar (μM)"), the lower the probability of potent hERG blockade.

One object of the present invention was to provide compounds which have a high affinity for the 5-HT$_6$ receptor. A further object of the present invention was to provide compounds which selectively bind to the 5-HT$_6$ receptor [especially as mentioned above under 1.), 2.), 3.) and/or 4.)]. In addition, the compounds of the invention should have one or more of the aforementioned advantages mentioned under 5.) to 9.) and specifically under 5.) (metabolic stability).

The present invention provides compounds which have an affinity for the 5-HT$_6$ receptor, thus allowing the treatment of disorders related to or affected by the 5-HT$_6$ receptor.

SUMMARY OF THE INVENTION

The present invention relates to quinoline compounds which comprise an N-bound saturated heteromono- or -bicyclic ring containing one (and only one) nitrogen atom as ring member (the one via which the ring is bound), where this N-bound ring carries 1, 2 or 3 specific oxygen-containing substituents and where the ring is either bound in 8-position of the quinoline scaffold or is bound to the (hetero)aromatic ring in the 3-position of the quinoline scaffold; to a pharmaceutical composition containing such compounds, to such compounds for use as a medicament and to such compounds for use in the prevention or treatment of conditions and disorders which respond to the modulation of 5-HT$_6$ receptor, to their use as modulators of the 5-HT$_6$ receptor, to their use for preparing a medicament for the prevention or treatment of conditions and disorders which respond to the modulation of 5-HT$_6$ receptor, to methods for preventing or treating conditions and disorders which respond to the modulation of 5-HT$_6$ receptor, and to processes for preparing such compounds and compositions.

In one aspect, the present invention relates to compounds of the formula I:

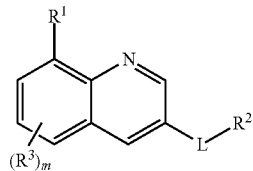

(I)

wherein $R^1$ is selected from the group consisting of a ring $R^a$, halogen, $C_1$-$C_2$-haloalkyl, $C_1$-$C_2$-alkoxy, $C_1$-$C_2$-haloalkoxy, an N-bound saturated 3-, 4-, 5-, 6-, 7- or 8-membered heteromonocyclic ring containing one or two nitrogen atoms as ring members; and an N-bound saturated 7-, 8-, 9-, 10-, 11- or 12-membered heterobicyclic ring containing one or two nitrogen atoms as ring members; where the heteromonocyclic ring and the heterobicyclic ring may carry one or more substituents $R^4$;

$R^2$ is selected from the group consisting of a phenyl ring, a naphthyl ring, a 5- or 6-membered monocyclic heteroaromatic ring containing 1, 2, 3 or 4 heteroatoms selected from the group consisting of N, O and S as ring members, and a 9- or 10-membered bicyclic heteroaromatic ring containing 1, 2, 3 or 4 heteroatoms selected from the group consisting of N, O and S as ring members, where the phenyl, the naphthyl and the monocyclic or bicyclic heteroaromatic ring may carry one ring $R^a$ and/or one or more substituents $R^5$;

with the proviso that $R^1$ is $R^a$ if the ring $R^2$ is not substituted by $R^a$;

each $R^3$ is independently selected from the group consisting of halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl and di-($C_1$-$C_6$-alkyl)-aminocarbonyl;

each $R^4$ is independently selected from the group consisting of halogen, cyano, nitro, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and oxo;

each $R^5$ is independently selected from the group consisting of halogen, cyano, nitro, hydroxyl, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_6$-alkylcarbonyl, $C_1$-$C_6$-haloalkylcarbonyl, carboxyl, carboxyl-$C_1$-$C_2$-alkyl, $C_1$-$C_6$-alkoxycarbonyl, $C_1$-$C_6$-haloalkoxycarbonyl, amino, $C_1$-$C_6$-alkylamino, di-($C_1$-$C_6$-alkyl)-amino, aminocarbonyl, $C_1$-$C_6$-alkylaminocarbonyl, di-($C_1$-$C_6$-alkyl)-aminocarbonyl, phenyl which may carry one or more substituents $R^6$; and a 3-, 4-, 5-, 6-, 7- or 8-membered saturated, partially unsaturated or maximally unsaturated heterocyclic ring containing 1, 2 or 3 heteroatoms or heteroatom groups selected from the group consisting of N, O, S, NO, S(O) and S(O)$_2$ as ring members, where the heterocyclic ring may carry one or more substituents $R^7$;

each $R^6$ is independently selected from the group consisting of halogen, cyano, nitro, hydroxyl, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_6$-alkylcarbonyl, $C_1$-$C_6$-haloalkylcarbonyl, carboxyl, carboxyl-$C_1$-$C_2$-alkyl, $C_1$-$C_6$-alkoxycarbonyl, $C_1$-$C_6$-haloalkoxycarbonyl, amino, $C_1$-$C_6$-alkylamino, di-($C_1$-$C_6$-alkyl)-amino, and —C(O)N($R^8$)$R^9$;

each $R^7$ is independently selected from the group consisting of halogen, cyano, nitro, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, amino, $C_1$-$C_6$-alkylamino and di-($C_1$-$C_6$-alkyl)-amino;

$R^8$ and $R^9$, independently of each other and independently of each occurrence, are selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, $C_1$-$C_4$-alkoxy, $C_1$-$C_4$-haloalkoxy, phenyl and benzyl; or $R^8$ and $R^9$, together with the nitrogen atom they are bound to, form a 3-, 4-, 5-, 6- 7- or 8-membered saturated heterocyclic ring which may contain 1, 2 or 3 additional heteroatoms or heteroatom groups selected from the group consisting of N, O, S, NO, S(O) and S(O)$_2$; where the ring may carry 1, 2 or 3 substituents selected from the group consisting of halogen, cyano, nitro, hydroxyl, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_6$-alkylcarbonyl, $C_1$-$C_6$-haloalkylcarbonyl, carboxyl, $C_1$-$C_6$-alkoxycarbonyl and $C_1$-$C_6$-haloalkoxycarbonyl;

L is a S(O)$_2$, CH$_2$—S(O)$_2$, S(O)$_2$—CH$_2$, C(O)—NH, NH—C(O) NH—S(O)$_2$ or S(O)$_2$—NH;

$R^a$ is an N-bound saturated 3-, 4-, 5-, 6-, 7- or 8-membered heteromonocyclic ring containing one (and only one) nitrogen atom as ring member (which is the nitrogen atom via which this ring is bound); or an N-bound saturated 7-, 8-, 9-, 10-, 11- or 12-membered heterobicyclic ring containing one (and only one) nitrogen atom as ring member (which is the nitrogen atom via which this ring is bound), where the heteromonocyclic or heterobicyclic ring carries 1, 2 or 3 substituents $R^b$ and optionally 1 or 2 further substituents $R^4$;

$R^b$ is an oxygen-containing radical independently selected from the group consisting of hydroxyl, $C_1$-$C_4$-alkoxy, —C(O)OH, —CH$_2$—C(O)OH and —C(O)N($R^8$)$R^9$; and m is 0, 1 or 2;

and the N-oxides, tautomeric forms, stereoisomers and pharmaceutically acceptable salts thereof; and the compound of the general formula I, wherein at least one of the atoms has been replaced by its stable, non-radioactive isotope.

In another aspect, the invention relates to a pharmaceutical composition comprising a therapeutically effective amount of at least one compound of formula I or an N-oxide, a tautomeric form, a stereoisomer or a pharmaceutically acceptable salt thereof, or a compound of the general formula I, wherein at least one of the atoms has been replaced by its stable, non-radioactive isotope, in combination with at least one pharmaceutically acceptable carrier and/or auxiliary substance.

In yet another aspect, the invention relates to a compound of formula I or an N-oxide, a tautomeric form, a stereoisomer or a pharmaceutically acceptable salt thereof or a compound of the general formula I, wherein at least one of the atoms has been replaced by its stable, non-radioactive isotope, for use as a medicament.

In yet another aspect, the invention relates to a compound of formula I or an N-oxide, a tautomeric form, a stereoisomer or a pharmaceutically acceptable salt thereof or a compound of the general formula I, wherein at least one of the atoms has been replaced by its stable, non-radioactive isotope, for use in the treatment of disorders which respond to the modulation of the 5-HT$_6$ receptor.

In yet another aspect, the invention relates to a compound of formula I or an N-oxide, a tautomeric form, a stereoisomer or a pharmaceutically acceptable salt thereof or a compound of the general formula I, wherein at least one of the atoms has been replaced by its stable, non-radioactive isotope, for use in the treatment of disorders selected from the group consisting of disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, including hydrocephalus, addiction, in particular drug addiction, and obesity.

In yet another aspect, the invention relates to the use of a compound of formula I or of an N-oxide, a tautomeric form, a stereoisomer or a pharmaceutically acceptable salt thereof or a compound of the general formula I, wherein at least one of the atoms has been replaced by its stable, non-radioactive isotope, for the manufacture of a medicament for the treatment of disorders which respond to the modulation of the 5-HT$_6$ receptor.

In yet another aspect, the invention relates to the use of a compound of formula I or of an N-oxide, a stereoisomer or a pharmaceutically acceptable salt thereof or a compound of the general formula I, wherein at least one of the atoms has been replaced by its stable, non-radioactive isotope, for the manufacture of a medicament for the treatment of disorders selected from the group consisting of disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, including hydrocephalus, addiction, in particular drug addiction, and obesity.

In yet another aspect, the invention relates to a method for treating disorders which respond to the modulation of the 5-HT$_6$ receptor, which method comprises administering to a subject in need thereof at least one compound of formula I or an N-oxide, a tautomeric form, a stereoisomer or a pharmaceutically acceptable salt thereof or a compound of the general formula I, wherein at least one of the atoms has been replaced by its stable, non-radioactive isotope.

In yet another aspect, the invention relates to a method for treating disorders selected from the group consisting of disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, including hydrocephalus, addiction, in particular drug addiction, and obesity, which method comprises administering to a subject in need thereof at least one compound of formula I or an N-oxide, a tautomeric form, a stereoisomer or a pharmaceutically acceptable salt thereof or a compound of the general formula I, wherein at least one of the atoms has been replaced by its stable, non-radioactive isotope.

DETAILED DESCRIPTION

The proviso that $R^1$ is $R^a$ if the ring $R^2$ is not substituted by $R^a$ means that either $R^1$ is $R^a$ and $R^2$ can have any of the above definitions, or $R^2$ is a phenyl, naphthyl or a monocyclic or bicyclic heteroaromatic ring as defined above which carries a ring $R^a$ (and optionally one or more substituents $R^5$) and $R^1$ can have any of the above definitions. As can be understood from the above, it is of course possible that $R^1$ is $R^a$ and simultaneously the phenyl, naphthyl or heteroaromatic ring $R^2$ carries a ring $R^a$.

The compounds of the formula I may exist in different spatial arrangements, for example if they possess one or more centers of asymmetry, polysubstituted rings or double bonds. The invention relates to enantiomeric mixtures, in particular racemates, diastereomeric mixtures, as well as to the respective essentially pure enantiomers and diastereomers of the compounds of formula I and/or of their salts and/or their N-oxides and/or their tautomeric forms and/or their prodrugs and/or of compounds of the formula I, wherein at least one of the atoms has been replaced by its stable, non-radioactive isotope.

For instance, rings $R^a$ can contain one or more centers of asymmetry. If this ring has no rotary reflexion axis and does not carry two geminally bound, identical substituents $R^b$ and/or two geminally bound, identical substituents $R^4$—in other words if ring $R^a$ is not present in meso form—compounds I may be present in form of different enantiomers, diastereomers or enantiomeric or diastereomeric mixtures.

In the terms of the present invention, "prodrugs" are compounds which are metabolized in vivo to give the compounds of the invention of formula I. Typical examples for prodrugs are for example described in C. G. Wermeth (editor): The Practice of Medicinal Chemistry, Academic Press, San Diego, 1996, pages 671-715. Examples are phosphates, carbamates, aminoacids, esters, amides, peptides, urea and the like. In the present case, suitable prodrugs can be compounds of formula I wherein a primary or secondary nitrogen atom, for example the nitrogen atom of an amino or $C_1$-$C_6$-alkylamino group $R^5$, $R^6$ or $R^7$ or a secondary nitrogen atom of a 3-, 4-, 5-, 6-, 7- or 8-membered saturated, partially unsaturated or maximally unsaturated heterocyclic ring $R^5$ or a secondary nitrogen atom of an N-bound saturated 3-, 4-, 5-, 6-, 7- or 8-membered heteromonocyclic ring $R^1$ containing two nitrogen atoms as ring members or of an N-bound saturated 7-, 8-, 9-, 10-, 11- or 12-membered heterobicyclic ring $R^1$ containing two nitrogen atoms as ring members, forms an amide/peptide bond in that this nitrogen atom is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an aminoacid group bonded via CO, e.g. glycine, alanine, serine, phenylalanine and the like bonded via CO. Suitable prodrugs are furthermore alkylcarbonyloxyalkylcarbamates, wherein said nitrogen atom carries a group —C(=O)—O—CHR$^x$—O—C(=O)—R$^y$, wherein R$^x$ und R$^y$ independently of each other are $C_1$-$C_4$-alkyl. These carbamate compounds are for example described in J. Alexander, R. Cargill, S. R. Michelson, H. Schwam, J. Medicinal Chem. 1988, 31(2), 318-322.

In other words, prodrugs of compounds I are for example:
compounds I in which one of $R^5$, $R^6$ or $R^7$ is —NHR or —N($C_1$-$C_6$-alkyl)R, where R is $C_1$-$C_4$-alkylcarbonyl, in particular acetyl, propionyl, n-propylcarbonyl, isopropylcarbonyl, n-butylcarbonyl or tert-butylcarbonyl (pivaloyl), or R is benzoyl, or R is an aminoacid group bonded via CO, in particular a glycine, alanine, serine or phenylalanine residue bonded via CO, or R is —C(=O)—O—CHR$^x$—O—C(=O)—R$^y$, wherein R$^x$ und R$^y$ independently of each other are $C_1$-$C_4$-alkyl; or are compounds I in which at least one $R^5$ is a 3-, 4-, 5-, 6-, 7- or 8-membered saturated, partially unsaturated or maximally unsaturated heterocyclic ring containing 1, 2 or 3 heteroatoms or heteroatom groups selected from the group consisting of N, O, S, NO, S(O) and S(O)$_2$ as ring members, where at least one of these heteroatoms or heteroatom groups is a group NR, where R is $C_1$-$C_4$-alkylcarbonyl, in particular acetyl, propionyl, n-propylcarbonyl, isopropylcarbonyl, n-butylcarbonyl or tert-butylcarbonyl (pivaloyl), or R is benzoyl, or R is an aminoacid group bonded via CO, in particular a glycine, alanine, serine or phenylalanine residue bonded via CO, or R is —C(=O)—O—CHR$^x$—O—C(=O)—R$^y$, wherein R$^x$ und R$^y$ independently of each other are $C_1$-$C_4$-alkyl, where the heterocyclic ring may additionally carry one or more substituents $R^7$;

or are compounds I in which $R^1$ is an N-bound saturated 3-, 4-, 5-, 6-, 7- or 8-membered heteromonocyclic ring $R^1$ containing two nitrogen atoms as ring members or is an N-bound saturated 7-, 8-, 9-, 10-, 11- or 12-membered heterobicyclic ring $R^1$ containing two nitrogen atoms as ring members, where the second nitrogen atom in this heteromono- or -bicyclic ring via which the ring is not bound to the quinoline scaffold is present as a group NR, where R is $C_1$-$C_4$-alkylcarbonyl, in particular acetyl, propionyl, n-propylcarbonyl, isopropylcarbonyl, n-butylcarbonyl or tert-butylcarbonyl (pivaloyl), or R is benzoyl, or R is an aminoacid group bonded via CO, in particular a glycine, alanine, serine or phenylalanine residue bonded via CO, or R is —C(=O)—O—CHR$^x$—O—C(=O)—R$^y$, wherein R$^x$ und R$^y$ independently of each other are $C_1$-$C_4$-alkyl; where the heteromonocyclic ring and the heterobicyclic ring may additionally carry one or more substituents $R^4$.

These groups can be removed under metabolic conditions and result in compounds of formula I, wherein said nitrogen atom carries a hydrogen atom instead.

The invention also relates to N-oxides of the compounds of the formula I, provided that those compounds contain a basic nitrogen atom, such as the nitrogen atom of the quinoline ring or of various heterocyclic moieties $R^1$, $R^2$ and $R^5$ containing at least one basic nitrogen atom as ring member.

The invention also relates to tautomeric forms of the compounds of the formula I, present e.g. in compounds I containing amide groups or lactame groups or in which an OH group is bound to a C=C or C=N double bond. Under given conditions, one tautomeric form often predominates, but as the transition of one tautomeric form to another is generally an equilibrium reaction, the presence of the non-favoured form can generally not be excluded.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, acetic acid, trifluoroacetic acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 et seq., Birkhäuser Verlag, Basel and Stuttgart, 1966.

The organic moieties mentioned in the above definitions of the variables are, like the term halogen, collective terms for individual listings of the individual group members. The prefix $C_n$-$C_m$ indicates in each case the possible number of carbon atoms in the group.

The term "halogen" denotes in each case fluorine, bromine, chlorine or iodine. In one aspect, the halogen may be fluorine, chlorine or bromine.

The term "alkyl" as used herein and in the alkyl moieties of alkoxy and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is methyl or ethyl. Examples for $C_1$-$C_3$-alkyl are, in addition to those mentioned for $C_1$-$C_2$-alkyl, propyl and isopropyl. Examples for $C_1$-$C_4$-alkyl are, in addition to those mentioned for $C_1$-$C_3$-alkyl, butyl, 1-methylpropyl (sec-butyl), 2-methylpropyl (isobutyl) or 1,1-dimethylethyl (tert-butyl). Examples for $C_1$-$C_6$-alkyl are, in addition to those mentioned for $C_1$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "fluorinated alkyl" as used herein refers to straight-chain or branched alkyl groups having 1 to 2 ("fluorinated $C_1$-$C_2$-alkyl"), 1 to 3 ("fluorinated $C_1$-$C_3$-alkyl"), 1 to 4 ("fluorinated $C_1$-$C_4$-alkyl") or 1 to 6 ("fluorinated $C_1$-$C_6$-alkyl") carbon atoms (as mentioned above), where some or all of the hydrogen atoms in these, groups are replaced by fluorine atoms. Fluorinated methyl is fluoromethyl ($CH_2F$), difluoromethyl ($CHF_2$) or trifluoromethyl ($CF_3$). Fluorinated $C_1$-$C_2$-alkyl is an alkyl group having 1 or 2 carbon atoms (as mentioned above), where at least one of the hydrogen atoms, e.g. 1, 2, 3, 4 or 5 hydrogen atoms in these groups are replaced by fluorine atoms, such as fluoromethyl, difluoromethyl, trifluoromethyl, 1-fluoroethyl, (R)-1-fluoroethyl, (S)-1-fluoroethyl, 2-fluoroethyl, 2,2-difluoroethyl, 2,2,2-trifluoroethyl, or pentafluoroethyl. Fluorinated $C_1$-$C_3$-alkyl is a straight-chain or branched alkyl group having 1 to 3 carbon atoms (as mentioned above), where at least one of the hydrogen atoms, e.g. 1, 2, 3, 4 or 5 hydrogen atoms in these groups are replaced by fluorine atoms. Examples are, in addition to those listed above for fluorinated $C_1$-$C_2$-alkyl, 1-fluoropropyl, (R)-1-fluoropropyl, (S)-1-fluoropropyl, 2-fluoropropyl, (R)-2-fluoropropyl, (S)-2-fluoropropyl, 3-fluoropropyl, 1,1-difluoropropyl, 2,2-difluoropropyl, 1,2-difluoropropyl, 2,3-difluoropropyl, 1,3-difluoropropyl, 3,3-difluoropropyl, 1,1,2-trifluoropropyl, 1,2,2-trifluoropropyl, 1,2,3-trifluoropropyl, 2,2,3-trifluoropropyl, 3,3,3-trifluoropropyl, 1,1,1-trifluoroprop-2-yl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl and 1-(trifluoromethyl)-1,2,2,2-tetrafluoroethyl. Fluorinated $C_1$-$C_4$-alkyl is a straight-chain or branched alkyl group having 1 to 4 carbon atoms (as mentioned above), where at least one of the hydrogen atoms, e.g. 1, 2, 3, 4 or 5 hydrogen atoms in these groups are replaced by fluorine atoms. Examples are, in addition to those listed above for fluorinated $C_1$-$C_3$-alkyl, 1-fluorobutyl, (R)-1-fluorobutyl, (S)-1-fluorobutyl, 2-fluorobutyl, (R)-2-fluorobutyl, (S)-2-fluorobutyl, 3-fluorobutyl, (R)-3-fluorobutyl, (S)-3-fluorobutyl, 4-fluorobutyl, 1,1-difluorobutyl, 2,2-difluorobutyl, 3,3-difluorobutyl, 4,4-difluorobutyl, 4,4,4-trifluorobutyl and the like. Fluorinated $C_1$-$C_6$-alkyl is a straight-chain or branched alkyl group having 1 to 6 carbon atoms (as mentioned above), where at least one of the hydrogen atoms, e.g. 1, 2, 3, 4 or 5 hydrogen atoms in these groups are replaced by fluorine atoms. Examples are, in addition to those listed above for fluorinated $C_1$-$C_4$-alkyl, 1-fluoropentyl, (R)-1-fluoropentyl, (S)-1-fluoropentyl, 2-fluoropentyl, (R)-2-fluoropentyl, (S)-2-fluoropentyl, 3-fluoropentyl, (R)-3-fluoropentyl, (S)-3-fluoropentyl, 4-fluoropentyl, (R)-4-fluoropentyl, (S)-4-fluoropentyl, 5-fluoropentyl, (R)-5-fluoropentyl, (S)-5-fluoropentyl, 1-fluorohexyl, (R)-1-fluorohexyl, (S)-1-fluorohexyl, 2-fluorohexyl, (R)-2-fluorohexyl, (S)-2-fluorohexyl, 3-fluorohexyl, (R)-3-fluorohexyl, (S)-3-fluorohexyl, 4-fluorohexyl, (R)-4-fluorohexyl, (S)-4-fluorohexyl, 5-fluorohexyl, (R)-5-fluorohexyl, (S)-5-fluorohexyl, 6-fluorohexyl, (R)-6- fluorohexyl, (S)-6-fluorohexyl, and the like. Fluorinated $C_1$-$C_8$-alkyl is a straight-chain or branched alkyl group having 1 to 8 carbon atoms (as mentioned above), where at least one of the hydrogen atoms, e.g. 1, 2, 3, 4 or 5 hydrogen atoms in these groups are replaced by fluorine atoms.

The term "haloalkyl" as used herein, which may also be expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl") or 1 to 4 ("$C_1$-$C_6$-haloalkyl") carbon atoms (as mentioned above), where some or all of the hydrogen atoms in these groups are replaced by halogen atoms as mentioned above. Examples for $C_1$-$C_2$-haloalkyl are, in addition to those listed above for fluorinated $C_1$-$C_2$-alkyl, chloromethyl, bromomethyl, dichloromethyl, trichloromethyl, chlorofluoromethyl, dichlorofluoromethyl, chlorodifluoromethyl, 1-chloroethyl, 1-bromoethyl, 2-chloro-2-fluoroethyl, 2-chloro-2,2-difluoroethyl, 2,2-dichloro-2-fluoroethyl or 2,2,2-trichloroethyl. Examples for $C_1$-$C_3$-haloalkyl are, in addition to those listed above for $C_1$-$C_2$-haloalkyl and for fluorinated $C_1$-$C_3$-alkyl, 3-chloropropyl and the like. Examples for $C_1$-$C_4$-haloalkyl are, in addition to those mentioned above for $C_1$-$C_3$-haloalkyl and for fluorinated $C_1$-$C_4$-alkyl, 4-chlorobutyl and the like. Examples for $C_1$-$C_6$-haloalkyl are, in addition to those mentioned above for $C_1$-$C_4$-haloalkyl and for fluorinated $C_1$-$C_6$-alkyl, 5-chloropentyl, 6-chlorohexyl and the like.

The term "cycloalkyl" as used herein refers to monocyclic saturated hydrocarbon radicals having 3 to 6 carbon atoms ("$C_3$-$C_6$-cycloalkyl"). Examples of $C_3$-$C_6$-cycloalkyl are cyclopropyl, cyclobutyl, cyclopentyl and cyclohexyl.

The term "halocycloalkyl" as used herein refers to monocyclic saturated hydrocarbon groups having 3 to 6 ("$C_3$-$C_6$-halocycloalkyl") carbon ring members (as mentioned above) in which some or all of the hydrogen atoms are replaced by halogen atoms. Examples are 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-chlorocyclopropyl, 2-chlorocyclopropyl, 2,3-dichlorocyclopropyl, 2-chloro-1-fluorocyclopropyl, 3-chloro-2-fluorocyclopropyl, 2-bromocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, 1,2,2-trifluorocyclobutyl, 1-chlorocyclobutyl, 2-chlorocyclobutyl, 3-chlorocyclobutyl, 2,2-dichlorocyclobutyl, 2,3-dichlorocyclobutyl, 3,3-dichlorocyclobutyl, 2-bromocyclobutyl, 3-bromocyclobutyl, 1-fluorocyclopentyl, 2-fluorocyclopentyl, 1,2-difluorocyclopentyl, 1,3-difluorocyclopentyl, 2,2-difluorocyclopentyl, 2,3-difluorocyclopentyl, 2,4-difluorocyclopentyl, 2,5-difluorocyclopentyl, 3,3-difluorocyclopentyl, 3,4-difluorocyclopentyl, 1-chlorocyclopentyl, 2-chlorocyclopentyl, 3-chlorocyclopentyl, 1-fluorocyclohexyl, 2-fluorocyclohexyl, 3-fluorocyclohexyl, 4-fluorocyclohexyl, 1,2-difluorocyclohexyl, 1,3-difluorocyclohexyl, 1,4-difluorocyclohexyl, 2,2-difluorocyclohexyl, 2,3-difluorocyclohexyl, 2,4-difluorocyclohexyl, 2,5-difluorocyclohexyl, 2,6-difluorocyclohexyl, 3,3-difluorocyclohexyl, 3,4-difluorocyclohexyl, 3,5-difluorocyclohexyl, 4,4-difluorocyclohexyl, 1-chlorocyclohexyl, 2-chlorocyclohexyl, 3-chlorocyclohexyl, 4-chlorocyclohexyl, and the like.

The term "$C_3$-$C_6$-cycloalkyl-$C_1$-$C_4$-alkyl" refers to a $C_3$-$C_6$-cycloalkyl group, as defined above, which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_4$-cycloalkyl-$C_1$-$C_4$-alkyl are, in addition to those mentioned for $C_3$-$C_4$-cycloalkyl-$C_1$-$C_4$-alkyl, cyclopentylmethyl, cyclopentylethyl, cyclopentylpropyl, cyclohexylmethyl, cyclohexylethyl, cyclohexylpropyl and the like.

The term "$C_3$-$C_6$-halocycloalkyl-$C_1$-$C_4$-alkyl" refers to a $C_3$-$C_6$-halocycloalkyl group, as defined above, which is bound to the remainder of the molecule via a $C_1$-$C_4$-alkyl group, as defined above.

"$C_1$-$C_2$-Alkoxy" is a $C_1$-$C_2$-alkyl group, as defined above, attached via an oxygen atom to the remainder of the molecule. "$C_1$-$C_3$-Alkoxy" is a $C_1$-$C_3$-alkyl group, as defined above, attached via an oxygen atom to the remainder of the molecule. "$C_1$-$C_4$-Alkoxy" is a $C_1$-$C_4$-alkyl group, as defined above, attached via an oxygen atom to the remainder of the molecule. "$C_1$-$C_6$-Alkoxy" is a $C_1$-$C_6$-alkyl group, as defined above, attached via an oxygen atom to the remainder of the molecule. $C_1$-$C_2$-Alkoxy is methoxy or ethoxy. Examples for $C_1$-$C_3$-alkoxy are, in addition to those mentioned for $C_1$-$C_2$-alkoxy, n-propoxy and 1-methylethoxy (isopropoxy). Examples for $C_1$-$C_4$-alkoxy are, in addition to those mentioned for $C_1$-$C_3$-alkoxy, butoxy, 1-methylpropoxy (sec-butoxy), 2-methylpropoxy (isobutoxy) or 1,1-dimethylethoxy (tert-butoxy). Examples for $C_1$-$C_6$-alkoxy are, in addition to those mentioned for $C_1$-$C_4$-alkoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

"$C_1$-$C_2$-Haloalkoxy" is a $C_1$-$C_2$-haloalkyl group, as defined above, attached via an oxygen atom to the remainder of the molecule. "$C_1$-$C_3$-Halolkoxy" is a $C_1$-$C_3$-haloalkyl group, as defined above, attached via an oxygen atom to the remainder of the molecule. "$C_1$-$C_4$-Haloalkoxy" is a $C_1$-$C_4$-haloalkyl group, as defined above, attached via an oxygen atom to the remainder of the molecule. "$C_1$-$C_6$-Haloalkoxy" is a $C_1$-$C_6$-haloalkyl group, as defined above, attached via an oxygen atom to the remainder of the molecule. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. Examples for $C_1$-$C_3$-haloalkoxy are, in addition to those mentioned for $C_1$-$C_2$-haloalkoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. Examples for $C_1$-$C_4$-haloalkoxy are, in addition to those mentioned for $C_1$-$C_3$-haloalkoxy, 4-fluorobutoxy, 4-chlorobutoxy, 4-bromobutoxy or nonafluorobutoxy. Examples for $C_1$-$C_6$-haloalkoxy are, in addition to those mentioned for $C_1$-$C_4$-haloalkoxy, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy.

"$C_1$-$C_2$-Alkylthio" is a $C_1$-$C_2$-alkyl group, as defined above, attached via a sulfur atom to the remainder of the molecule. "$C_1$-$C_3$-Alkylthio" is a $C_1$-$C_3$-alkyl group, as defined above, attached via a sulfur atom to the remainder of the molecule. "$C_1$-$C_4$-Alkylthio" is a $C_1$-$C_4$-alkyl group, as defined above, attached via a sulfur atom to the remainder of the molecule. "$C_1$-$C_6$-Alkylthio" is a $C_1$-$C_6$-alkyl group, as defined above, attached via a sulfur atom to the remainder of the molecule. $C_1$-$C_2$-Alkylthio is methylthio or ethylthio. Examples for $C_1$-$C_3$-alkylthio are, in addition to those mentioned for $C_1$-$C_2$-alkylthio, n-propylthio or 1-methylethylthio (isopropylthio). Examples for $C_1$-$C_4$-alkylthio are, in addition to those mentioned for $C_1$-$C_3$-alkylthio, butylthio, 1-methylpropylthio (sec-butylthio), 2-methylpropylthio (isobutylthio) or 1,1-dimethylethylthio (tert-butylthio). Examples for $C_1$-$C_6$-alkylthio are, in addition to those mentioned for $C_1$-$C_4$-alkylthio, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio.

"$C_1$-$C_2$-Haloalkylthio" is a $C_1$-$C_2$-haloalkyl group, as defined above, attached via a sulfur atom to the remainder of the molecule. "$C_1$-$C_3$-Haloalkylthio" is a $C_1$-$C_3$-haloalkyl group, as defined above, attached via a sulfur atom to the remainder of the molecule. "$C_1$-$C_4$-Haloalkylthio" is a $C_1$-$C_4$-haloalkyl group, as defined above, attached via a sulfur atom to the remainder of the molecule. "$C_1$-$C_6$-Haloalkylthio" is a $C_1$-$C_6$-haloalkyl group, as defined above, attached via a sulfur atom to the remainder of the molecule. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

"$C_1$-$C_2$-Alkylsulfinyl" is a $C_1$-$C_2$-alkyl group, as defined above, attached via a sulfinyl [S(O)] group to the remainder of the molecule. "$C_1$-$C_3$-Alkylsulfinyl" is a $C_1$-$C_3$-alkyl group, as defined above, attached via a sulfinyl [S(O)] group to the remainder of the molecule. "$C_1$-$C_4$-Alkylsulfinyl" is a $C_1$-$C_4$-alkyl group, as defined above, attached via a sulfinyl [S(O)] group to the remainder of the molecule. "$C_1$-$C_6$-Alkylsulfinyl" is a $C_1$-$C_6$-alkyl group, as defined above, attached via a sulfinyl [S(O)] group to the remainder of the molecule. $C_1$-$C_2$-Alkylsulfinyl is methylsulfinyl or ethylsulfinyl. Examples for $C_1$-$C_3$-alkylsulfinyl are, in addition to those mentioned for $C_1$-$C_2$-alkylsulfinyl, n-propylsulfinyl and 1-methylethylsulfinyl (isopropylsulfinyl). Examples for $C_1$-$C_4$-alkylsulfinyl are, in addition to those mentioned for $C_1$-$C_3$-alkylsulfinyl, butylsulfinyl, 1-methylpropylsulfinyl (sec-butylsulfinyl), 2-methylpropyisulfinyl (isobutylsulfinyl) and 1,1-dimethylethylsulfinyl (tert-butylsulfinyl). Examples for $C_1$-$C_6$-alkylsulfinyl are, in addition to those mentioned for $C_1$-$C_4$-alkylsulfinyl, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

"$C_1$-$C_2$-Haloalkylsulfinyl" is a $C_1$-$C_2$-haloalkyl group, as defined above, attached via a sulfinyl [S(O)] group to the remainder of the molecule. "$C_1$-$C_3$-Haloalkylsulfinyl" is a $C_1$-$C_3$-haloalkyl group, as defined above, attached via a sulfinyl [S(O)] group to the remainder of the molecule. "$C_1$-$C_4$-Haloalkylsulfinyl" is a $C_1$-$C_4$-haloalkyl group, as defined above, attached via a sulfinyl [S(O)] group to the remainder of the molecule. "$C_1$-$C_6$-Haloalkylsulfinyl" is a $C_1$-$C_6$-haloalkyl group, as defined above, attached via a sulfinyl [S(O)] group to the remainder of the molecule. $C_1$-$C_2$-Haloalkylsulfinyl is, for example, $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. Examples for $C_1$-$C_3$-haloalkylsulfinyl are, in addition to those mentioned for $C_1$-$C_2$-haloalkylsulfinyl, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl and 1-($CH_2Br$)-2-bromoethylsulfinyl. Examples for $C_1$-$C_4$-haloalkylsulfinyl are, in addition to those mentioned for $C_1$-$C_3$-haloalkylsulfinyl, 4-fluorobutylsulfinyl, 4-chlorobutylsulfinyl, 4-bromobutylsulfinyl or nonafluorobutylsulfinyl. Examples for $C_1$-$C_6$-haloalkylsulfinyl are, in addition to those mentioned for $C_1$-$C_4$-haloalkylsulfinyl, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

"$C_1$-$C_2$-Alkylsulfonyl" is a $C_1$-$C_2$-alkyl group, as defined above, attached via a sulfonyl [S(O)$_2$] group to the remainder of the molecule. "$C_1$-$C_3$-Alkylsulfonyl" is a $C_1$-$C_3$-alkyl group, as defined above, attached via a sulfonyl [S(O)$_2$] group to the remainder of the molecule. "$C_1$-$C_4$-Alkylsulfonyl" is a $C_1$-$C_4$-alkyl group, as defined above, attached via a sulfonyl [S(O)$_2$] group to the remainder of the molecule. "$C_1$-$C_6$-Alkylsulfonyl" is a $C_1$-$C_6$-alkyl group, as defined above, attached via a sulfonyl [S(O)$_2$] group to the remainder of the molecule. $C_1$-$C_2$-Alkylsulfonyl is methylsulfonyl or ethylsulfonyl. Examples for $C_1$-$C_3$-alkylsulfonyl are, in addition to those mentioned for $C_1$-$C_2$-alkylsulfonyl, n-propylsulfonyl or 1-methylethylsulfonyl (isopropylsulfonyl). Examples for $C_1$-$C_4$-alkylsulfonyl are, in addition to those mentioned for $C_1$-$C_3$-alkylsulfonyl, butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). Examples for $C_1$-$C_6$-alkylsulfonyl are, in addition to those mentioned for $C_1$-$C_4$-alkylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

"$C_1$-$C_2$-Haloalkylsulfonyl" is a $C_1$-$C_2$-haloalkyl group, as defined above, attached via a sulfonyl $[S(O)_2]$ group to the remainder of the molecule. "$C_1$-$C_3$-Haloalkylsulfonyl" is a $C_1$-$C_3$-haloalkyl group, as defined above, attached via a sulfonyl $[S(O)_2]$ group to the remainder of the molecule. "$C_1$-$C_4$-Haloalkylsulfonyl" is a $C_1$-$C_4$-haloalkyl group, as defined above, attached via a sulfonyl $[S(O)_2]$ group to the remainder of the molecule. "$C_1$-$C_6$-Haloalkylsulfonyl" is a $C_1$-$C_4$-haloalkyl group, as defined above, attached via a sulfonyl $[S(O)_2]$ group to the remainder of the molecule. $C_1$-$C_2$-Haloalkylsulfonyl is, for example, $S(O)_2CH_2F$, $S(O)_2CHF_2$, $S(O)_2CF_3$, $S(O)_2CH_2Cl$, $S(O)_2CHCl_2$, $S(O)_2CCl_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or $S(O)_2C_2F_5$. Examples for $C_1$-$C_3$-haloalkylsulfonyl are, in addition to those mentioned for $C_1$-$C_2$-haloalkylsulfonyl, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-($CH_2F$)-2-fluoroethylsulfonyl, 1-($CH_2Cl$)-2-chloroethylsulfonyl or 1-($CH_2Br$)-2-bromoethylsulfonyl. Examples for $C_1$-$C_4$-haloalkylsulfonyl are, in addition to those mentioned for $C_1$-$C_3$-haloalkylsulfonyl, 4-fluorobutylsulfonyl, 4-chlorobutylsulfonyl, 4-bromobutylsulfonyl or nonafluorobutylsulfonyl. Examples for $C_1$-$C_6$-haloalkylsulfonyl are, in addition to those mentioned for $C_1$-$C_4$-haloalkylsulfonyl, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

"Formyl" is a group —CH(=O).

"$C_1$-$C_6$-Alkylcarbonyl" is a $C_1$-$C_6$-alkyl group, as defined above, attached via a carbonyl [C(=O)] group to the remainder of the molecule. "$C_1$-$C_4$-Alkylcarbonyl" is a $C_1$-$C_4$-alkyl group, as defined above, attached via a carbonyl [C(=O)] group to the remainder of the molecule Examples are acetyl (methylcarbonyl), propionyl (ethylcarbonyl), propylcarbonyl, isopropylcarbonyl, n-butylcarbonyl and the like.

"$C_1$-$C_6$-Haloalkylcarbonyl" is a $C_1$-$C_6$-haloalkyl group, as defined above, attached via a carbonyl [C(=O)] group to the remainder of the molecule. "$C_1$-$C_4$-Haloalkylcarbonyl" is a $C_1$-$C_4$-haloalkyl group, as defined above, attached via a carbonyl [C(=O)] group to the remainder of the molecule. Examples are trifluoromethylcarbonyl, 2,2,2-trifluoroethylcarbonyl and the like.

"Carboxyl" is a group —C(=O)OH.

"Carboxyl-$C_1$-$C_2$-alkyl" is a carboxyl group bound via a $C_1$-$C_2$-alkyl group, i.e. —$CH_2$—C(O)OH, —$CH_2CH_2$—C(O)OH or CH($CH_3$)—C(O)OH.

"$C_1$-$C_6$-Alkoxycarbonyl" is a $C_1$-$C_6$-alkoxy group, as defined above, attached via a carbonyl [C(=O)] group to the remainder of the molecule. "$C_1$-$C_4$-Alkoxycarbonyl" is a $C_1$-$C_4$-alkoxy group, as defined above, attached via a carbonyl [C(=O)] group to the remainder of the molecule. Examples are methoxycarbonyl, ethoxycarbonyl, propoxycarbonyl, isopropoxycarbonyl, n-butoxycarbonyl and the like.

"$C_1$-$C_6$-Haloalkoxycarbonyl" is a $C_1$-$C_6$-haloalkoxy group, as defined above, attached via a carbonyl [C(=O)] group to the remainder of the molecule. "$C_1$-$C_4$-Haloalkoxycarbonyl" is a $C_1$-$C_4$-haloalkoxy group, as defined above, attached via a carbonyl [C(=O)] group to the remainder of the molecule. Examples are trifluoromethoxycarbonyl, 2,2,2-trifluoroethoxycarbonyl and the like.

"Amino" is —$NH_2$.

"$C_1$-$C_6$-alkylamino" is a group —N(H)—$C_1$-$C_6$-alkyl, where $C_1$-$C_6$-alkyl is as defined above Examples are methylamino, ethylamino, propylamino, isopropylamino, butylamino and the like.

The term "di($C_1$-$C_6$-alkyl)amino" is a group —N($C_1$-$C_6$-alkyl)$_2$, where each $C_1$-$C_6$-alkyl is independently as defined above. Examples are dimethylamino, diethylamino, ethylmethylamino, dipropylamino, diisopropylamino, methylpropylamino, methylisopropylamino, ethylpropylamino, ethylisopropylamino, dibutylamino and the like.

"Aminocarbonyl" is —C(O)—$NH_2$.

The term "$C_1$-$C_6$-alkylaminocarbonyl" is a group —C(=O)—N(H)—$C_1$-$C_6$-alkyl, where $C_1$-$C_6$-alkyl is as defined above Examples are methylaminocarbonyl, ethylaminocarbonyl, propylaminocarbonyl, isopropylaminocarbonyl, butylaminocarbonyl and the like.

The term "di($C_1$-$C_6$-alkyl)aminocarbonyl" is a group —C(=O)—N($C_1$-$C_6$-alkyl)$_2$, where each $C_1$-$C_6$-alkyl is independently as defined above. Examples are dimethylaminocarbonyl, diethylaminocarbonyl, ethylmethylaminocarbonyl, dipropylaminocarbonyl, diisopropylaminocarbonyl, methylpropylaminocarbonyl, methylisopropylaminocarbonyl, ethylpropylaminocarbonyl, ethylisopropylaminocarbonyl, dibutylaminocarbonyl and the like.

The substituent "oxo" replaces a $CH_2$ group by a C(=O) group.

"Ethyndiyl" is —C≡C—.

N-bound saturated 4-, 5- or 6-membered heteromonocyclic rings containing one nitrogen atom as ring member are azetidin-1-yl, pyrrolidin-1-yl or piperidine-1-yl.

N-bound saturated 3-, 4-, 5-, 6-, 7- or 8-membered heteromonocyclic rings containing one nitrogen atom as ring member are aziridin-1-yl, azetidin-1-yl, pyrrolidin-1-yl, piperidin-1-yl, azepan-1-yl or azocan-1-yl.

Examples for N-bound saturated 4-, 5- or 6-membered heteromonocyclic rings containing 1 or 2 nitrogen atoms as ring members are azetidin-1-yl, pyrrolidin-1-yl, piperidine- 1-yl, pyrazolidin-1-yl, imidazolodin-1-yl, piperazin-1-yl, hexahydropyridazin-1-yl or hexahydropyrimidin-1-yl.

Examples for N-bound saturated 3-, 4-, 5-, 6-, 7- or 8-membered heteromonocyclic rings containing 1 or 2 nitrogen atoms as ring member are aziridin-1-yl, azetidin-1-yl, pyrrolidin-1-yl, piperidine-1-yl, azepan-1-yl, azocan-1-yl, pyrazolidin-1-yl, imidazolodin-1-yl, piperazin-1-yl, hexahydropyridazin-1-yl, hexahydropyrimidin-1-yl, 1,2-diazepan-1-yl, 1,3-diazepan-1-yl, 1,4-diazepan-1-yl, 1,2-diazocan-1-yl, 1,3-diazocan-1-yl and 1,4-diazocan-1-yl.

The term "N-bound saturated 7-, 8-, 9-, 10-, 11- or 12-membered heterobicyclic rings containing one nitrogen atom as ring member" comprises condensed (fused) ring systems, in which the two rings have two neighboring ring atoms in common, as well as bridged systems with at least three ring atoms in common.

Examples for fused systems of N-bound saturated 7-, 8-, 9-, 10-, 11- or 12-membered heterobicyclic rings containing one nitrogen atom as ring member are following structures:

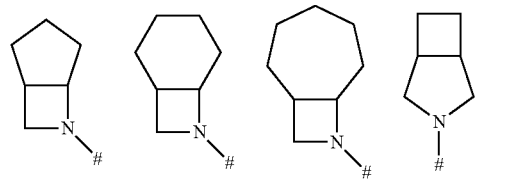

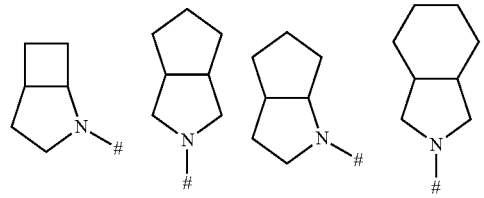

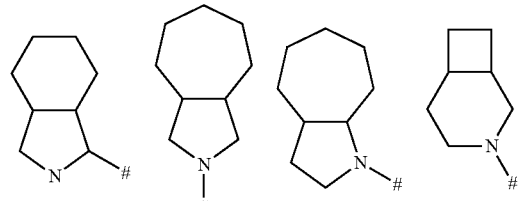

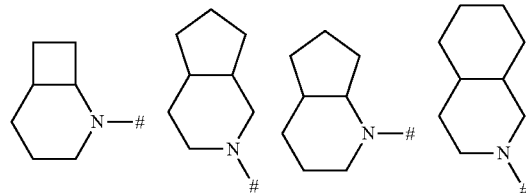

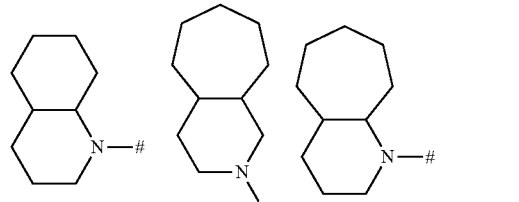

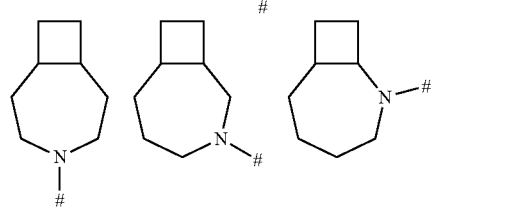

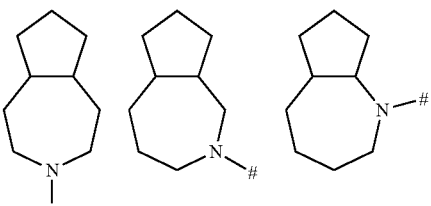

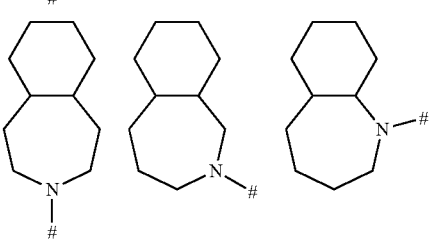

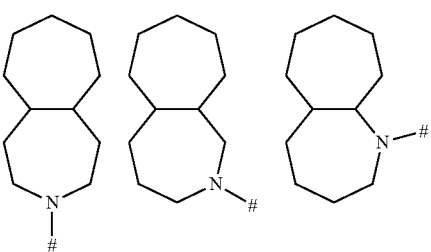

Examples for fused N-bound saturated 7-, 8-, 9-, 10-, 11- or 12-membered heterobicyclic rings containing one or two nitrogen atoms as ring members are the above structures of fused N-bound saturated 7-, 8-, 9-, 10-, 11- or 12-membered heterobicyclic rings containing one nitrogen atom as ring member, and additionally following structures:

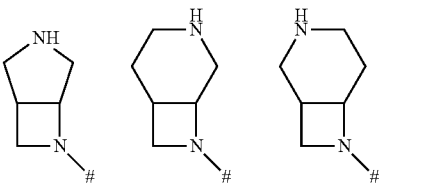

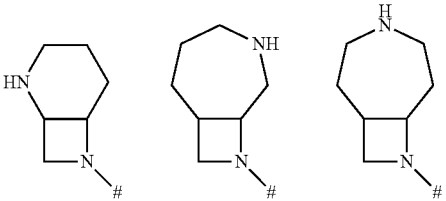

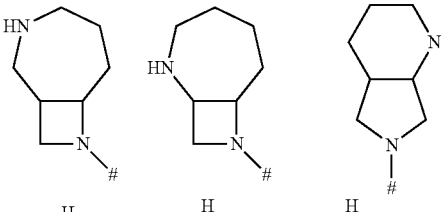

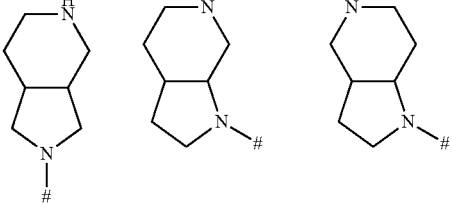

-continued
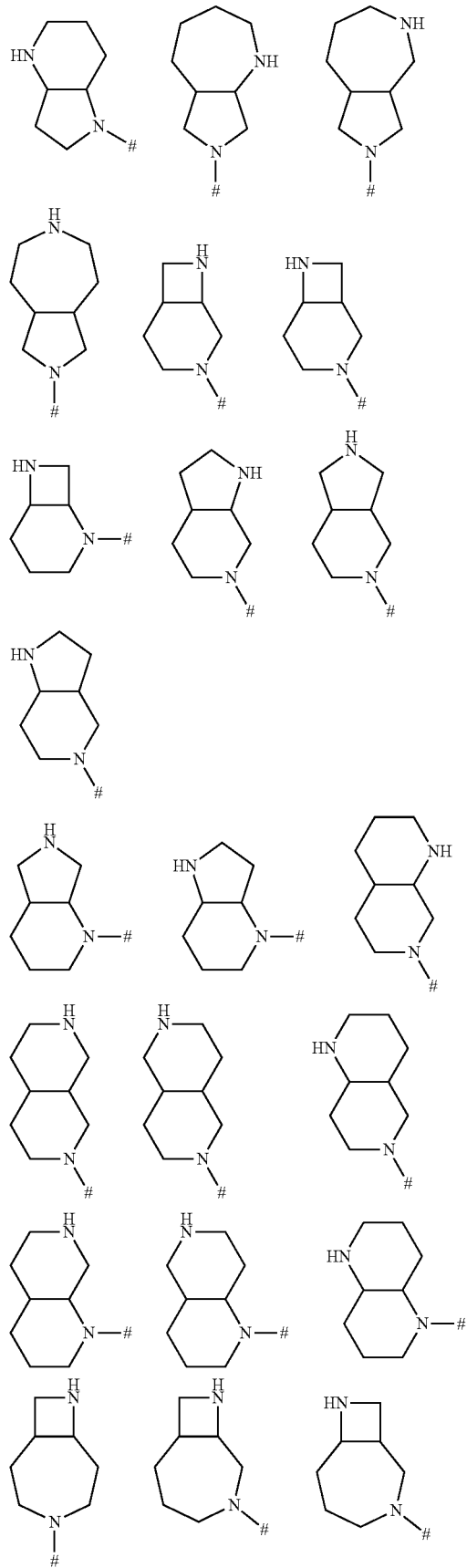
-continued
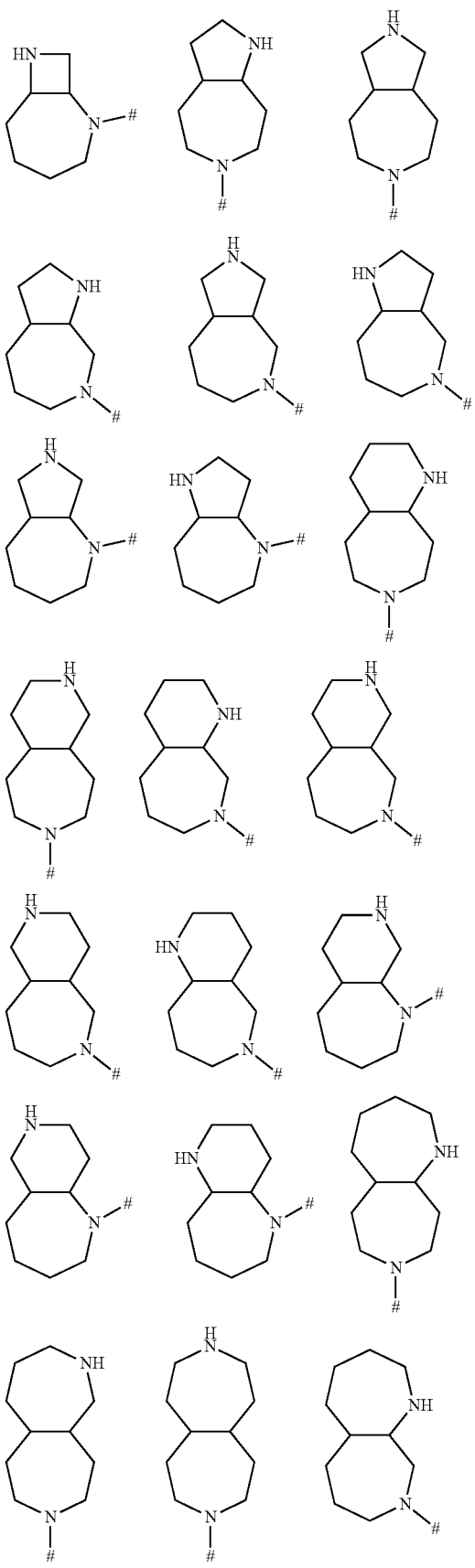

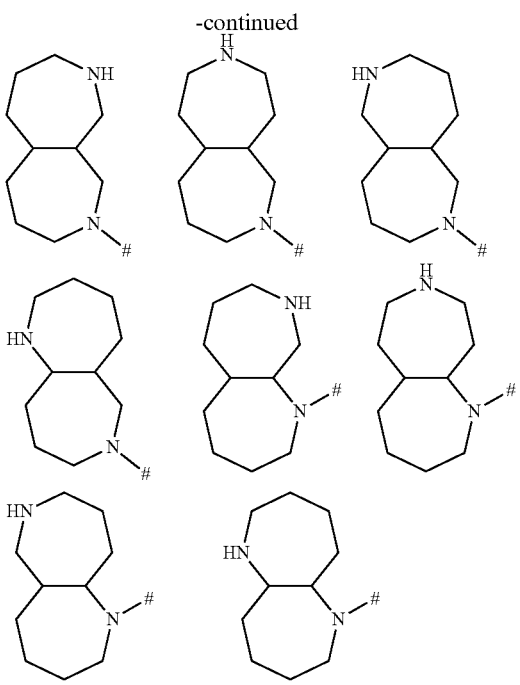

Examples for bridged systems of N-bound saturated 7-, 8-, 9-, 10-, 11- or 12-membered heterobicyclic rings containing one nitrogen atom as ring member are following structures:

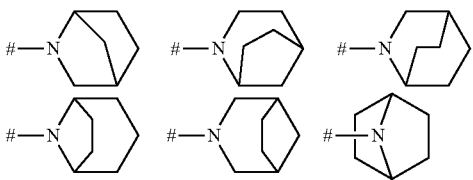

Examples for bridged systems of N-bound saturated 7-, 8-, 9-, 10-, 11- or 12-membered heterobicyclic rings containing one or two nitrogen atoms as ring members are the above structures of bridged N-bound saturated 7-, 8-, 9-, 10-, 11- or 12-membered heterobicyclic rings containing one nitrogen atom as ring member, and additionally following structures:

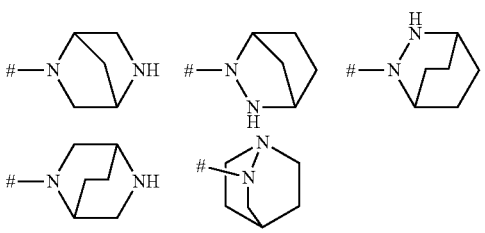

In the above structures, # denotes the attachment point to the remainder of the molecule. If the rings carry one or more substituents, these may be bound to a carbon or a nitrogen ring atom and to any one of the two rings.

The term "3-, 4-, 5-, 6-, 7- or 8-membered saturated, partially unsaturated or maximally unsaturated heterocyclic ring containing 1, 2 or 3 heteroatoms or heteroatom groups selected from the group consisting of N, O, S, NO, SO and SO$_2$, as ring members" [wherein "maximum unsaturated" includes also "aromatic"] as used herein denotes monocyclic radicals, the monocyclic radicals being saturated, partially unsaturated or maximum unsaturated (including aromatic).

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heteromonocyclic rings are generally aromatic (and thus not enclosed in the present term "heterocyclic ring" or "heterocyclyl". Exceptions are maximally unsaturated 6-membered rings containing O, S, SO and/or SO$_2$ as ring members, such as pyran and thiopyran, which are not aromatic). Partially unsaturated rings contain less than the maximum number of C—C and/or C—N and/or N—N double bond(s) allowed by the ring size. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6-, 7- or 8-membered saturated heteromonocyclic ring include: Oxiran-2-yl, thiiran-2-yl, aziridin-1-yl, aziridin-2-yl, oxetan-2-yl, oxetan-3-yl, thietan-2-yl, thietan-3-yl, 1-oxothietan-2-yl, 1-oxothietan-3-yl, 1,1-dioxothietan-2-yl, 1,1-dioxothietan-3-yl, azetidin-1-yl, azetidin-2-yl, azetidin-3-yl, tetrahydrofuran-2-yl, tetrahydrofuran-3-yl, tetrahydrothien-2-yl, tetrahydrothien-3-yl, 1-oxotetrahydrothien-2-yl, 1,1-dioxotetrahydrothien-2-yl, 1-oxotetrahydrothien-3-yl, 1,1-dioxotetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-2-yl, 1,2,4-oxadiazolidin-3-yl, 1,2,4-oxadiazolidin-4-yl, 1,2,4-oxadiazolidin-5-yl, 1,2,4-thiadiazolidin-2-yl, 1,2,4-thiadiazolidin-3-yl, 1,2,4-thiadiazolidin-4-yl, 1,2,4-thiadiazolidin-5-yl, 1,2,4-triazolidin-1-yl, 1,2,4-triazolidin-3-yl, 1,2,4-triazolidin-4-yl, 1,3,4-oxadiazolidin-2-yl, 1,3,4-oxadiazolidin-3-yl, 1,3,4-thiadiazolidin-2-yl, 1,3,4-thiadiazolidin-3-yl, 1,3,4-triazolidin-1-yl, 1,3,4-triazolidin-2-yl, 1,3,4-triazolidin-3-yl, tetrahydropyran-2-yl, tetrahydropyran-3-yl, tetrahydropyran-4-yl, 1,3-dioxan-2-yl, 1,3-dioxan-4-yl, 1,3-dioxan-5-yl, 1,4-dioxan-2-yl, piperidin-1-yl, piperidin-2-yl, piperidin-3-yl, piperidin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl, 1,2,4-hexahydrotriazin-1-yl, 1,2,4-hexahydrotriazin-2-yl, 1,2,4-hexahydrotriazin-3-yl, 1,2,4-hexahydrotriazin-4-yl, 1,2,4-hexahydrotriazin-5-yl, 1,2,4-hexahydrotriazin-6-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl, oxocane, thiocane, azocanyl, [1,3]diazocanyl, [1,4]diazocanyl, [1,5]diazocanyl, [1,5]oxazocanyl and the like.

Examples of a 3-, 4-, 5-, 6-, 7- or 8-membered partially unsaturated heteromonocyclic ring include: 2,3-dihydrofuran-2-yl, 2,3-dihydrofuran-3-yl, 2,4-dihydrofuran-2-yl, 2,4-dihydrofuran-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl, tetrahydro-1,4-dioxepinyl, 1,2,3,4,5,6-hexahydroazocine, 2,3,4,5,6,7-hexahydroazocine, 1,2,3,4,5,8-hexahydroazocine, 1,2,3,4,7,8-hexahydroazocine, 1,2,3,4,5,6-hexahydro-[1,5]diazocine,1,2,3,4,7,8-hexahydro-[1,5]diazocine and the like.

Examples of a 3-, 4-, 5-, 6-, 7- or 8-membered maximally unsaturated (including aromatic) heteromonocyclic ring are 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, pyran-2-yl, pyran-3-yl, pyran-4-yl, thiopyran-2-yl, thiopryan-3-yl, thiopryan-4-yl, 1-oxothiopryan-2-yl, 1-oxothiopryan-3-yl, 1-oxothiopryan-4-yl, 1,1-dioxothiopryan-2-yl, 1,1-dioxothiopryan-3-yl, 1,1-dioxothiopryan-4-yl, 2H-oxazin-2-yl, 2H-oxazin-3-yl, 2H-oxazin-4-yl, 2H-oxazin-5-yl, 2H-oxazin-6-yl, 4H-oxazin-3-yl, 4H-oxazin-4-yl, 4H-oxazin-5-yl, 4H-oxazin-6-yl, 6H-oxazin-3-yl, 6H-oxazin-4-yl, 7H-oxazin-5-yl, 8H-oxazin-6-yl, 2H-1,3-oxazin-2-yl, 2H-1,3-oxazin-4-yl, 2H-1,3-oxazin-5-yl, 2H-1,3-oxazin-6-yl, 4H-1,3-oxazin-2-yl, 4H-1,3-oxazin-4-yl, 4H-1,3-oxazin-5-yl, 4H-1,3-oxazin-6-yl, 6H-1,3-oxazin-2-yl, 6H-1,3-oxazin-4-yl, 6H-1,3-oxazin-5-yl, 6H-1,3-oxazin-6-yl, 2H-1,4-oxazin-2-yl, 2H-1,4-oxazin-3-yl, 2H-1,4-oxazin-5-yl, 2H-1,4-oxazin-6-yl, 4H-1,4-oxazin-2-yl, 4H-1,4-oxazin-3-yl, 4H-1,4-oxazin-4-yl, 4H-1,4-oxazin-5-yl, 4H-1,4-oxazin-6-yl, 6H-1,4-oxazin-2-yl, 6H-1,4-oxazin-3-yl, 6H-1,4-oxazin-5-yl, 6H-1,4-oxazin-6-yl, 1,4-dioxine-2-yl, 1,4-oxathiin-2-yl, 1H-azepine, 1H-[1,3]-diazepine, 1H[1,4]-diazepine, [1,3]diazocine, [1,5]diazocine, [1,5]diazocine and the like.

Examples for 5- or 6-membered monocyclic heteroaromatic rings containing 1, 2, 3 or 4 heteroatoms selected from the group consisting of N, O and S as ring members are 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl and the like.

Examples for 9- or 10-membered bicyclic heteroaromatic rings containing 1, 2, 3 or 4 heteroatoms selected from the group consisting of N, O and S as ring members are the following structures:

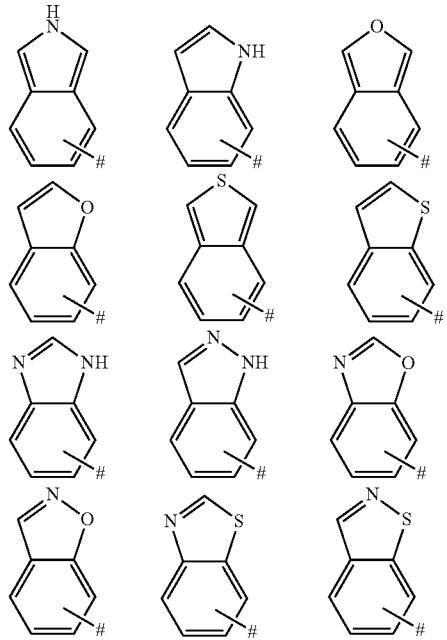

-continued

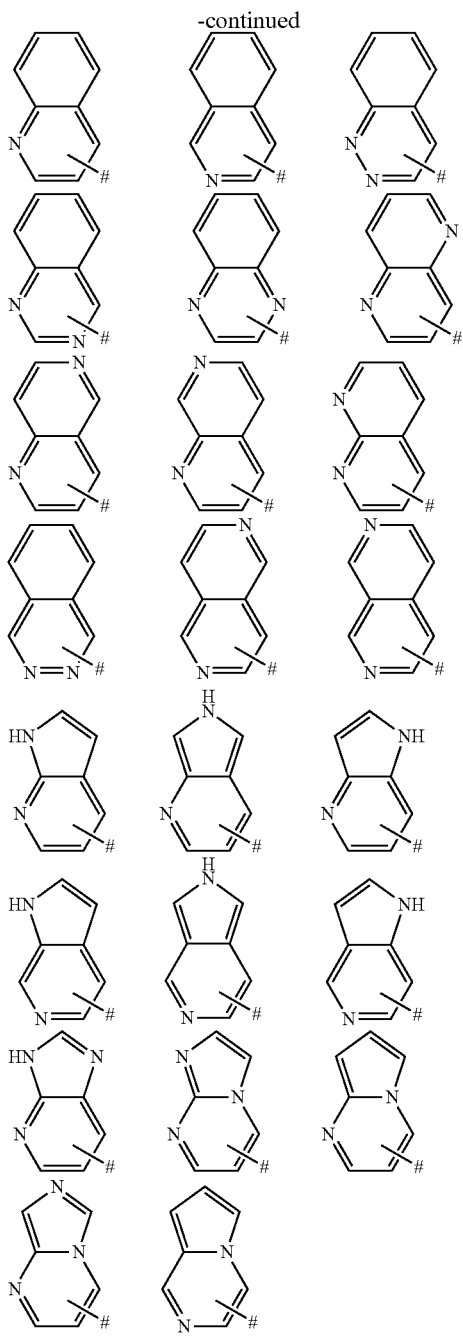

In the above structures, # denotes the attachment point to the remainder of the molecule. The attachment point may be at either one of the two fused rings and may be on a carbon or a nitrogen ring atom. If the rings carry one or more substituents, these may be bound to a carbon or a nitrogen ring atom and to any one of the two rings.

If $R^8$ and $R^9$, together with the nitrogen atom they are bound to, form a 3-, 4-, 5-, 6- 7- or 8-membered saturated heterocyclic ring which may contain 1, 2 or 3 additional heteroatoms or heteroatom groups selected from the group consisting of N, O, S, NO, S(O) and S(O)$_2$, this is for example aziridin-1-yl, azetidin-1-yl, pyrrolidin-1-yl, pyrazolidin-1-yl, imidazolodin-1-yl, oxazolidin-3-yl, isoxazolidin-2-yl, thiazolidin-3-yl, 1-oxothiazolidin-3-yl, 1,1-dioxothiazolidin-3-yl, isothiazolidin-2-yl, 1-oxoisothiazolidin-2-yl, 1,1-dioxoisothiazolidin-3-yl, piperidine-1-yl, piperazin-1-yl, hexahydropyridazin-1-yl, hexahydropyrimidin-1-yl, morpholin-4-yl (morpholino), thiomorpholin-4-yl, 1-oxothiomorpholin-4-yl, 1,1-diooxothiomorpholin-4-yl, azepan-1-yl, 1,2-diazepan-1-yl, 1,3-diazepan-1-yl, 1,4-diazepan-1-yl, azocan-1-yl, 1,2-diazocan-1-yl, 1,3-diazocan-1-yl, 1,4-diazocan-1-yl and the like.

The remarks made above and in the following with respect to preferred aspects of the invention, e.g. to preferred meanings of the variables L, $R^1$, $R^2$, $R^3$, $R^4$, $R^5$, $R^6$, $R^7$, $R^8$, $R^9$, $R^a$, $R^b$ and m of compounds I, to preferred compounds I and to preferred embodiments of the methods or the use according to the invention, apply in each case on their own or in particular to combinations thereof.

In one embodiment of the invention (embodiment 1), $R^1$ is $R^a$.

In an alternative embodiment of the invention (embodiment 2), $R^1$ is selected from the group consisting of halogen, $C_1$-$C_2$-haloalkyl, $C_1$-$C_2$-alkoxy, $C_1$-$C_2$-haloalkoxy, an N-bound saturated 3-, 4-, 5-, 6-, 7- or 8-membered heteromonocyclic ring containing one or two nitrogen atoms as ring members; and an N-bound saturated 7-, 8-, 9-, 10-, 11- or 12-membered heterobicyclic ring containing one or two nitrogen atoms as ring members; where the heteromonocyclic ring and the heterobicyclic ring may carry one or more substituents $R^4$. Simultaneously the phenyl, naphthyl, monocyclic or bicyclic heteroaromatic ring $R^2$ carries one substituent $R^a$ and optionally also one or more substituents $R^5$, where $R^a$, $R^4$ and $R^5$ have one of the above general or, in particular, one of the below preferred meanings.

In a particular embodiment of embodiment 2 (embodiment 2.1), $R^1$ is halogen, and is specifically a fluorine atom (embodiment 2.1.1); and simultaneously the phenyl, naphthyl, monocyclic or bicyclic heteroaromatic ring $R^2$ carries one substituent $R^a$ and optionally also one or more substituents $R^5$, where $R^a$ and $R^5$ have one of the above general or, in particular, one of the below preferred meanings.

In an alternative particular embodiment of embodiment 2 (embodiment 2.2), $R^1$ is an N-bound saturated 3-, 4-, 5-, 6-, 7- or 8-membered heteromonocyclic ring containing one or two nitrogen atoms as ring members; or an N-bound saturated 7-, 8-, 9-, 10-, 11- or 12-membered heterobicyclic ring containing one or two nitrogen atoms as ring members; where the heteromonocyclic ring and the heterobicyclic ring may carry one or more substituents $R^4$; and simultaneously the phenyl, naphthyl, monocyclic or bicyclic heteroaromatic ring $R^2$ carries one substituent $R^a$ and optionally also one or more substituents $R^5$, where $R^a$, $R^4$ and $R^5$ have one of the above general or, in particular, one of the below preferred meanings.

In a specific embodiment of embodiment 2.2 (embodiment 2.2.1), $R^1$ is an N-bound saturated 7-, 8-, 9-, 10- or 11-membered heterobicyclic ring containing one or two nitrogen atoms as ring members; where the heterobicyclic ring may carry one or more substituents $R^4$; and simultaneously the phenyl, naphthyl, monocyclic or bicyclic heteroaromatic ring $R^2$ carries one substituent $R^a$ and optionally also one or more substituents $R^5$, where $R^a$, $R^4$ and $R^5$ have one of the above general or, in particular, one of the below preferred meanings.

In particular (embodiment 3), $R^a$ is an N-bound saturated 3-, 4-, 5-, 6-, 7- or 8-membered heteromonocyclic ring containing one nitrogen atom as ring member, where the heteromonocyclic ring carries 1, 2 or 3 substituents $R^b$ and optionally 1 or 2 further substituents $R^4$, where $R^b$ and $R^4$ have one of the above general or, in particular, one of the below preferred meanings. More particularly (embodiment 3.1), $R^a$ is an N-bound saturated 3-, 4-, 5-, 6-, 7- or 8-membered heteromonocyclic ring containing one nitrogen atom as ring member, where the heteromonocyclic ring carries 1, 2 or 3 substituents $R^b$ and optionally 1 or 2 further substituents $R^4$, where $R^b$ and $R^4$ have one of the above general or, in particular, one of the below preferred meanings, and $R^1$ is as defined in any of embodiments 1, 2, 2.1, 2.1.1, 2.2 or 2.2.1.

Specifically (embodiment 3.2), $R^a$ is an N-bound saturated 4-, 5- or 6-membered heteromonocyclic ring containing one nitrogen atom as ring member, where the heteromonocyclic ring carries 1 or 2 substituents $R^b$ and optionally one further substituent $R^4$, where $R^b$ and $R^4$ have one of the above general or, in particular, one of the below preferred meanings. More specifically (embodiment 3.2.1), $R^a$ is an N-bound saturated 4-, 5- or 6-membered heteromonocyclic ring containing one nitrogen atom as ring member, where the heteromonocyclic ring carries 1 or 2 substituents $R^b$ and optionally one further substituent $R^4$, where $R^b$ and $R^4$ have one of the above general or, in particular, one of the below preferred meanings, and $R^1$ is as defined in any of embodiments 1, 2, 2.1, 2.1.1, 2.2 or 2.2.1.

In another particular embodiment (embodiment 4), $R^a$ is an N-bound saturated 7-, 8-, 9-, 10-, 11- or 12-membered heterobicyclic ring containing one nitrogen atom as ring member, where the heterobicyclic ring carries 1, 2 or 3 substituents $R^b$ and optionally 1 or 2 further substituents $R^4$, where $R^b$ and $R^4$ have one of the above general or, in particular, one of the below preferred meanings. More particularly (embodiment 4.1), $R^a$ is an N-bound saturated 7-, 8-, 9-, 10-, 11- or 12-membered heterobicyclic ring containing one nitrogen atom as ring member, where the heterobicyclic ring carries 1, 2 or 3 substituents $R^b$ and optionally 1 or 2 further substituents $R^4$, where $R^b$ and $R^4$ have one of the above general or, in particular, one of the below preferred meanings, and $R^1$ is as defined in any of embodiments 1, 2, 2.1, 2.1.1, 2.2 or 2.2.1.

Specifically (embodiment 4.2), $R^a$ is an N-bound saturated 7-, 8-, 9- or 10-membered heterobicyclic ring containing one nitrogen atom as ring member, where the heterobicyclic ring carries 1 or 2 substituents $R^b$ and optionally one further substituent $R^4$, where $R^b$ and $R^4$ have one of the above general or, in particular, one of the below preferred meanings. More specifically (embodiment 4.2.1), $R^a$ is an N-bound saturated 7-, 8-, 9- or 10-membered heterobicyclic ring containing one nitrogen atom as ring member, where the heterobicyclic ring carries 1 or 2 substituents $R^b$ and optionally one further substituent $R^4$, where $R^b$ and $R^4$ have one of the above general or, in particular, one of the below preferred meanings, and $R^1$ is as defined in any of embodiments 1, 2, 2.1, 2.1.1, 2.2 or 2.2.1.

In a preferred embodiment (embodiment 5), the oxygen-containing radical $R^b$ is selected from the group consisting of hydroxyl (—OH), carboxyl (—C(O)OH), —CH$_2$—C(O)OH and —C(O)NH$_2$. In particular (embodiment 5.1), the oxygen-containing radical $R^b$ is selected from the group consisting of hydroxyl, —C(O)OH, —CH$_2$—C(O)OH and —C(O)NH$_2$, and $R^1$ and $R^a$ are as defined in any of embodiments 1, 2, 2.1, 2.1.1, 2.2, 2.2.1, 3, 3.1, 3.2, 3.2.1, 4, 4.1, 4.2 or 4.2.1.

Specifically (embodiment 5.2), the oxygen-containing radical $R^b$ is selected from the group consisting of hydroxyl, carboxyl and —C(O)NH$_2$. More specifically (embodiment 5.2.1), the oxygen-containing radical $R^b$ is selected from the group consisting of hydroxyl and carboxyl, and $R^1$ and $R^a$ are as defined in any of embodiments 1, 2, 2.1, 2.1.1, 2.2, 2.2.1, 3, 3.1, 3.2, 3.2.1, 4, 4.1, 4.2 or 4.2.1.

Even more specifically, (embodiment 5.3), the oxygen-containing radical $R^b$ is selected from the group consisting of hydroxyl and carboxyl. Very specifically (embodiment 5.3.1), the oxygen-containing radical $R^b$ is selected from the group consisting of hydroxyl and carboxyl, and $R^1$ and $R^a$ are as defined in any of embodiments 1, 2, 2.1, 2.1.1, 2.2, 2.2.1, 3, 3.1, 3.2, 3.2.1, 4, 4.1, 4.2 or 4.2.1.

In a preferred embodiment of embodiments 5.2, 5.2.1, 5.3 and 5.3.1, (embodiment 5.4), if $R^b$ is OH, $R^a$ carries 1 or 2 OH groups (and no other substituent $R^b$); if $R^b$ is COOH or —C(O)NH$_2$, $R^a$ carries one COOH group or one —C(O)NH$_2$ group (and no other substituent $R^b$), and if $R^b$ is —CH$_2$—C(O)OH, $R^a$ carries one —CH$_2$—C(O)OH group (and no other substituent $R^b$).

In a preferred embodiment (embodiment 6), each $R^4$ is independently selected from the group consisting of halogen, $C_1$-$C_4$-alkyl and $C_1$-$C_4$-haloalkyl. In particular (embodiment 6.1), each $R^4$ is independently selected from the group consisting of halogen, $C_1$-$C_4$-alkyl and $C_1$-$C_4$-haloalkyl, and $R^1$, $R^a$ and $R^b$ are as defined in any of embodiments 1, 2, 2.1, 2.1.1, 2.2, 2.2.1, 3, 3.1, 3.2, 3.2.1, 4, 4.1, 4.2, 4.2.1, 5, 5.1, 5.2, 5.2.1, 5.3, 5.3.1 or 5.4. Specifically, (embodiment 6.2), each $R^4$ is independently selected from the group consisting of halogen and $C_1$-$C_4$-alkyl. More specifically, (embodiment 6.2.1), each $R^4$ is independently selected from the group consisting of halogen and $C_1$-$C_4$-alkyl, and $R^1$, $R^a$ and $R^b$ are as defined in any of embodiments 1, 2, 2.1, 2.1.1, 2.2, 2.2.1, 3, 3.1, 3.2, 3.2.1, 4, 4.1, 4.2, 4.2.1, 5, 5.1, 5.2, 5.2.1, 5.3, 5.3.1 or 5.4. Even more specifically, (embodiment 6.2.1.1), each $R^4$ is independently F or methyl, and $R^1$, $R^a$ and $R^b$ are as defined in any of embodiments 1, 2, 2.1, 2.1.1, 2.2, 2.2.1, 3, 3.1, 3.2, 3.2.1, 4, 4.1, 4.2, 4.2.1, 5, 5.1, 5.2, 5.2.1, 5.3, 5.3.1 or 5.4.

In a preferred embodiment (embodiment 7), L is $S(O)_2$. In particular (embodiment 7.1), L is $S(O)_2$, and $R^1$, $R^a$, $R^b$ and $R^4$ are as defined in any of embodiments 1, 2, 2.1, 2.1.1, 2.2, 2.2.1, 3, 3.1, 3.2, 3.2.1, 4, 4.1, 4.2, 4.2.1, 5, 5.1, 5.2, 5.2.1, 5.3, 5.3.1, 5.4, 6, 6.1, 6.2, 6.2.1 or 6:2.1.1.

In a preferred embodiment (embodiment 8), $R^2$ is phenyl which may be substituted (or is substituted, if $R^1$ is not $R^a$) as defined above or below. In particular (embodiment 8.1), $R^2$ is phenyl which may be substituted (or is substituted, if $R^1$ is not $R^a$) as defined above or below, and $R^1$, $R^a$, $R^b$, $R^4$ and L are as defined in any of embodiments 1, 2, 2.1, 2.1.1, 2.2, 2.2.1, 3, 3.1, 3.2, 3.2.1, 4, 4.1, 4.2, 4.2.1, 5, 5.1, 5.2, 5.2.1, 5.3, 5.3.1, 5.4, 6, 6.1, 6.2, 6.2.1, 6.2.1.1, 7 or 7.1.

In a preferred embodiment (embodiment 9), each $R^5$ is independently selected from the group consisting of halogen, cyano, hydroxyl, $C_1$-$C_6$-alkyl, $C_1$-$C_6$-haloalkyl, $C_1$-$C_6$-alkoxy, $C_1$-$C_6$-haloalkoxy, COOH, CONH$_2$ and a 3-, 4-, 5-, 6-, 7- or 8-membered saturated heterocyclic ring containing 1, 2 or 3 heteroatoms or heteroatom groups selected from the group consisting of N, O, S, NO, S(O) and $S(O)_2$ as ring members, where heterocyclic ring may carry one or more substituents $R^7$; where each $R^7$ is independently selected from the group consisting of halogen, $C_1$-$C_6$-alkyl, $C_1$-$C_6$-haloalkyl, $C_1$-$C_6$-alkoxy and $C_1$-$C_6$-haloalkoxy. In particular (embodiment 9.1), each $R^5$ is independently selected from the group consisting of halogen, cyano, hydroxyl, $C_1$-$C_6$-alkyl, $C_1$-$C_6$-haloalkyl, $C_1$-$C_6$-alkoxy, $C_1$-$C_6$-haloalkoxy, COOH, CONH$_2$ and a 3-, 4-, 5-, 6-, 7- or 8-membered saturated heterocyclic ring containing 1, 2 or 3 heteroatoms or heteroatom groups selected from the group consisting of N, O, S, NO, S(O) and $S(O)_2$ as ring members, where the heterocyclic ring may carry one or more substituents $R^7$;

where each R⁷ is independently selected from the group consisting of halogen, $C_1$-$C_6$-alkyl, $C_1$-$C_6$-haloalkyl, $C_1$-$C_6$-alkoxy and $C_1$-$C_6$-haloalkoxy, and $R^1$, $R^a$, $R^b$, $R^4$, L and $R^2$ are as defined in any of embodiments 1, 2, 2.1, 2.1.1, 2.2, 2.2.1, 3, 3.1, 3.2, 3.2.1, 4, 4.1, 4.2, 4.2.1, 5, 5.1, 5.2, 5.2.1, 5.3, 5.3.1, 5.4, 6, 6.1, 6.2, 6.2.1, 6.2.1.1, 7, 7.1, 8 or 8.1. In a specific embodiment (embodiment 9.2), each $R^5$ is independently selected from the group consisting of halogen, cyano, hydroxyl, $C_1$-$C_6$-alkyl, $C_1$-$C_6$-haloalkyl, $C_1$-$C_6$-alkoxy, $C_1$-$C_6$-haloalkoxy, and a 3-, 4-, 5-, 6-, 7- or 8-membered saturated heterocyclic ring containing 1, 2 or 3 heteroatoms or heteroatom groups selected from the group consisting of N, O, S, NO, S(O) and S(O)₂ as ring members, where heterocyclic ring may carry one or more substituents R⁷; where each R⁷ is independently selected from the group consisting of halogen, $C_1$-$C_6$-alkyl and $C_1$-$C_6$-haloalkyl. More specifically (embodiment 9.2.1), each $R^5$ is independently selected from the group consisting of halogen, cyano, hydroxyl, $C_1$-$C_6$-alkyl, $C_1$-$C_6$-haloalkyl, $C_1$-$C_6$-alkoxy, $C_1$-$C_6$-haloalkoxy, and a 3-, 4-, 5-, 6-, 7- or 8-membered saturated heterocyclic ring containing 1, 2 or 3 heteroatoms or heteroatom groups selected from the group consisting of N, O, S, NO, S(O) and S(O)₂ as ring members, where the heterocyclic ring may carry one or more substituents R⁷; where each R⁷ is independently selected from the group consisting of halogen, $C_1$-$C_6$-alkyl and $C_1$-$C_6$-haloalkyl, and $R^1$, $R^a$, $R^b$, $R^4$, L and $R^2$ are as defined in any of embodiments 1, 2, 2.1, 2.1.1, 2.2, 2.2.1, 3, 3.1, 3.2, 3.2.1, 4, 4.1, 4.2, 4.2.1, 5, 5.1, 5.2, 5.2.1, 5.3, 5.3.1, 5.4, 6, 6.1, 6.2, 6.2.1, 6.2.1.1, 7, 7.1, 8 or 8.1.

The 3-, 4-, 5-, 6-, 7- or 8-membered saturated heterocyclic ring $R^5$ containing 1, 2 or 3 heteroatoms or heteroatom groups selected from the group consisting of N, O, S, NO, S(O) and S(O)₂ as ring members is preferably a 5- or 6-membered saturated heterocyclic ring containing 1 or 2 nitrogen atoms as ring members, where the heterocyclic ring may carry one or more substituents R⁷; where each R⁷ is independently selected from the group consisting of halogen, $C_1$-$C_6$-alkyl, $C_1$-$C_6$-haloalkyl, $C_1$-$C_6$-alkoxy and $C_1$-$C_6$-haloalkoxy, and is in particular $C_1$-$C_4$-alkyl or $C_1$-$C_4$-alkoxy.

In a preferred embodiment (embodiment 10), m is 0. In particular (embodiment 10.1), m is 0 and $R^1$, $R^a$, $R^b$, $R^4$, L, $R^2$ and $R^5$ are as defined in any of embodiments 1, 2, 2.1, 2.1.1, 2.2, 2.2.1, 3, 3.1, 3.2, 3.2.1, 4, 4.1, 4.2, 4.2.1, 5, 5.1, 5.2, 5.2.1, 5.3, 5.3.1, 5.4, 6, 6.1, 6.2, 6.2.1, 6.2.1.1, 7, 7.1, 8, 8.1, 9 or 9.1.

In particular, the compound I is a compound of formula I.1

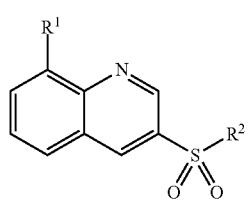

(I.1)

where $R^1$ and $R^2$ have one of the above general or, in particular, one of the above preferred definitions.
Specifically, in compounds I.1,
$R^1$ is $R^a$, which is in turn an N-bound saturated heterocyclic ring selected from the group consisting of azetidin-1-yl, pyrrolidin-1-yl and piperidin-1-yl, where the ring carries one or two substituents $R^b$ which have one of the above general or, in particular, one of the above preferred definitions and are in particular OH, COOH, CONH₂ or —CH₂—COOH and are specifically OH, COOH or CONH₂ and are very specifically OH or COOH, and carries optionally one or two substituents $R^4$ which have one of the above general or, in particular, one of the above preferred definitions; and $R^2$ is phenyl which may be substituted by 1 or 2 substituents selected from the group consisting of halogen, cyano, hydroxyl, $C_1$-$C_6$-alkyl, $C_1$-$C_6$-haloalkyl, $C_1$-$C_6$-alkoxy, $C_1$-$C_6$-haloalkoxy, COOH, CONH₂ and an N-bound saturated heterocyclic ring selected from the group consisting of azetidin-1-yl, pyrrolidin-1-yl, piperidine-1-yl and piperazin-1-yl, where the ring carries one or two substituents selected from the group consisting of $C_1$-$C_6$-alkyl, $C_1$-$C_6$-haloalkyl, $C_1$-$C_6$-alkoxy, OH and COOH, where $R^2$ is in particular phenyl which may be substituted by 1 or 2 substituents selected from the group consisting of halogen, cyano, hydroxyl, $C_1$-$C_6$-alkyl, $C_1$-$C_6$-haloalkyl, $C_1$-$C_6$-alkoxy, $C_1$-$C_6$-haloalkoxy, and an N-bound saturated heterocyclic ring selected from the group consisting of azetidin-1-yl, pyrrolidin-1-yl and piperidine-1-yl, where the heterocyclic ring carries one or two substituents selected from the group consisting of $C_1$-$C_6$-alkyl, $C_1$-$C_6$-haloalkyl, OH and COOH.

More specifically, in compounds I.1,
$R^1$ is $R^a$, which is in turn an N-bound saturated heterocyclic ring selected from azetidin-1-yl, pyrrolidin-1-yl and piperidine-1-yl, where the ring carries one or two OH groups or one COOH group or one CONH₂ group or one —CH₂—COOH group, and carries optionally one or two substituents $R^4$ selected from the group consisting of F, CH₃, CHF₂ and CF₃; and $R^2$ is phenyl which may be substituted by 1 or 2 substituents selected from the group consisting of halogen, cyano, hydroxyl, $C_1$-$C_6$-alkyl, $C_1$-$C_6$-haloalkyl, $C_1$-$C_6$-alkoxy, COOH, CONH₂ and an N-bound saturated heterocyclic ring selected from the group consisting of azetidin-1-yl, pyrrolidin-1-yl, piperidin-1-yl and piperazin-1-yl, where the heterocyclic ring carries one or two substituents selected from the group consisting of $C_1$-$C_6$-alkyl, $C_1$-$C_6$-haloalkyl, $C_1$-$C_6$-alkoxy, OH and COOH and in particular selected from the group consisting of $C_1$-$C_6$-alkyl, $C_1$-$C_6$-alkoxy, OH and COOH.

Even more specifically, in compounds I.1,
$R^1$ is $R^a$, which is in turn an N-bound saturated heterocyclic ring selected from azetidin-1-yl, pyrrolidin-1-yl and piperidine-1-yl, where the ring carries one or two OH groups or one COOH or one CONH₂ group, and carries optionally one or two substituents $R^4$ selected from the group consisting of F, CH₃, CHF₂ and CF₃; and $R^2$ is phenyl which may be substituted by 1 or 2 substituents selected from the group consisting of halogen, cyano, hydroxyl, $C_1$-$C_6$-alkyl, $C_1$-$C_6$-haloalkyl, $C_1$-$C_6$-alkoxy, and an N-bound saturated heterocyclic ring selected from the group consisting of azetidin-1-yl, pyrrolidin-1-yl and piperidin-1-yl, where the heterocyclic ring carries one or two substituents selected from the group consisting of $C_1$-$C_6$-alkyl, $C_1$-$C_6$-haloalkyl, OH and COOH.

Very specifically, in compounds I.1,
$R^1$ is $R^a$, which is in turn an N-bound saturated heterocyclic ring selected from azetidin-1-yl, pyrrolidin-1-yl and piperidine-1-yl, where the ring carries one or two OH groups or one COOH group, and carries optionally one methyl substituent; and R² is phenyl which may be substituted by 1 or 2 substituents selected from the group consisting of halogen, hydroxyl, $C_1$-$C_6$-alkyl, $C_1$-$C_6$-haloalkyl, $C_1$-$C_6$-alkoxy, and an N-bound saturated heterocyclic ring selected from the group consisting of azetidin-1-yl, pyrrolidin-1-yl and piperidin-1-yl, where the heterocyclic ring carries one or two substituents selected from the group consisting of OH and COOH.

In another specific embodiment, in compounds I.1,
R¹ is F; and
R² is phenyl which carries one ring $R^a$, which is in turn an N-bound saturated heterocyclic ring selected from the group consisting of azetidin-1-yl, pyrrolidin-1-yl and piperidine-1-yl, where the heterocyclic ring carries one or two substituents $R^b$ which have one of the above general or, in particular, one of the above preferred definitions and are in particular OH or COOH, and carries optionally one or two substituents $R^4$ which have one of the above general or, in particular, one of the above preferred definitions; where the phenyl ring may additionally carry 1 or 2 substituents selected from the group consisting of halogen, cyano, hydroxyl, $C_1$-$C_6$-alkyl, $C_1$-$C_6$-haloalkyl and $C_1$-$C_6$-alkoxy.

In another more specific embodiment, in compounds I.1,
R¹ is F; and
R² is phenyl which carries one ring $R^a$, which is in turn an N-bound saturated heterocyclic ring selected from the group consisting of azetidin-1-yl, pyrrolidin-1-yl and piperidine-1-yl, where the heterocyclic ring carries one or two OH groups or one COOH group, and carries optionally one or two substituents $R^4$ selected from the group consisting of F, $CH_3$, $CHF_2$ and $CF_3$.

Examples of preferred compounds are compounds of the following formulae I.a to I.g and the stereoisomers thereof, where R¹ has one of the general or preferred meanings given above, $R^{5a}$ is $R^5$ and/or $R^a$ and n is 0, 1, 2, 3, 4 or 5. Examples of preferred compounds are the individual compounds compiled in the tables 1 to 525 below. Moreover, the meanings mentioned below for the individual variables in the tables are per se, independently of the combination in which they are mentioned, a particularly preferred embodiment of the substituents in question.

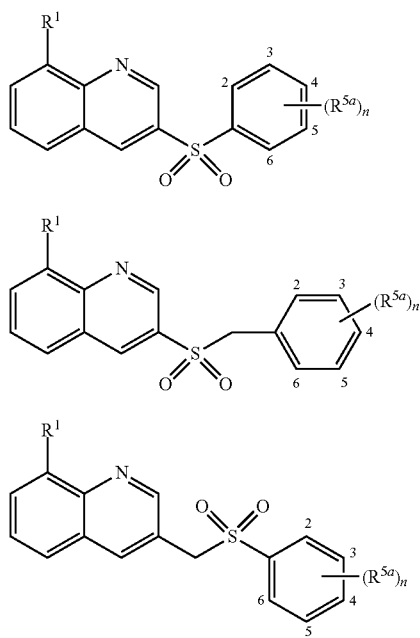

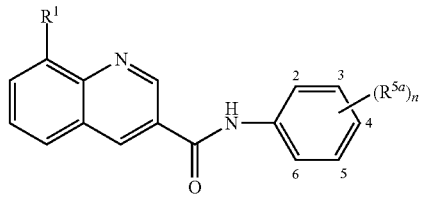
I.d

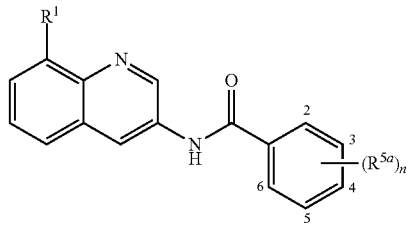
I.e

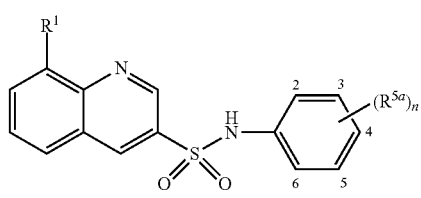
I.f

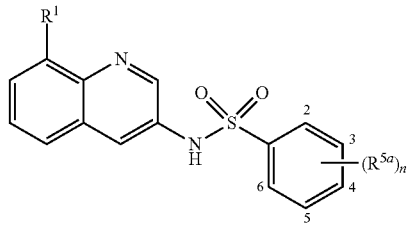
I.g

Table 1
Compounds of the formula I.a in which R¹ is ring $R^a$.1 and $(R^{5a})_n$ for a compound corresponds in each case to one row of Table A Table 2
Compounds of the formula I.a in which R¹ is ring $R^a$.2 and $(R^{5a})_n$ for a compound corresponds in each case to one row of Table A Table 3
Compounds of the formula I.a in which R¹ is ring $R^a$.3 and $(R^{5a})_n$ for a compound corresponds in each case to one row of Table A Table 4
Compounds of the formula I.a in which R¹ is ring $R^a$.4 and $(R^{5a})_n$ for a compound corresponds in each case to one row of Table A Table 5
Compounds of the formula I.a in which R¹ is ring $R^a$.5 and $(R^{5a})_n$ for a compound corresponds in each case to one row of Table A Table 6
Compounds of the formula I.a in which R¹ is ring $R^a$.6 and $(R^{5a})_n$ for a compound corresponds in each case to one row of Table A Table 7
Compounds of the formula I.a in which R¹ is ring $R^a$.7 and $(R^{5a})_n$ for a compound corresponds in each case to one row of Table A Table 8
Compounds of the formula I.a in which R¹ is ring $R^a$.8 and $(R^{5a})_n$ for a compound corresponds in each case to one row of Table A Table 9
Compounds of the formula I.a in which $R^1$ is ring $R^a.9$ and $(R^{5a})_n$ for a compound corresponds in each case to one row of Table A Table 10
Compounds of the formula I.a in which $R^1$ is ring $R^a.10$ and $(R^{5a})_n$ for a compound corresponds in each case to one row of Table A Table 11
Compounds of the formula I.a in which $R^1$ is ring $R^a.11$ and $(R^{5a})_n$ for a compound corresponds in each case to one row of Table A Table 12
Compounds of the formula I.a in which $R^1$ is ring $R^a.12$ and $(R^{5a})_n$ for a compound corresponds in each case to one row of Table A Table 13
Compounds of the formula I.a in which $R^1$ is ring $R^a.13$ and $(R^{5a})_n$ for a compound corresponds in each case to one row of Table A Table 14
Compounds of the formula I.a in which $R^1$ is ring $R^a.14$ and $(R^{5a})_n$ for a compound corresponds in each case to one row of Table A Table 15
Compounds of the formula I.a in which $R^1$ is ring $R^a.15$ and $(R^{5a})_n$ for a compound corresponds in each case to one row of Table A Table 16
Compounds of the formula I.a in which $R^1$ is ring $R^a.16$ and $(R^{5a})_n$ for a compound corresponds in each case to one row of Table A Table 17
Compounds of the formula I.a in which $R^1$ is ring $R^a.17$ and $(R^{5a})_n$ for a compound corresponds in each case to one row of Table A Table 18
Compounds of the formula I.a in which $R^1$ is ring $R^a.18$ and $(R^{5a})_n$ for a compound corresponds in each case to one row of Table A Table 19
Compounds of the formula I.a in which $R^1$ is ring $R^a.19$ and $(R^{5a})_n$ for a compound corresponds in each case to one row of Table A Table 20
Compounds of the formula I.a in which $R^1$ is ring $R^a.20$ and $(R^{5a})_n$ for a compound corresponds in each case to one row of Table A Table 21
Compounds of the formula I.a in which $R^1$ is ring $R^a.21$ and $(R^{5a})_n$ for a compound corresponds in each case to one row of Table A Table 22
Compounds of the formula I.a in which $R^1$ is ring $R^a.22$ and $(R^{5a})_n$ for a compound corresponds in each case to one row of Table A Table 23
Compounds of the formula I.a in which $R^1$ is ring $R^a.23$ and $(R^{5a})_n$ for a compound corresponds in each case to one row of Table A Table 24
Compounds of the formula I.a in which $R^1$ is ring $R^a.24$ and $(R^{5a})_n$ for a compound corresponds in each case to one row of Table A Table 25
Compounds of the formula I.a in which $R^1$ is ring $R^a.25$ and $(R^{5a})_n$ for a compound corresponds in each case to one row of Table A Table 26
Compounds of the formula I.a in which $R^1$ is ring $R^a.26$ and $(R^{5a})_n$ for a compound corresponds in each case to one row of Table A Table 27
Compounds of the formula I.a in which $R^1$ is ring $R^a.27$ and $(R^{5a})_n$ for a compound corresponds in each case to one row of Table A Table 28
Compounds of the formula I.a in which $R^1$ is ring $R^a.28$ and $(R^{5a})_n$ for a compound corresponds in each case to one row of Table A Table 29
Compounds of the formula I.a in which $R^1$ is ring $R^a.29$ and $(R^{5a})_n$ for a compound corresponds in each case to one row of Table A Table 30
Compounds of the formula I.a in which $R^1$ is ring $R^a.30$ and $(R^{5a})_n$ for a compound corresponds in each case to one row of Table A Table 31
Compounds of the formula I.a in which $R^1$ is ring $R^a.31$ and $(R^{5a})_n$ for a compound corresponds in each case to one row of Table A Table 32
Compounds of the formula I.a in which $R^1$ is ring $R^a.32$ and $(R^{5a})_n$ for a compound corresponds in each case to one row of Table A Table 33
Compounds of the formula I.a in which $R^1$ is ring $R^a.33$ and $(R^{5a})_n$ for a compound corresponds in each case to one row of Table A Table 34
Compounds of the formula I.a in which $R^1$ is ring $R^a.34$ and $(R^{5a})_n$ for a compound corresponds in each case to one row of Table A Table 35
Compounds of the formula I.a in which $R^1$ is ring $R^a.35$ and $(R^{5a})_n$ for a compound corresponds in each case to one row of Table A Table 36
Compounds of the formula I.a in which $R^1$ is ring $R^a.36$ and $(R^{5a})_n$ for a compound corresponds in each case to one row of Table A Table 37
Compounds of the formula I.a in which $R^1$ is ring $R^a.37$ and $(R^{5a})_n$ for a compound corresponds in each case to one row of Table A Table 38
Compounds of the formula I.a in which $R^1$ is ring $R^a.38$ and $(R^{5a})_n$ for a compound corresponds in each case to one row of Table A Table 39
Compounds of the formula I.a in which $R^1$ is ring $R^a.39$ and $(R^{5a})_n$ for a compound corresponds in each case to one row of Table A Table 40
Compounds of the formula I.a in which $R^1$ is ring $R^a.40$ and $(R^{5a})_n$ for a compound corresponds in each case to one row of Table A Table 41
Compounds of the formula I.a in which $R^1$ is ring $R^a.41$ and $(R^{5a})_n$ for a compound corresponds in each case to one row of Table A
Table 42
Compounds of the formula I.a in which $R^1$ is ring $R^a.42$ and $(R^{5a})_n$ for a compound corresponds in each case to one row of Table A
Table 43
Compounds of the formula I.a in which $R^1$ is ring $R^a.43$ and $(R^{5a})_n$ for a compound corresponds in each case to one row of Table A
Table 44
Compounds of the formula I.a in which $R^1$ is ring $R^a.44$ and $(R^{5a})_n$ for a compound corresponds in each case to one row of Table A
Table 45
Compounds of the formula I.a in which $R^1$ is ring $R^a.45$ and $(R^{5a})_n$ for a compound corresponds in each case to one row of Table A
Table 46
Compounds of the formula I.a in which $R^1$ is ring $R^a.46$ and $(R^{5a})_n$ for a compound corresponds in each case to one row of Table A
Table 47
Compounds of the formula I.a in which $R^1$ is ring $R^a.47$ and $(R^{5a})_n$ for a compound corresponds in each case to one row of Table A
Table 48
Compounds of the formula I.a in which $R^1$ is ring $R^a.48$ and $(R^{5a})_n$ for a compound corresponds in each case to one row of Table A
Table 49
Compounds of the formula I.a in which $R^1$ is ring $R^a.49$ and $(R^{5a})_n$ for a compound corresponds in each case to one row of Table A
Table 50
Compounds of the formula I.a in which $R^1$ is ring $R^a.50$ and $(R^{5a})_n$ for a compound corresponds in each case to one row of Table A
Table 51
Compounds of the formula I.a in which $R^1$ is ring $R^a.51$ and $(R^{5a})_n$ for a compound corresponds in each case to one row of Table A
Table 52
Compounds of the formula I.a in which $R^1$ is ring $R^a.52$ and $(R^{5a})_n$ for a compound corresponds in each case to one row of Table A
Table 53
Compounds of the formula I.a in which $R^1$ is ring $R^a.53$ and $(R^{5a})_n$ for a compound corresponds in each case to one row of Table A
Table 54
Compounds of the formula I.a in which $R^1$ is ring $R^a.54$ and $(R^{5a})_n$ for a compound corresponds in each case to one row of Table A
Table 55
Compounds of the formula I.a in which $R^1$ is ring $R^a.55$ and $(R^{5a})_n$ for a compound corresponds in each case to one row of Table A
Table 56
Compounds of the formula I.a in which $R^1$ is ring $R^a.56$ and $(R^{5a})_n$ for a compound corresponds in each case to one row of Table A
Table 57
Compounds of the formula I.a in which $R^1$ is ring $R^a.57$ and $(R^{5a})_n$ for a compound corresponds in each case to one row of Table A
Table 58
Compounds of the formula I.a in which $R^1$ is ring $R^a.58$ and $(R^{5a})_n$ for a compound corresponds in each case to one row of Table A
Table 59
Compounds of the formula I.a in which $R^1$ is ring $R^a.59$ and $(R^{5a})_n$ for a compound corresponds in each case to one row of Table A
Table 60
Compounds of the formula I.a in which $R^1$ is ring $R^a.60$ and $(R^{5a})_n$ for a compound corresponds in each case to one row of Table A
Table 61
Compounds of the formula I.a in which $R^1$ is F and $(R^{5a})_n$ for a compound corresponds in each case to one row of Table B
Table 62
Compounds of the formula I.a in which $R^1$ is Cl and $(R^{5a})_n$ for a compound corresponds in each case to one row of Table B
Table 63
Compounds of the formula I.a in which $R^1$ is $CHF_2$ and $(R^{5a})_n$ for a compound corresponds in each case to one row of Table B
Table 64
Compounds of the formula I.a in which $R^1$ is $CF_3$ and $(R^{5a})_n$ for a compound corresponds in each case to one row of Table B
Table 65
Compounds of the formula I.a in which $R^1$ is $OCF_3$ and $(R^{5a})_n$ for a compound corresponds in each case to one row of Table B
Table 66
Compounds of the formula I.a in which $R^1$ is $OCHF_2$ and $(R^{5a})_n$ for a compound corresponds in each case to one row of Table B
Table 67
Compounds of the formula I.a in which $R^1$ is $OCF_3$ and $(R^{5a})_n$ for a compound corresponds in each case to one row of Table B
Table 68
Compounds of the formula I.a in which $R^1$ is azetidin-1-yl and $(R^{5a})_n$ for a compound corresponds in each case to one row of Table B
Table 69
Compounds of the formula I.a in which $R^1$ is pyrrolidin-1-yl and $(R^{5a})_n$ for a compound corresponds in each case to one row of Table B
Table 70
Compounds of the formula I.a in which $R^1$ is piperidine-1-yl and $(R^{5a})_n$ for a compound corresponds in each case to one row of Table B
Table 71
Compounds of the formula I.a in which $R^1$ is piperazine-1-yl and $(R^{5a})_n$ for a compound corresponds in each case to one row of Table B
Table 72
Compounds of the formula I.a in which $R^1$ is 1-methyl-piperazine-4-yl and $(R^{5a})_n$ for a compound corresponds in each case to one row of Table B Table 73
Compounds of the formula I.a in which $R^1$ is octahydro-isoindol-2-yl and $(R^{5a})_n$ for a compound corresponds in each case to one row of Table B Table 74
Compounds of the formula I.a in which $R^1$ is octahydro-pyrrolo[3,4-c]pyridine-2-yl and $(R^{5a})_n$ for a compound corresponds in each case to one row of Table B Table 75
Compounds of the formula I.a in which $R^1$ is 5-methyl-octahydro-pyrrolo[3,4-c]pyridine-2-yl and $(R^{5a})_n$ for a compound corresponds in each case to one row of Table B Tables 76 to 150
Compounds of the formula I.b in which $R^1$ and $(R^{5a})_n$ are as defined in any one of tables 1 to 75.

Tables 151 to 225
Compounds of the formula I.c in which $R^1$ and $(R^{5a})_n$ are as defined in any one of tables 1 to 75.

Tables 226 to 300
Compounds of the formula I.d in which $R^1$ and $(R^{5a})_n$ are as defined in any one of tables 1 to 75.

Tables 301 to 375
Compounds of the formula I.e in which $R^1$ and $(R^{5a})_n$ are as defined in any one of tables 1 to 75.

Tables 376 to 450
Compounds of the formula I.f in which $R^1$ and $(R^{5a})_n$ are as defined in any one of tables 1 to 75.

Tables 451 to 525
Compounds of the formula I.g in which $R^1$ and $(R^{5a})_n$ are as defined in any one of tables 1 to 75.

Rings $R^a.1$ to $R^a.60$ are depicted beneath table B. In tables A and B, the indicator (2-, 3-, 4-, 5-, 6-, 2,3-, 2,4-, 2,5-, 2,6-, 3,4-, 3,5- etc.) relates to the position to which the radical $R^{5a}$ is bound on the phenyl ring (for the positions see phenyl ring in the above formulae I.a to I.i). If $(R^{5a})_n$ is defined with a dash (-), this means that n is 0 (no substituent $R^{5a}$).

TABLE A

| No. | $(R^{5a})n$ |
|---|---|
| A-1. | — |
| A-2. | 2-F |
| A-3. | 3-F |
| A-4. | 4-F |
| A-5. | 2,3-$F_2$ |
| A-6. | 2,4-$F_2$ |
| A-7. | 2,5-$F_2$ |
| A-8. | 2,6-$F_2$ |
| A-9. | 3,4-$F_2$ |
| A-10. | 3,5-$F_2$ |
| A-11. | 2-Cl |
| A-12. | 3-Cl |
| A-13. | 4-Cl |
| A-14. | 2,3-$Cl_2$ |
| A-15. | 2,4-$Cl_2$ |
| A-16. | 2,5-$Cl_2$ |
| A-17. | 2,6-$Cl_2$ |
| A-18. | 3,4-$Cl_2$ |
| A-19. | 3,5-$Cl_2$ |
| A-20. | 2-CN |
| A-21. | 3-CN |
| A-22. | 4-CN |
| A-23. | 2-$CH_3$ |
| A-24. | 3-$CH_3$ |
| A-25. | 4-$CH_3$ |
| A-26. | 2-$CHF_2$ |
| A-27. | 3-$CHF_2$ |
| A-28. | 4-$CHF_2$ |
| A-29. | 2-$CF_3$ |
| A-30. | 3-$CF_3$ |
| A-31. | 4-$CF_3$ |
| A-32. | 2-$OCH_3$ |
| A-33. | 3-$OCH_3$ |
| A-34. | 4-$OCH_3$ |
| A-35. | 2-$OCHF_2$ |
| A-36. | 3-$OCHF_2$ |
| A-37. | 4-$OCHF_2$ |
| A-38. | 2-$OCF_3$ |
| A-39. | 3-$OCF_3$ |
| A-40. | 4-$OCF_3$ |
| A-41. | 2-OH, 5-$CH_3$ |
| A-42. | 2-$OCH_3$, 5-$CH_3$ |
| A-43. | 2-COOH |
| A-44. | 3-COOH |
| A-45. | 4-COOH |
| A-46. | 2-$CONH_2$ |
| A-47. | 3-$CONH_2$ |
| A-48. | 4-$CONH_2$ |
| A-49. | 2-(azetidin-1-yl) |
| A-50. | 3-(azetidin-1-yl) |
| A-51. | 4-(azetidin-1-yl) |
| A-52. | 2-(3-hydroxyazetidin-1-yl) |
| A-53. | 3-(3-hydroxyazetidin-1-yl) |
| A-54. | 4-(3-hydroxyazetidin-1-yl) |
| A-55. | 2-(3-carboxyazetidin-1-yl) |
| A-56. | 3-(3-carboxyazetidin-1-yl) |
| A-57. | 4-(3-carboxyazetidin-1-yl) |
| A-58. | 2-(pyrrolidin-1-yl) |
| A-59. | 3-(pyrrolidin-1-yl) |
| A-60. | 4-(pyrrolidin-1-yl) |
| A-61. | 2-(3-hydroxypyrrolidin-1-yl) |
| A-62. | 3-(3-hydroxypyrrolidin-1-yl) |
| A-63. | 4-(3-hydroxypyrrolidin-1-yl) |
| A-64. | 2-(3-methoxypyrrolidin-1-yl) |
| A-65. | 3-(3-methoxypyrrolidin-1-yl) |
| A-66. | 4-(3-methoxypyrrolidin-1-yl) |
| A-67. | 2-(3-carboxypyrrolidin-1-yl) |
| A-68. | 3-(3-carboxypyrrolidin-1-yl) |
| A-69. | 4-(3-carboxypyrrolidin-1-yl) |
| A-70. | 2-(piperidin-1-yl) |
| A-71. | 3-(piperidin-1-yl) |
| A-72. | 4-(piperidin-1-yl) |
| A-73. | 2-(4-hydroxypiperidin-1-yl) |
| A-74. | 3-(4-hydroxypiperidin-1-yl) |
| A-75. | 4-(4-hydroxypiperidin-1-yl) |
| A-76. | 2-(4-carboxypiperidin-1-yl) |
| A-77. | 3-(4-carboxypiperidin-1-yl) |
| A-78. | 4-(4-carboxypiperidin-1-yl) |
| A-79. | 2-(piperazin-1-yl) |
| A-80. | 3-(piperazin-1-yl) |
| A-81. | 4-(piperazin-1-yl) |
| A-82. | 2-(1-methylpiperazin-4-yl) |
| A-83. | 3-(1-methylpiperazin-4-yl) |
| A-84. | 4-(1-methylpiperazin-4-yl) |

TABLE B

| No. | $(R^{5a})_n$ |
|---|---|
| B-1 | 2-$R^a.1$ |
| B-2 | 3-$R^a.1$ |
| B-3 | 4-$R^a.1$ |
| B-4 | 2-$R^a.2$ |
| B-5 | 3-$R^a.2$ |
| B-6 | 4-$R^a.2$ |
| B-7 | 2-$R^a.3$ |
| B-8 | 3-$R^a.3$ |
| B-9 | 4-$R^a.3$ |
| B-10 | 2-$R^a.4$ |
| B-11 | 3-$R^a.4$ |
| B-12 | 4-$R^a.4$ |
| B-13 | 2-$R^a.5$ |
| B-14 | 3-$R^a.5$ |
| B-15 | 4-$R^a.5$ |
| B-16 | 2-$R^a.6$ |
| B-17 | 3-$R^a.6$ |
| B-18 | 4-$R^a.6$ |

TABLE B-continued

| No. | $(R^{5a})_n$ |
|---|---|
| B-19 | 2-$R^a$.7 |
| B-20 | 3-$R^a$.7 |
| B-21 | 4-$R^a$.7 |
| B-22 | 2-$R^a$.8 |
| B-23 | 3-$R^a$.8 |
| B-24 | 4-$R^a$.8 |
| B-25 | 2-$R^a$.9 |
| B-26 | 3-$R^a$.9 |
| B-27 | 4-$R^a$.9 |
| B-28 | 2-$R^a$.10 |
| B-29 | 3-$R^a$.10 |
| B-30 | 4-$R^a$.10 |
| B-31 | 2-$R^a$.11 |
| B-32 | 3-$R^a$.11 |
| B-33 | 4-$R^a$.11 |
| B-34 | 2-$R^a$.12 |
| B-35 | 3-$R^a$.12 |
| B-36 | 4-$R^a$.12 |
| B-37 | 2-$R^a$.13 |
| B-38 | 3-$R^a$.13 |
| B-39 | 4-$R^a$.13 |
| B-40 | 2-$R^a$.14 |
| B-41 | 3-$R^a$.14 |
| B-42 | 4-$R^a$.14 |
| B-43 | 2-$R^a$.15 |
| B-44 | 3-$R^a$.15 |
| B-45 | 4-$R^a$.15 |
| B-46 | 2-$R^a$.16 |
| B-47 | 3-$R^a$.16 |
| B-48 | 4-$R^a$.16 |
| B-49 | 2-$R^a$.17 |
| B-50 | 3-$R^a$.17 |
| B-51 | 4-$R^a$.17 |
| B-52 | 2-$R^a$.18 |
| B-53 | 3-$R^a$.18 |
| B-54 | 4-$R^a$.18 |
| B-55 | 2-$R^a$.19 |
| B-56 | 3-$R^a$.19 |
| B-57 | 4-$R^a$.19 |
| B-58 | 2-$R^a$.20 |
| B-59 | 3-$R^a$.20 |
| B-60 | 4-$R^a$.20 |
| B-61 | 2-$R^a$.21 |
| B-62 | 3-$R^a$.21 |
| B-63 | 4-$R^a$.21 |
| B-64 | 2-$R^a$.22 |
| B-65 | 3-$R^a$.22 |
| B-66 | 4-$R^a$.22 |
| B-67 | 2-$R^a$.23 |
| B-68 | 3-$R^a$.23 |
| B-69 | 4-$R^a$.23 |
| B-70 | 2-$R^a$.24 |
| B-71 | 3-$R^a$.24 |
| B-72 | 4-$R^a$.24 |
| B-73 | 2-$R^a$.25 |
| B-74 | 3-$R^a$.25 |
| B-75 | 4-$R^a$.25 |
| B-76 | 2-$R^a$.26 |
| B-77 | 3-$R^a$.26 |
| B-78 | 4-$R^a$.26 |
| B-79 | 2-$R^a$.27 |
| B-80 | 3-$R^a$.27 |
| B-81 | 4-$R^a$.27 |
| B-82 | 2-$R^a$.28 |
| B-83 | 3-$R^a$.28 |
| B-84 | 4-$R^a$.28 |
| B-85 | 2-$R^a$.29 |
| B-86 | 3-$R^a$.29 |
| B-87 | 4-$R^a$.29 |
| B-88 | 2-$R^a$.30 |
| B-89 | 3-$R^a$.30 |
| B-90 | 4-$R^a$.30 |
| B-91 | 2-$R^a$.31 |
| B-92 | 3-$R^a$.31 |
| B-93 | 4-$R^a$.31 |
| B-94 | 2-$R^a$.32 |
| B-95 | 3-$R^a$.32 |
| B-96 | 4-$R^a$.32 |
| B-97 | 2-$R^a$.33 |
| B-98 | 3-$R^a$.33 |
| B-99 | 4-$R^a$.33 |
| B-100 | 2-$R^a$.34 |
| B-101 | 3-$R^a$.34 |
| B-102 | 4-$R^a$.34 |
| B-103 | 2-$R^a$.35 |
| B-104 | 3-$R^a$.35 |
| B-105 | 4-$R^a$.35 |
| B-106 | 2-$R^a$.36 |
| B-107 | 3-$R^a$.36 |
| B-108 | 4-$R^a$.36 |
| B-109 | 2-$R^a$.37 |
| B-110 | 3-$R^a$.37 |
| B-111 | 4-$R^a$.37 |
| B-112 | 2-$R^a$.38 |
| B-113 | 3-$R^a$.38 |
| B-114 | 4-$R^a$.38 |
| B-115 | 2-$R^a$.39 |
| B-116 | 3-$R^a$.39 |
| B-117 | 4-$R^a$.39 |
| B-118 | 2-$R^a$.40 |
| B-119 | 3-$R^a$.40 |
| B-120 | 4-$R^a$.40 |
| B-121 | 2-$R^a$.41 |
| B-122 | 3-$R^a$.41 |
| B-123 | 4-$R^a$.41 |
| B-124 | 2-$R^a$.42 |
| B-125 | 3-$R^a$.42 |
| B-126 | 4-$R^a$.42 |
| B-127 | 2-$R^a$.43 |
| B-128 | 3-$R^a$.43 |
| B-129 | 4-$R^a$.43 |
| B-130 | 2-$R^a$.44 |
| B-131 | 3-$R^a$.44 |
| B-132 | 4-$R^a$.44 |
| B-133 | 2-$R^a$.45 |
| B-134 | 3-$R^a$.45 |
| B-135 | 4-$R^a$.45 |
| B-136 | 2-$R^a$.46 |
| B-137 | 3-$R^a$.46 |
| B-138 | 4-$R^a$.46 |
| B-139 | 2-$R^a$.47 |
| B-140 | 3-$R^a$.47 |
| B-141 | 4-$R^a$.47 |
| B-142 | 2-$R^a$.48 |
| B-143 | 3-$R^a$.48 |
| B-144 | 4-$R^a$.48 |
| B-145 | 2-$R^a$.49 |
| B-146 | 3-$R^a$.49 |
| B-147 | 4-$R^a$.49 |
| B-148 | 2-$R^a$.50 |
| B-149 | 3-$R^a$.50 |
| B-150 | 4-$R^a$.50 |
| B-151 | 2-$R^a$.51 |
| B-152 | 3-$R^a$.51 |
| B-153 | 4-$R^a$.51 |
| B-154 | 2-$R^a$.52 |
| B-155 | 3-$R^a$.52 |
| B-156 | 4-$R^a$.52 |
| B-157 | 2-$R^a$.53 |
| B-158 | 3-$R^a$.53 |
| B-159 | 4-$R^a$.53 |
| B-160 | 2-$R^a$.54 |
| B-161 | 3-$R^a$.54 |
| B-162 | 4-$R^a$.54 |
| B-163 | 2-$R^a$.55 |
| B-164 | 3-$R^a$.55 |
| B-165 | 4-$R^a$.55 |
| B-166 | 2-$R^a$.56 |
| B-167 | 3-$R^a$.56 |
| B-168 | 4-$R^a$.56 |
| B-169 | 2-$R^a$.57 |
| B-170 | 3-$R^a$.57 |
| B-171 | 4-$R^a$.57 |
| B-172 | 2-$R^a$.58 |
| B-173 | 3-$R^a$.58 |
| B-174 | 4-$R^a$.58 |

TABLE B-continued

| No. | $(R^{5a})_n$ |
|---|---|
| B-175 | 2-$R^a$.59 |
| B-176 | 3-$R^a$.59 |
| B-177 | 4-$R^a$.59 |
| B-178 | 2-$R^a$.60 |
| B-179 | 3-$R^a$.60 |
| B-180 | 4-$R^a$.60 |

Rings $R^a$.1 to $R^a$.60:

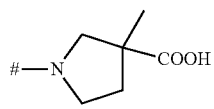  R<sup>a</sup>.15
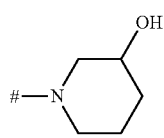  R<sup>a</sup>.16
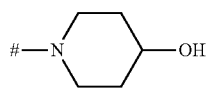  R<sup>a</sup>.17
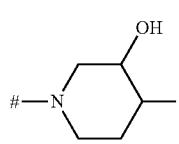  R<sup>a</sup>.18
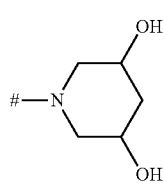  R<sup>a</sup>.19
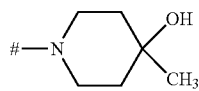  R<sup>a</sup>.20
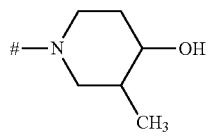  R<sup>a</sup>.21
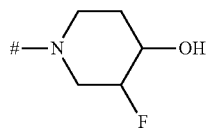  R<sup>a</sup>.22
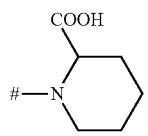  R<sup>a</sup>.23
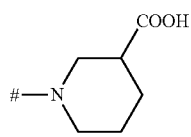  R<sup>a</sup>.24
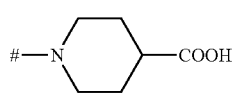  R<sup>a</sup>.25
R<sup>a</sup>.35
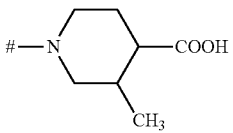
R<sup>a</sup>.36
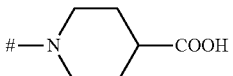
R<sup>a</sup>.37
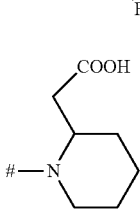
R<sup>a</sup>.38
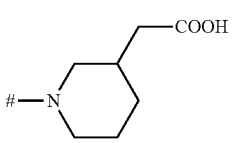
R<sup>a</sup>.39
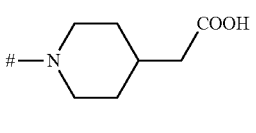
R<sup>a</sup>.40
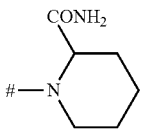
R<sup>a</sup>.41
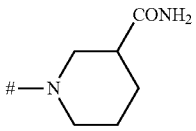
R<sup>a</sup>.42
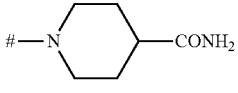
R<sup>a</sup>.43
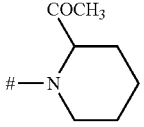
R<sup>a</sup>.44
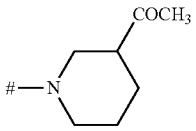
R<sup>a</sup>.45
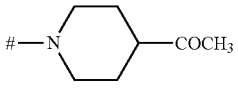

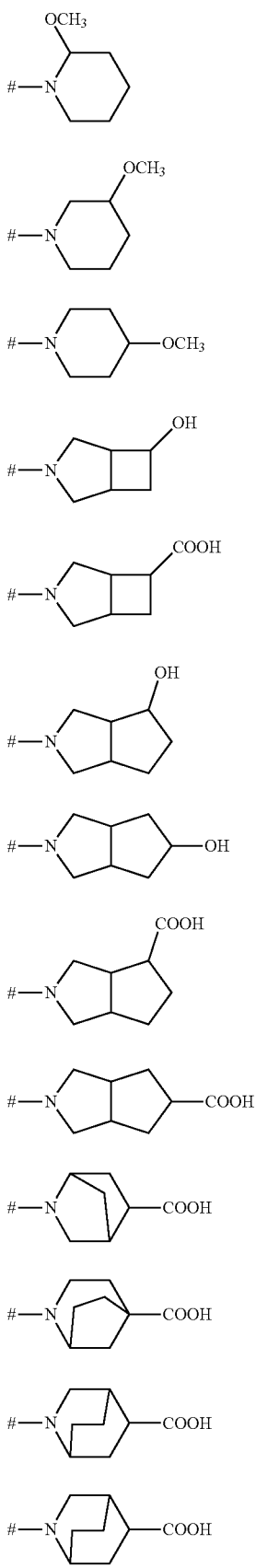

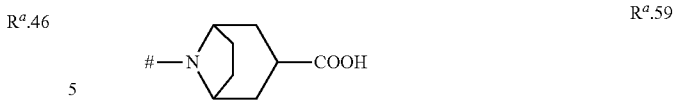

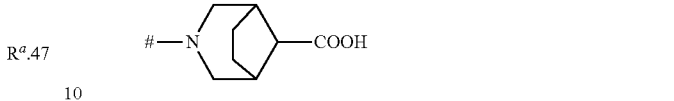

Among the above compounds, preference is given to compounds I.a.

In a specific embodiment, the invention relates to compounds I selected from the compounds of the examples, either in form of free bases or of any pharmaceutically acceptable salt thereof or a stereoisomer, the racemate or any mixture of stereoisomers thereof or a tautomer or a tautomeric mixture or an N-oxide thereof.

The compounds of the present invention can be prepared by using routine techniques familiar to a skilled person. In particular, the compounds of the formula I can be prepared according to the following schemes, wherein the variables, if not stated otherwise, are as defined above.

Compounds of the formula I wherein $R^1$ is $R^a$ (termed in the following compounds I') can be prepared, for example, starting from quinoline compounds 1 which are substituted in 8-position by a leaving group X, such as a halogen atom, e.g. F, Cl, Br or I, in particular F, or a sulfonate, such as triflate, nonaflate or tosylate, and heterocyclic compound $R^a$—H in a coupling reaction in the presence of a base according to standard processes, e.g. according to the processes described in WO 2005/113539 or US 2007/0027161, or without a base in a polar aprotic solvent such as dimethyl sulfoxide (DMSO) as described in Bioorg. Med. Chem. Lett., 2003, 13, 1329. The coupling reaction is depicted in scheme 1.

Suitable bases include alkali metal carbonates, such as lithium carbonate, sodium carbonate, potassium carbonate, alkalimetal hydroxides such as lithium hydroxide, sodium hydroxide and potassium hydroxide, alkalimetal alkoxides such as, sodium methoxide, sodium ethoxide, sodium propoxide, sodium n-butoxide, sodium tert.-butoxide, lithium methoxide, lithium ethoxide, lithium propoxide, lithium n-butoxide, lithium tert.-butoxide, potassium methoxide, potassium ethoxide, potassium propoxide, potassium n-butoxide, potassium tert.-butoxide, alkalimetal hydrides such as lithium hydride, sodium hydride or potassium hydride. The amount of base is preferably at least 0.9 mol per mol of amine III, in particular at least 1.0 mol per mol of amine III, e.g. from 1.1 to 10 mol per mol of amine III.

Suitable bases can be inorganic or organic. Examples for suitable inorganic bases are alkali metal carbonates, e.g. $Li_2CO_3$, $Na_2CO_3$, $K_2CO_3$ or $Cs_2CO_3$, alkali metal hydroxides, e.g. LiOH, NaOH or KOH, or phosphates, e.g. $Li_3PO_4$, $Na_3PO_4$, $K_3PO_4$ or $Cs_3PO_4$. Examples for suitable organic bases are open-chained amines, e.g. trimethylamine, triethylamine, tripropylamine, ethyldiisopropylamine and the like, basic N-heterocycles, such as morpholine, pyridine, lutidine, DABCO, DBU or DBN, alkoxylates, e.g. sodium or potassium methanolate, ethanolate, propanolate, isopropanolate, butanolate or tert-butanolate, especially sterically hindered alkoxylates, such as sodium or potassium tert-butanolate, silanolates, like sodium or potassium trimethylsilanolate ($(CH_3)_3SiO^-$) or triisopropylsilanolate ($(CH(CH_3)_2)_3SiO^-$), phosphazene bases (superbases), such as BEMP and t-Bu-P4

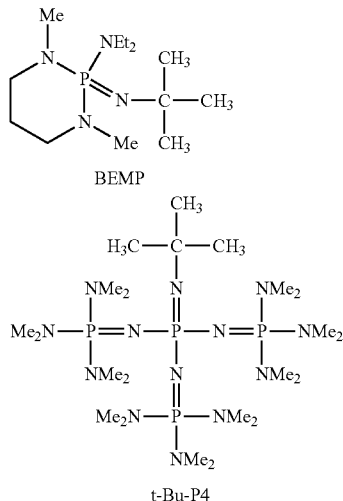

BEMP t-Bu-P4

(Me = methyl; Et = ethyl)

or phenolates, especially sterically hindered phenolates, like the sodium or potassium salts of the following hydroxyaromatic compounds:

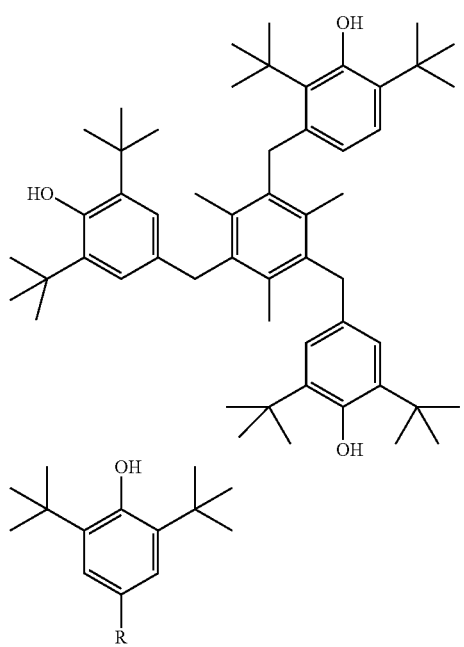

wherein R is H or optionally substituted $C_1$-$C_2$-alkyl, e.g. methyl, $CH_2$—$N(CH_3)_2$ or $CH_2CH_2$—$C(O)$—$O$—$C_{18}H_{21}$. Specifically, inorganic bases, such as the alkali metal carbonates, e.g. $Li_2CO_3$, $Na_2CO_3$, $K_2CO_3$ or $Cs_2CO_3$, are used.

Generally, the coupling reaction is performed in an inert solvent. Suitable inert solvents include aromatic hydrocarbons, such as benzene, toluene, the xylenes, ethylbenzene, isopropylbenzene, butylbenzene, tert.-butylbenzene, chlorobenzene, the dichlorobenzenes or anisol, aliphatic or alicyclic ethers, such as tetrahydrofuran, methyltetrahydrofuran or dioxane, aliphatic or alicyclic sulfones and sulfoxides, such as dimethyl sulfoxide, sulfolane and the like, and N,N-dialkylamides of aliphatic $C_1$-$C_3$-carboxylic acids and N-alkyllactames, such as dimethyl formamide, dimethyl acetamide, N-methylpyrrolidon, N-methylpiperidone, or N-ethylpyrrolidone.

Scheme 1

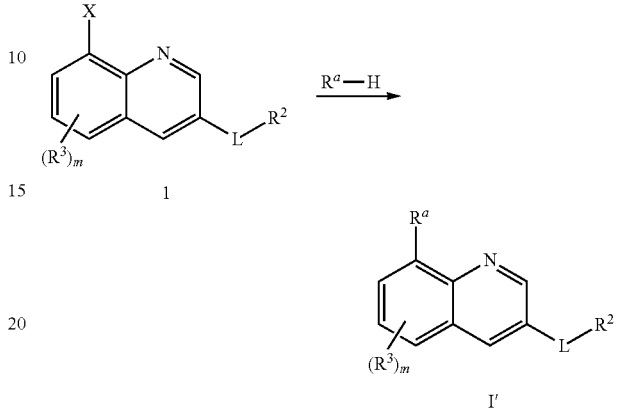

If the (hetero)aromatic ring $R^2$ carries a substituent $R^5$ which can compete in this reaction (e.g. if $R^5$ is a halogen atom which is as reactive as X or even more reactive), compounds I can form in which $R^a$ is bound to the (hetero) aromatic ring $R^2$ instead of the 8-position of the quinoline scaffold (termed in the following compounds I"). Moreover, compounds I can form in which $R^a$ is bound both to the 8-position of the quinoline ring and to the (hetero)aromatic ring $R^2$ (termed in the following compounds I'"). Compounds I', I" and I'" can be separated from each other by standard procedures, e.g. by chromatographic methods. If the formation of compounds I" and I'" is to be prevented, $R^5$, if present, has to be unreactive towards $R^a$—H under the given conditions or at least significantly less reactive than X.

If inversely compounds I" are to be obtained, in which $R^a$ is bound to the (hetero)aromatic ring $R^2$ instead of the 8-position of the quinoline scaffold, the starting compound 2 expediently carries as radical $R^1$ a substituent which is unreactive towards $R^a$—H under the given conditions or at least significantly less reactive than X. X in scheme 2 is, like in scheme 1, a leaving group, such as a halogen atom, e.g. F, Cl, Br or I, or a sulfonate, such as triflate, nonaflate or tosylate. $R^{2'}$ is $R^2$ without the desired $R^a$ substituent.

Scheme 2

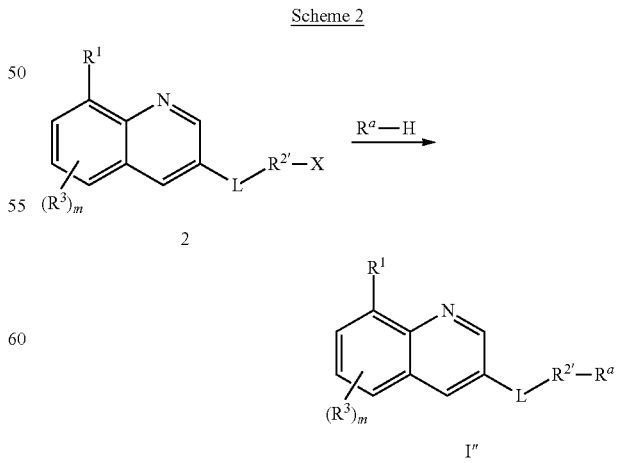

In the above reactions, $R^3$, if present, is expediently unreactive towards $R^a$—H under the given conditions or at least significantly less reactive than X. Otherwise $R^a$ may be bound in the position of $R^3$ instead of that of X.

The ring $R^a$ may also be introduced in a Buchwald-Hartwig reaction. In this context, the starting compounds 1 or 2 are reacted with $R^a$—H in the presence of a transition metal-catalyst, mostly a Pd catalyst, and generally also in the presence of a base. In compounds 1 or 2 X is in particular Cl, Br or I.

The Pd catalyst can generally either be used as a salt (e.g. Pd(II) acetate or $Na_2PdCl_4$) or, more often, as a Pd(II) complex which is either preformed or prepared in situ from a Pd(II) salt (e.g. Pd(II)acetate or PdCl2) and the respective ligand. The same applies to Ni catalysts. Suitable ligands for the complex often contain phosphorus. Examples for phosphorus ligands are di-tert-butyl(1-methyl-2,2-diphenylcyclopropyl)-phosphine (cBRIDP; Mo-Phos), 2-di-tert-butylphosphino-2',4',6'-triisopropylbiphenyl (t-Bu XPhos, tBuXPhos, tert-Butyl XPhos), 1,1'-bis(diphenylphosphino)ferrocene (dppf), 1,1'-bis(di-tert-butylphosphino)ferrocene (dtbpf), 1,2-bis(diphenylphosphino)-ethane (dppe), 1,3-bis(diphenylphosphino)₋propane (dppp), 1,4-bis(diphenylphosphino)butane (dppb), (2,3-O-isopropylidene-2,3-dihydroxy-1,4-bis(diphenyl-phosphino)butane (diop), bis(di-tert-butyl(4-dimethylaminophenyl)₋phosphine) (Amphos), (2S,3S)-(−)-bis(diphenylphosphino)butane (Chiraphos), di-(tert-butyl)phenylphosphine, 2,2'-bis(diphenylphosphino)-1,1'-binaphthyl (BINAP), [1,1'-biphenyl]-2-diisopropyl phosphine, 2-dicyclohexylphosphino-2',4',6'-triisopropylbiphenyl (X-phos), 9,9-dimethyl-4,5-bis(diphenyl₋phosphino)xanthene (Xantphos), 4,5-bis-(di-1-(3-methylindolyl)-phosphoramidit)-2,7,9,9-tetramethyl₋xanthene (MeSkatOX), 2-dicyclohexylphosphino-2',6'-dimethoxybiphenyl (S-phos), 2-(2-dicyclohexyl-phosphanylphenyl)-N1,N1,N3,N3-tetramethyl-benzene-1,3-diamine (C-phos), 6,6'-dimethoxy-[1,1'-biphenyl]-2,2'-diyl)bis(bis(3,5-dimethylphenyl)phosphine, [(4R)-(4,4'-bis-1,3-benzodioxole)-5,5'-diyl]bis[bis(3,5-di-tert-butyl-4-methoxyphenyl)phosphine] ((R)-DTBM-SEGPHOS®), (R)- or (S)-3,5-Xy1-MeO-BIPHEP, (R,S)- or (S,R)-PPF-P (t-Bu)2, the Josiphos ligands, triphenylphosphine, triphenylphosphite, tri-(2-(1,1-dimethylethyl)-4-methoxy-phenyl)-phosphite, tricyclohexylphosphine, tri(tert-butyl)phosphine, butyldi-1-adamantylphosphine (cataCXium), 1,6-bis(diphenylphosphino)hexane (DPPH), 2,6-bis(2,5-dimethylphenyl)-1-octyl-4-phenylphosphacyclohexan (PCH), tris(3-sulfophenyl)phosphine trisodium salt (TPPTS) and the like.

Non-phosphorus ligands are for example bis(dibenzylideneacetone) (dba), acetonitrile, bisoxazoline and the like. Further, examples for Pd catalysts with ligands without phosphorus are the PEPPSI catalysts (PEPPSI=Pyridine-Enhanced Precatalyst Preparation Stabilization and Initiation)

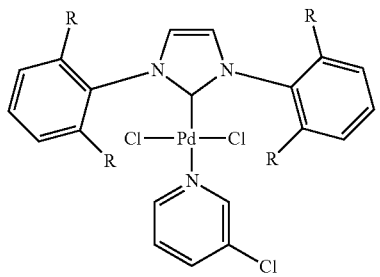

in which R is a small organic fragment, e.g. methyl, ethyl, isopropyl, isopentyl, or isoheptyl. The corresponding catalysts are labeled as PEPPSI-IMes, PEPPSI-IEt, PEPPSI-IPr, PEPPSI-IPent, and PEPPSI-IHept respectively, with or without "Pd—" added in front.

Also new generation PEPPSI catalysts are suitable:

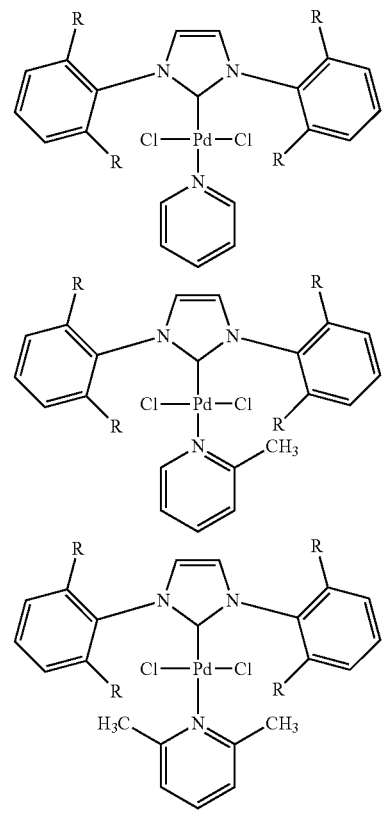

Here, too, R is a small organic fragment, e.g. methyl, ethyl, isopropyl, isopentyl, or isoheptyl.

The catalyst is generally used in catalytic, i.e. substoichiometric amounts, e.g. in an amount of from 0.001 to 0.5 mol per mol of that reactant which is not used in excess.

Suitable bases are those mentioned above.

Compounds 1 and 2 are either commercially available or can be prepared by standard reactions, such as described, for example, in WO 2003/080580 or WO 2009/019286.

For instance, compounds 1 and 2 wherein L is $S(O)_2$ (termed hereinafter compounds 1' and 2') can be prepared as outlined in schemes 3 and 4 by reacting the iodide 3 or 5 with the sulfinate 4 or 6. $M^+$ is a metal cation equivalent, such as $Li^+$, $Na^+$ or $K^+$, or is an ammonium cation ($NH_4^+$) or a substituted ammonium cation. The reaction is generally carried out in the presence of a transition metal catalyst, especially a Cu(I) catalyst, such as Cu (I) triflate, generally in a polar solvent, such as N,N-dimethyl acetamide (DMA) or DMF. In 3 X has to less reactive than I towards the sulfinate 4, and is for example F, Cl or Br.

Scheme 3

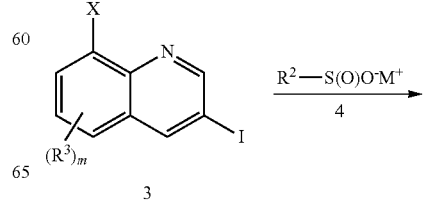

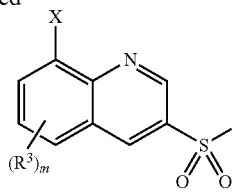

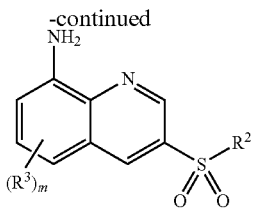

Scheme 4

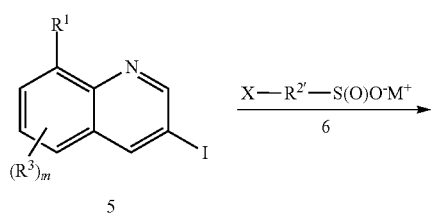

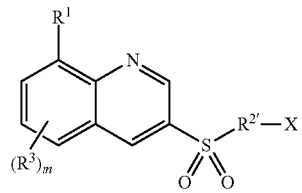

For preparing compounds 1' wherein X is I, the nitro compound 7 can be used as starting material, as shown in scheme 5 below. After conversion to 8 in analogy to the reaction in scheme 3 or 4 the nitro group is reduced and the amino group is then submitted to a substitution reaction to yield 1' with X=I. Reduction can be achieved by a variety of methods, including reduction with "non-hydrogen" reducing agents such as $SnCl_2$, or by catalytic hydrogenation techniques familiar to those skilled in the art. For substituting the amino group by I, a Sandmeyer reaction can be carried out, using a nitrosonium source (e.g. $NaNO_2$, $nBuNO_2$) and a iodide (e.g. CuI or $n-Bu_4NI$) in a suitable solvent, such water or $CH_3CN$.

Scheme 5

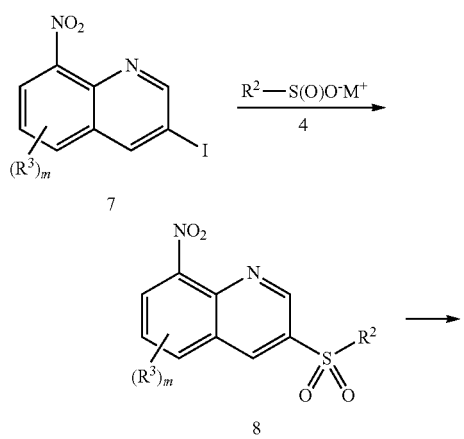

The sulfonates 4 and 6 can be obtained, for example, by reacting the corresponding sulfonyl chlorides ($R^2$—$S(O)_2$—Cl or X—$R^{2'}$—$S(O)_2$—Cl) with a reducing agent and neutralizing the sulfinic acid formed. For instance, the sulfite of $M^+$, e.g. sodium sulfite, can be used, if desired in the presence of a base.

Compounds 1 and 2 wherein L is NH—$S(O)_2$ (termed hereinafter compounds 1" and 2") can be prepared as outlined in schemes 6 and 7 by reacting the amine 10 or 12 with the sulfonyl chloride 11 or 13.

Scheme 6

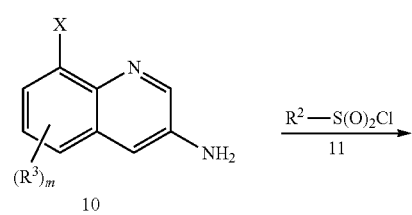

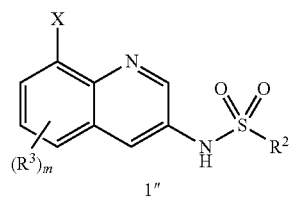

Scheme 7

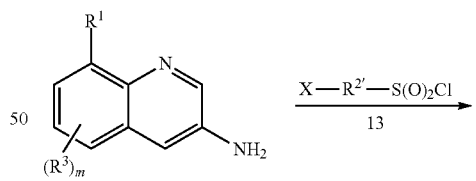

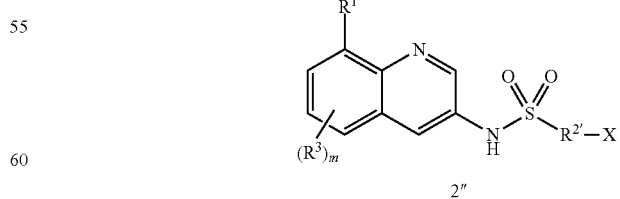

Compounds 1 and 2 wherein L is $S(O)_2$—NH (termed hereinafter compounds 1''' and 2''') can be prepared as outlined in schemes 8 and 9 by reacting the sulfonyl chloride 10 or 16 with the amine 15 or 17.

Scheme 8

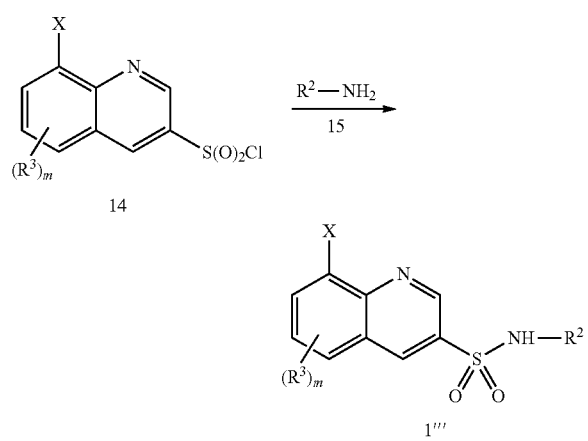

Scheme 9

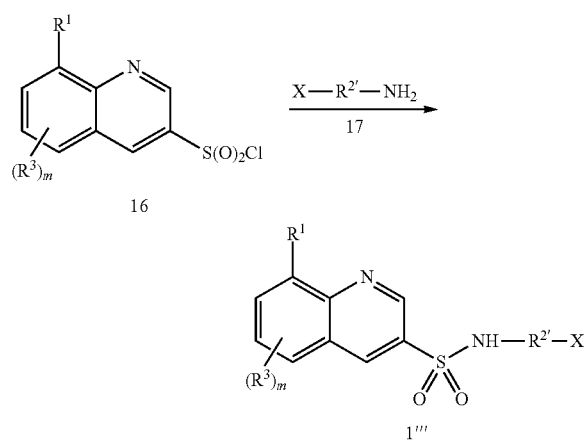

The reactions in schemes 6 to 9 are generally carried out in the presence of a base. Suitable bases are those listed above.

Compounds 1 and 2 wherein L is C(O)—NH can be prepared in analogy to schemes 6 and 7, where however instead of the sulfonyl chloride 11 and 13 a suitable carbonyl compound is used. Suitable carbonyl compounds are e.g. the respective carboxylic acids ($R^2$—C(O)OH or X—$R^{2'}$—C(O)OH), carbonyl chlorides ($R^2$—C(O)Cl or X—$R^{2'}$—C(O)Cl), esters ($R^2$—C(O)OR or X—$R^{2'}$—C(O)OR), or anhydrides ($R^2$—C(O)OC(O)—$R^1$ or X—$R^{2'}$—C(O)OC(O)R').

If a carboxylic acid is used, the reaction is generally carried out in the presence of a coupling reagent. Suitable coupling reagent (activators) are well known and are for instance selected from the group consisting of carbodiimides, such as EDCI (1-ethyl-3-(3-dimethylaminopropyl)carbodiimide; also abbreviated as EDC), DCC (dicyclohexylcarbodiimide) and DIC (diisopropylcarbodiimide), benzotriazole derivatives, such as HOBt (1-hydroxybenzotriazole), HATU (O-(7-azabenzotriazol-1-yl)-N,N,N',N'-tetramethyluronium hexafluorophosphate), HBTU ((O-benzotriazol-1-yl)-N,N,N',N'-tetramethyluronium hexafluorophosphate) and HCTU (1H-benzotriazolium-1-[bis(dimethylamino)methylene]-5-chloro tetrafluoroborate), phosphonium-derived activators, such as BOP ((benzotriazol-1-yloxy)-tris(dimethylamino)phosphonium hexafluorophosphate), Py-BOP ((benzotriazol-1-yloxy)-tripyrrolidinphosphonium hexafluorophosphate) and Py-BrOP (bromotripyrrolidinphosphonium hexafluorophosphate), and others, such as COMU ((1-cyano-2-ethoxy-2-oxoethylidenaminooxy)dimethylamino-morpholino-carbenium-hexafluorophosphat). The above activators can also be used in combination with each other. Generally, the activator is used in at least equimolar amounts, with respect to that reactant not used in excess. The benzotriazole and phosphonium coupling reagents are generally used in a basic medium.

Suitable esters derive expediently from $C_1$-$C_4$-alkanols ROH in which R is $C_1$-$C_4$-alkyl, such as methanol, ethanol, propanol, isopropanol, n-butanol, butan-2-ol, isobutanol and tert-butanol, preference being given to the methyl and ethyl esters (R=methyl or ethyl). Suitable esters may also derive from $C_2$-$C_6$-polyols such as glycol, glycerol, trimethylolpropane, erythritol, pentaerythritol and sorbitol, preference being given to the glyceryl ester. When polyol esters are used, it is possible to use mixed esters, i.e. esters with different R radicals.

Alternatively, the ester is a so-called active ester, which is obtained in a formal sense by the reaction of the carboxylic acid with an active ester-forming alcohol, such as p-nitrophenol, N-hydroxybenzotriazole (HOBt), N-hydroxysuccinimide or OPfp (pentafluorophenol).

The acid anhydride is either a symmetric anhydride $R^2$—C(O)OC(O)—$R^2$ or X—$R^{2'}$—C(O)OC(O)$R^{2'}$—X or an asymmetric anhydride in which —O—OC— R' is a group which can be displaced easily by the amino group. Suitable acid derivatives with which the carboxylic acid can form suitable mixed anhydrides are, for example, the esters of chloroformic acid, for example isopropyl chloroformate and isobutyl chloroformate, or of chloroacetic acid.

If a carbonyl chloride is used, the reaction is generally carried out in the presence of a base. Suitable bases are those listed above.

Compounds 1 and 2 wherein L is a chemical bond can for example be prepared by various C—C coupling reactions of the suitable $R^2$ or X—$R^{2'}$ derivative and the quinoline derivative. A suitable coupling reaction is for example the Suzuki reaction. For example, compound 3, 5 or 7 can be reacted with the suitable boronic ester of $R^2$ or X—$R^{2'}$.

Compounds 1 and 2 wherein L is an ethynyl bridge can be prepared, for example, via a Sonogashira reaction, e.g. by reacting a compound 3, 5 or 7 with HC≡C—$R^2$ or HC≡C—$R^{2'}$—X in the presence of a suitable catalyst.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The present invention moreover relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, the unlabelled compounds according to the invention might naturally include certain amounts of these respective isotopes. Therefore, when referring to compounds I, wherein at least one of the atoms has been replaced by its stable, non-radioactive isotope, it will be understood that the isotope is present in a higher amount than would naturally occur.

Stable isotopes (e.g., deuterium, $^{13}C$, $^{15}N$, $^{18}O$) are non-radioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10): 927-932 (1995); Kushner et al., Can. J. Physiol. Pharmacol., 77, 79-88 (1999).

Incorporation of a heavy atom, particularly substitution of deuterium for hydrogen, can give rise to an isotope effect that could alter the pharmacokinetics of the drug.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The present invention further relates to a pharmaceutical composition comprising at least one compound of formula I, a stereoisomer, prodrug, tautomer and/or physiologically tolerated acid addition salt thereof and optionally at least one physiologically acceptable carrier and/or auxiliary substance.

The invention relates moreover to the use of compounds of formula I or of a stereoisomer, N-oxide, prodrug, tautomer or physiologically tolerated acid addition salt thereof or of a compound of formula I, wherein at least one of the atoms has been replaced by its stable, non-radioactive isotope, for the preparation of a medicament for the treatment of a medical disorder susceptible to the treatment with a 5-HT$_6$ receptor ligand, and to a method for treating a medical disorder susceptible to the treatment with a 5-HT$_6$ receptor ligand, said method comprising administering an effective amount of at least one compound of formula I or of a stereoisomer, N-oxide, prodrug, tautomer or physiologically tolerated acid addition salt thereof or of a compound of formula I, wherein at least one of the atoms has been replaced by its stable, non-radioactive isotope, or of a pharmaceutical composition as defined above to a subject in need thereof.

The present invention also relates to the compounds of formula I or a stereoisomer, N-oxide, prodrug, tautomer or physiologically tolerated acid addition salt thereof or a compound of formula I, wherein at least one of the atoms has been replaced by its stable, non-radioactive isotope, for use in modulating the 5-HT$_6$ receptor.

The compounds of the present invention can be a 5-HT$_6$ receptor agonist, including partial agonistic activity, or a 5-HT$_6$ receptor antagonist, including inverse agonist activity.

The compounds according to the present invention, as well as their salts and their N-oxides, have a surprisingly high affinity for 5-HT$_6$ receptors. The high affinity of the compounds according to the invention for 5-HT$_6$ receptors is reflected in very low in-vitro receptor binding constants ($K_i$(5-HT$_6$) values) of as a rule less than 500, 100 or 50 nM (nmol/l), preferably of less than 10 nM and, in particular of less than 5 nM. The displacement of $^3$H-LSD can, for example, be used in receptor binding studies for determining binding affinities to 5-HT$_6$ receptors.

Furthermore the compounds of the invention, as well as their salts and their N-oxides, are highly selective 5-HT$_6$ receptor ligands which, because of their low affinity for other receptors such as dopamine receptors, adrenergic receptors, muscarinic receptors, histamine receptors, opiate receptors, in particular dopamine D$_2$, $\alpha_1$-adrenergic and histamine H$_1$ receptors, give rise to fewer side-effects than other, less selective 5-HT$_6$ ligands.

For instance the 5-HT$_6$/D$_2$, 5-HT$_6$/$\alpha_1$-adrenergic or 5-HT$_6$/H$_1$ selectivities of the compounds according to the present invention, i.e. the ratios $K_i$(D$_2$)/$K_i$(5-HT$_6$), $K_i$($\alpha_1$-adrenergic)/$K_i$(5-HT$_6$) or $K_i$(H$_1$)/$K_i$(5-HT$_6$) of the receptor binding constants, is as a rule at least 25, preferably at least 50, even better at least 100.

The displacement of [$^3$H]SCH23390 or [$^{125}$I]spiperone can be used, for example, for carrying out receptor binding studies on D$_1$, D$_2$ and D$_4$ receptors.

Furthermore the compounds of the present invention because of their structural features are susceptible to display an enhanced brain penetration than other known 5-HT$_6$ receptor ligands.

Moreover, the compounds of the present invention because of their structural features show no or only low blockade of the hERG channel.

Because of their binding profile, the compounds of the present invention can be used for treating diseases which respond to 5-HT$_6$ receptor ligands (or which are susceptible to treatment with a 5-HT$_6$ receptor ligand), i.e. they are effective for treating those medical disorders or diseases in which exerting an influence on (modulating) the 5-HT$_6$ receptor leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-HT$_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases including e.g. drug addiction and obesity.

The addiction diseases include psychic disorders and behavioral disturbances which are caused by the abuse of psychotropic substances, including certain pharmaceuticals, such as sedative, anxiolytica, hypnotics or narcotics (hereinafter also referred to as drug addiction), and also other addiction diseases, such as addiction to gaming (gambling; impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, hallucinogens, NMDA-receptor antagonists such phencyclidine and related cyclidines, dextrometorphan, dextrorphan, ibogaine, ketimine and tiletamine, *cannabis*, nicotine and alcohol. Other addiction diseases include gaming (gambling), including problem gambling (compulsive gambling, ludomania), computer or video game addiction and internet addiction.

With regard to the treatment of addiction diseases, particular preference is given to those compounds according to the present invention which themselves do not possess any psychotropic effect. This can also be observed in a test using rats, which, after having been administered compounds which can be used in accordance with the invention, reduce their self administration of psychotropic substances, for example cocaine or alcohol.

According to another aspect of the present invention, the compounds according to the invention are suitable for treating disorders whose causes can at least partially be attributed to an anomalous activity of $5-HT_6$ receptors.

According to another aspect of the present invention, the treatment is directed, in particular, toward those disorders which can be influenced, within the sense of an expedient medicinal treatment, by the binding of preferably exogeneously administered binding partners (ligands) to $5-HT_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of the present invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of the present invention are particularly suitable for treating addiction diseases caused for instance by the abuse of psychotropic substances, such as pharmaceuticals, narcotics, nicotine or alcohol, including psychic disorders and behavioral disturbances related thereto. The compounds of the present invention are likewise particularly suitable for treating addiction diseases which are not caused by the abuse of psychotropic substances, such as gaming (gambling), including problem gambling (compulsive gambling, ludomania), computer or video game addiction and internet addiction. With regard to addiction diseases, the compound of the present invention can be used for the therapy during addiction and also for preventing relapse into addiction.

According to another aspect of the invention the compounds of the invention, their salts and their N-oxides are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of the invention, their salts and/or their N-oxides are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semi-solid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], 4th edition, Aulendorf: ECV-Editio-Kantor-Verlag, 1996.

The following examples serve to explain the present invention without limiting its scope.

EXAMPLES

Abbreviations

DMF N,N-dimethylformamide
NMP N-methylpyrrolidone
MeOH methanol
DCM dichloromethane
TFA trifluoroacetic acid
dppf 1,1'-bis(diphenylphosphino)ferrocen
BINAP 2,2'-bis(diphenylphosphino)-1,1'-binaphthyl
TLC thin liquid chromatography
Prep-TLC preparative TLC
Rf retention factor
Xphos Pd G2 catalyst (synonym: 2nd Generation XPhos Precatalyst, chloro(2-dicyclohexylphosphino-2',4',6'-triisopropyl-1,1'-biphenyl)[2-(2'-amino-1,1'-biphenyl)]-palladium(II), X-Phos aminobiphenyl palladium chloride precatalyst, XPhos-Pd-G2): catalyst of following formula:

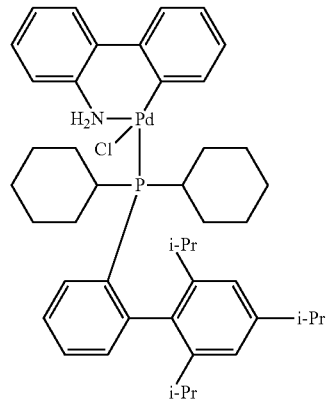

i-Pr = isopropyl

The compounds were either characterized via proton-NMR in deuterium oxide, $d_6$-dimethylsulfoxide, d-chloroform or $d_4$-methanol on a 400 MHz, 500 MHz or 600 MHz NMR instrument (Bruker AVANCE), or by mass spectrometry, generally recorded via HPLC-MS in a fast gradient on C18-material (electrospray-ionisation (ESI) mode).

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (br s), doublet (d), broad doublet (br d), triplet (t), broad triplet (br t), quartet (q), quintet (quint.), multiplet (m), broad multiplet (br m), doublet of doublets (dd), doublet of doublets of doublets (ddd), triplet of doublets (td), doublet of triplets of doublets (dtd), doublet of triplets of triplets (dtt), quartet of doublets of doublets (qdd) etc.

I. Preparation of the Compounds I

Example 1

1-[3-(3-Trifluoromethyl-benzenesulfonyl)-quinolin-8-yl]-piperidin-4-ol

8-Fluoro-3-iodoquinoline (5.29 g, 19.38 mmol), sodium 3-(trifluoromethyl)-benzenesulfinate (5.0 g, 19.38 mmol) and copper(I)trifluoromethanesulfonate benzene complex (10.84 g, 19.38 mmol) were dissolved in DMF (80 ml) and warmed up to 65° C. for 14 h and stirred at room temperature overnight. The reaction mixture was filtered through a fritted funnel and concentrated under high vacuo. The residue was dissolved in DCM and washed 5× with aqueous $NH_4OH$ solution. The organic layer was dried and concentrated. The residue was purified using flash chromatography (120 g column; cyclohexane 100%→cyclohexane:ethyl acetate 20:80, 85 ml/min) to give 8-fluoro-3-(3trifluoromethyl)phenylsulfonyl) quinolone (2.1 g, yield 30.5%). 8-Fluoro-3-(3-(trifluoromethyl)phenylsulfonyl)quinoline (600 mg, 1.689 mmol) and piperidin-4-ol (769 mg, 7.60 mmol) were suspended in NMP (18 ml) and $K_2CO_3$ (934 mg, 6.75 mmol) was added and stirred at 225° C. in Microwave for 40 min. The reaction mixture was diluted with ethyl acetate and washed 4× with water, dried and concentrated. The residue was purified using flash chromatography (DCM 100%→DCM:MeOH 98:2) to give 1-(3-(3-(trifluoromethyl)phenylsulfonyl)quinolin-8-yl)piperidin-4-ol (290 mg, yield 39.3%).

LCMS (ESI$^+$) m/z [M+H]$^+$: 437.10

$^1$H NMR (DMSO-$d_6$, 500 MHz): δ=9.34 (d, J=2.1 Hz, 1H), 9.14 (d, J=2.1 Hz, 1H), 8.44 (d, J=8.2 Hz, 1H), 8.41 (s, 1H), 8.13 (d, J=7.9 Hz, 1H), 7.91 (t, J=7.9 Hz, 1H), 7.73-7.76 (m, J=8.2 Hz, 1H), 7.63 (t, J=7.9 Hz, 1H), 7.33-7.36 (m, J=7.6 Hz, 1H), 4.70 (d, J=4.0 Hz, 1H), 3.63-3.70 (m, 3H), 2.95 (t, J=9.9 Hz, 2H), 1.90 (d, J=10.1 Hz, 2H), 1.60-1.68 (m, 2H)

Example 2

1-[3-(3-Trifluoromethyl-benzenesulfonyl)-quinolin-8-yl]-pyrrolidin-3-ol

The compound was prepared in analogy to example 19 starting from 8-fluoro-3-(3-(trifluoromethyl)phenylsulfonyl)quinoline and pyrrolidin-3-ol.

LCMS (ESI$^+$) m/z [M+H]$^+$: 423.10

Example 3

1-[3-(3-Trifluoromethyl-benzenesulfonyl)-quinolin-8-yl]-piperidine-4-carboxylic Acid 8-Fluoro-3-(3-(trifluoromethyl)phenylsulfonyl)quinoline (200 mg, 0.563 mmol) and piperidine-4-carboxylic acid (72.7 mg, 0.563 mmol) were suspended in NMP (2 ml) and $K_2CO_3$ (233 mg, 1.689 mmol) was added and stirred at 130° C. in Microwave for 11 h. The reaction mixture was diluted with ethyl acetate and washed 4× with water, dried and concentrated. The residue was purified using flash chromatography (4 g column; DCM 100%→DCM:MeOH 80:20; 18 ml/min) to give 1-(3-(3-(trifluoromethyl)phenylsulfonyl)quinolin-8-yl)piperidine-4-carboxylic acid (35 mg, yield 13.4%).

LCMS (ESI$^+$) m/z [M+H]$^+$: 465.10

$^1$H NMR (DMSO-d$_6$, 400 MHz): δ=12.18 (s, broad), 9.33 (d, J=2.4 Hz, 1H), 9.14 (d, J=2.4 Hz, 1H), 8.43 (d, J=8.3 Hz, 1H), 8.40 (s, 1H), 8.12 (d, J=7.8 Hz, 1H), 7.90 (m, 1H), 7.75 (d, J=1.0 Hz, 1H), 7.64 (t, 1H), 7.36 (d, J=1.2 Hz, 1H), 3.77 (d, J=12.0 Hz, 2H), 2.87 (m, J=2.2 Hz, 2H), 2.45-2.46 (m, 1H), 1.96-1.99 (m, 1H), 1.95 (br s, 1H), 1.84-1.85 (m, 1H), 1.82 (br. s., 1H).

Example 4

(S)-1-[3-(3-Trifluoromethyl-benzenesulfonyl)-quinolin-8-yl]-piperidin-3-ol Hydrochloride 8-Fluoro-3-(3-(trifluoromethyl)phenylsulfonyl)quinoline (200 mg, 0.563 mmol) and (S)-piperidin-3-ol hydrochloride (77 mg, 0.563 mmol) were suspended in NMP (2 ml) and tripotassium phosphate (597 mg, 2.81 mmol) was added and stirred in the Microwave at 140° C. for 11 h. The reaction mixture was diluted with ethyl acetate and washed 4× with water, dried and concentrated. The residue was purified using flash chromatography (4 g column; DCM 100%→DCM:MeOH 50:50; 18 ml/min). Finally the HCl salt was formed by adding one equivalent HCl to give (S)-1-(3-(3-(trifluoromethyl)phenylsulfonyl)quinolin-8-yl)piperidin-3-ol hydrochloride (25 mg, yield 9.4%).

LCMS (ESI$^+$) m/z [M+H]$^+$: 437.10

$^1$H NMR (DMSO-d$_6$, 400 MHz): δ=9.35 (d, J=2.4 Hz, 1H), 9.18 (d, J=2.2 Hz, 1H), 8.41-8.45 (m, 2H), 8.13-8.14 (m, 1H), 7.91 (m, 1H), 7.82 (d, J=7.6 Hz, 1H), 7.67 (t, 1H), 7.46 (m, br., 1H), 3.77-3.90 (m, 3H), 2.83 (m, 1H), 2.68 (m, 1H), 2.53 (m, 1H), 1.96 (br m, 1H), 1.82 (m, 1H), 1.72 (m, 1H), 1.34 (m, 1H).

Example 5

(R)-1-[3-(3-Trifluoromethyl-benzenesulfonyl)-quinolin-8-yl]-piperidin-3-ol (R)-Piperidin-3-ol hydrochloride (349 mg, 2.53 mmol) and 8-fluoro-3-(3-(trifluoromethyl)phenylsulfonyl)quinoline (200 mg, 0.563 mmol) were suspended in NMP (2 ml) and $K_2CO_3$ (700 mg, 5.07 mmol) was added and stirred in the Microwave at 225° C. for 30 min. The reaction mixture was diluted with ethyl acetate and washed 4× with water, dried and concentrated. The residue was purified using flash chromatography (12 g column; DCM 100%→DCM:MeOH 60:40; 30 ml/min) to give (R)-1-(3-(3-(trifluoromethyl)phenylsulfonyl)quinolin-8-yl)piperidin-3-ol (140 mg, yield 57%).

LCMS (ESI$^+$) m/z [M+H]$^+$: 437.10

$^1$H NMR (DMSO-d$_6$, 400 MHz): δ=9.32 (d, J=2.4 Hz, 1H), 9.14 (d, J=2.2 Hz, 1H), 8.43 (d, J=8.3 Hz, 1H), 8.41 (s, 1H), 8.12 (d, J=7.8 Hz, 1H), 7.91 (t, J=7.8 Hz, 1H), 7.75 (dd, J=8.2, 0.9 Hz, 1H), 7.64 (t, J=7.8 Hz, 1H), 7.34 (dd, J=7.7, 1.1 Hz, 1H), 4.76 (d, J=4.6 Hz, 1H), 3.73-3.83 (m, 2H), 3.66 (d, J=11.5 Hz, 1H), 2.74 (d, J=2.7 Hz, 1H), 2.57 (m, 1H), 1.97 (dd, J=11.9, 3.5 Hz, 1H), 1.76-1.81 (m, 1H), 1.70 (d, J=11.5 Hz, 1H), 1.30 (dd, J=9.9, 4.3 Hz, 1H).

Example 6

1-[3-(3-Trifluoromethyl-benzenesulfonyl)-quinolin-8-yl]-piperidine-3-carboxylic Acid 8-Fluoro-3-(3-(trifluoromethyl)phenylsulfonyl)quinoline (200 mg, 0.563 mmol) and piperidine-3-carboxylic acid (334 mg, 2.53 mmol) were suspended in NMP (2 ml) and $K_2CO_3$ (311 mg, 2.252 mmol) was added and stirred in the Microwave at 225° C. for 35 min. The reaction mixture was diluted with ethyl acetate and washed 4× with water, dried and concentrated. The residue was purified twice using flash chromatography (12 g column; DCM 100%→DCM:MeOH 60:40; 30 ml/min) to give 1-(3-(3-(trifluoromethyl)phenylsulfonyl)quinolin-8-yl)piperidine-3-carboxylic acid (170 mg, yield 65%).

LCMS (ESI$^+$) m/z [M+H]$^+$: 465.10

$^1$H NMR (DMSO-d$_6$, 500 MHz): δ=12.35 (br s, 1H), 9.34 (d, J=2.4 Hz, 1H), 9.16 (d, J=2.4 Hz, 1H), 8.44 (d, J=8.2 Hz, 1H), 8.42 (s, 1H), 8.11-8.14 (m, J=7.9 Hz, 1H), 7.90 (t, J=7.9 Hz, 1H), 7.78 (d, J=7.6 Hz, 1H), 7.65 (t, J=7.9 Hz, 1H), 7.37-7.39 (m, J=7.3 Hz, 1H), 3.91 (d, J=9.2 Hz, 1H), 3.64 (d, J=11.6 Hz, 1H), 2.85-2.93 (m, 2H), 2.68-2.73 (m, 1H), 1.99-2.05 (m, 1H), 1.80-1.85 (m, 1H), 1.74 (d, J=11.3 Hz, 1H), 1.57 (dd, J=12.4, 3.5 Hz, 1H).

Example 7

4-Methyl-1-[3-[3-(trifluoromethyl)phenyl]sulfonyl-8-quinolyl]piperidin-4-ol Hydrochloride 4-Methylpiperidin-4-ol (292 mg, 2.53 mmol), 8-fluoro-3-(3-(trifluoromethyl)phenyl-sulfonyl)quinoline (200 mg, 0.563 mmol) and $K_2CO_3$ (311 mg, 2.252 mmol) were suspended in NMP (2 ml) and stirred in the Microwave at 225° C. for 35 min. The reaction mixture was diluted with ethyl acetate and washed 4× with water, dried and concentrated. The product was obtained by preparative HPLC chromatography on a reversed phase column. Finally the HCl salt was formed by adding one equivalent HCl to give 4-methyl-1-(3-(3-(trifluoromethyl)phenylsulfonyl)quinolin-8-yl)piperidin-4-ol hydrochloride (97 mg, yield 35.4%).

LCMS (ESI$^+$) m/z [M+H]$^+$: 451.10

$^1$H NMR (DMSO-d$_6$, 500 MHz): δ=9.56 (d, J=2.1 Hz, 1H), 9.44 (d, J=2.1 Hz, 1H), 8.43-8.53 (m, 3H), 8.32 (d, J=8.2 Hz, 1H), 8.17 (d, J=7.9 Hz, 1H), 7.97 (t, J=7.9 Hz, 1H), 7.91 (t, J=7.9 Hz, 1H), 5.32-5.41 (m, broad, 1H), 4.04 (br s, 2H), 3.63 (s, 1H), 3.61 (s, 1H), 2.21 (m, 2H), 1.83 (m, 2H), 1.31 ppm (s, 3H).

Example 8

1-[3-[3-(Trifluoromethyl)phenyl]sulfonyl-8-quinolyl]azetidin-3-ol

3-Azetidinol (191 mg, 2.53 mmol) and 8-fluoro-3-(3-(trifluoromethyl)phenylsulfonyl)-quinoline (200 mg, 0.563 mmol) were suspended in NMP (2 ml) and $K_2CO_3$ (311 mg, 2.252 mmol) was added and stirred in the Microwave at 225° C. for 35 min. The reaction mixture was diluted with ethyl acetate and washed 4× with water, dried and concentrated. The residue was purified using flash chromatography (12 g column; DCM 100%→DCM:ethyl acetate 60:40; 30 ml/min) to give 1-(3-(3-(trifluoromethyl)phenylsulfonyl)quinolin-8-yl)azetidin-3-ol (30 mg, yield 13.1%).

LCMS (ESI$^+$) m/z [M+H]$^+$: 409.10

$^1$H NMR (DMSO-d$_6$, 500 MHz): δ=9.16 (d, J=2.4 Hz, 1H), 9.04 (d, J=2.4 Hz, 1H), 8.43 (d, J=8.2 Hz, 1H), 8.40 (s, 1H), 8.13 (d, J=7.9 Hz, 1H), 7.93 (s, 1H), 7.55 (m, 1H), 7.43 (d, J=7.3 Hz, 1H), 6.73 (d, J=7.0 Hz, 1H), 5.60 (d, J=6.4 Hz, 1H), 4.60 (m, 1H), 4.49-4.53 (m, 2H), 3.92 (dd, J=9.0, 4.7 Hz, 2H).

Example 9

1-[3-(3-Fluorophenyl)sulfonyl-8-quinolyl]piperidin-4-ol

8-Fluoro-3-(3-fluorophenylsulfonyl)quinoline (100 mg, 0.328 mmol) and piperidin-4-ol (16.4 mg, 0.360 mmol) were suspended in NMP and K$_2$CO$_3$ (543 mg, 3.93 mmol) was added and flushed with argon. The reaction mixture was stirred in the Microwave at 180° C. for 80 min. The reaction mixture was filtered through a fritted funnel and concentrated under high vacuo. The residue was dissolved in ethyl acetate and was washed with water and brine. The organic layer was dried with sodium sulfate, filtered and concentrated. The residue was purified twice using flash chromatography (80 g column; n-heptane 100%→n-heptane:ethyl acetate 0:100; 80 g column; DCM 100%→DCM:MeOH 0-100) to give 1-(3-(3-fluorophenylsulfonyl)quinolin-8-yl)piperidin-4-ol (494 mg, yield 46.3%).

LCMS (ESI$^+$) m/z [M+H]$^+$: 387.10

$^1$H NMR (CDCl$_3$, 500 MHz): δ=9.2 (s, 1H), 8.72 (s, 1H), 7.8 (d, 1H), 7.7 (d, 1H), 7.45-7.6 (m, 3H), 7.2-7.35 (m, 2H), 3.95 (s, broad, 1H), 3.7 (m, 2H), 3.0-3.1 (m, 2H), 2.14 (m, 2H), 1.88 (m, 2H).

Example 10

1-[3-(3-Fluorophenyl)sulfonyl-8-quinolyl]azetidin-3-ol

8-Fluoro-3-(3-fluorophenylsulfonyl)quinoline (300 mg, 0.983 mmol), azetidin-3-ol (215 mg, 2.95 mmol) and K$_2$CO$_3$ (163 mg, 1.179 mmol) were suspended in n-propanol (5 ml) and stirred at 100° C. for 24 h. The reaction mixture was concentrated and the residue was dissolved in DCM and water (pH 9) and acidified with 5% NH$_4$Cl to pH 7. The aqueous layer was twice extracted with DCM and the combined organic layers were washed several times with brine, dried with sodium sulfate, filtered and concentrated. The residue was purified using flash chromatography (40 g column; n-heptane 100%→n-heptane:ethyl acetate 10:90) to give 1-(3-(3-fluorophenylsulfonyl)quinolin-8-yl)azetidin-3-ol (17 mg, yield 4.8%).

LCMS (ESI$^+$) m/z [M+H]$^+$: 359.10

$^1$H NMR (CDCl$_3$, 600 MHz): δ=9.04-9.06 (m, 1H), 8.65 (d, J=2.3 Hz, 1H), 7.81 (d, J=7.9 Hz, 1H), 7.67-7.75 (m, 1H), 7.46-7.54 (m, 2H), 7.23-7.31 (m, 2H), 6.67 (d, J=7.7 Hz, 1H), 4.78-4.85 (m, 1H), 4.59-4.66 (m, 2H), 4.06 (dd, J=9.4, 4.5 Hz, 2H).

Example 11

(3S)-1-[3-[3-(Trifluoromethyl)phenyl]sulfonyl-8-quinolyl]pyrrolidine-3-carboxylic Acid 8-Fluoro-3-(3-(trifluoromethyl)phenylsulfonyl)quinoline (200 mg, 0.563 mmol) and (S)-(+)-pyrrolidine-3-carboxylic acid (292 mg, 2.53 mmol) were suspended in NMP (4 ml) and K$_2$CO$_3$ (311 mg, 2.252 mmol) was added and stirred at 225° C. in Microwave for 35 min. The reaction mixture was diluted with ethyl acetate and washed 4× with water, dried and concentrated. The residue was purified using flash chromatography (12 g column; DCM 100%→DCM:MeOH 60:40; 30 ml/min) to give (S)-1-(3-(3-(trifluoromethyl)phenylsulfonyl)quinolin-8-yl)pyrrolidine-3-carboxylic acid (113 mg, yield 44.6%).

LCMS (ESI$^+$) m/z [M+H]$^+$: 451.10

$^1$H NMR (DMSO-d$_6$, 500 MHz): δ=12.48 (br s, 1H), 9.19 (d, J=2.4 Hz, 1H), 9.05 (d, J=2.4 Hz, 1H), 8.46 (d, J=8.2 Hz, 1H), 8.43 (s, 1H), 8.14 (d, J=7.9 Hz, 1H), 7.93 (t, J=7.8 Hz, 1H), 7.54 (t, J=7.9 Hz, 1H), 7.46 (d, J=7.3 Hz, 1H), 6.94 (d, J=7.6 Hz, 1H), 3.99 (d, J=7.0 Hz, 2H), 3.67-3.72 (m, 2H), 3.18 (quin, J=7.3 Hz, 1H), 2.20-2.23 (m, 1H), 2.16-2.19 (m, 1H).

Example 12

(3R)-1-[3-[3-(Trifluoromethyl)phenyl]sulfonyl-8-quinolyl]pyrrolidine-3-carboxylic Acid The title compound was prepared using the procedure described in example 11 starting from (R)-pyrrolidine-3-carboxylic acid (64.8 mg, 0.563 mmol) and 8-fluoro-3-(3-(trifluoromethyl)phenylsulfonyl)quinoline (200 mg, 0.563 mmol) to give (R)-1-(3-(3-(trifluoromethyl)phenylsulfonyl)quinolin-8-yl)pyrrolidine-3-carboxylic acid (141 mg, yield 55.6%).

LCMS (ESI$^+$) m/z [M+H]$^+$: 451.10

$^1$H NMR (DMSO-d$_6$, 500 MHz): δ=12.46 (s, broad, 1H), 9.18 (d, J=2.4 Hz, 1H), 9.04 (d, J=2.4 Hz, 1H), 8.44 (d, J=8.2 Hz, 1H), 8.41 (s, 1H), 8.13 (d, J=7.9 Hz, 1H), 7.92 (t, J=7.8 Hz, 1H), 7.53-7.55 (m, 1H), 7.45 (d, J=7.6 Hz, 1H), 6.95 (d, J=7.6 Hz, 1H), 3.98 (d, J=7.3 Hz, 2H), 3.70 (t, J=6.9 Hz, 2H), 3.17 (t, J=7.2 Hz, 1H), 2.14-2.24 (m, 2H).

Example 13

1-[3-(3-Methoxyphenyl)sulfonyl-8-quinolyl]piperidin-4-ol

Sodium sulfite (1.83 g, 14.52 mmol) was dissolved in water (16 ml) and warmed up to 75° C. 3-Methoxybenzene-1-sulfonyl chloride (3 g, 14.52 mmol) was added over 30 min. The reaction mixture was stirred at 80° C. for 7 h and at room temperature overnight and subsequently concentrated. The residue was suspended in MeOH and the precipitate was filtered and washed with MeOH and concentrated to give sodium 3-methoxybenzenesulfinate (2.7 g, yield 96%).

8-Fluoro-3-iodoquinoline (1.406 g, 5.15 mmol), sodium 3-methoxybenzenesulfinate (1 g, 5.15 mmol) and copper(I) trifluoromethanesulfonate benzene complex (2.88 g, 5.15 mmol) were suspended in DMF (20 ml) and warmed up to 65° C. for 4 h. The reaction mixture was stirred at room temperature over the weekend. The reaction mixture was filtered over a fritted funnel and concentrated. The residue was dissolved in DCM and washed several times with 2% aqueous NH$_3$-solution and then several times with brine until neutral. The organic layer was dried with sodium sulfate, filtered and concentrated to give 8-fluoro-3-(3-methoxyphenylsulfonyl)quinoline (1.37 g, yield 80%, purity 95%).

8-Fluoro-3-(3-methoxyphenylsulfonyl)quinoline (300 mg, 0.945 mmol) and piperidin-4-ol (430 mg, 4.25 mmol) were suspended in NMP (8 ml) and K$_2$CO$_3$ (523 mg, 3.78 mmol) was added and flushed with argon. The reaction mixture was stirred in the Microwave at 225° C. for 40 min. The reaction mixture was filtered through a fritted funnel and concentrated under high vacuo. The residue was dissolved in ethyl acetate and 5% NH$_4$Cl-solution was added until pH 7 and washed several times with brine. The organic layer was dried with sodium sulfate, filtered and concentrated. The residue was purified using flash chromatography (40 g column; DCM 100%→DCM:MeOH 0:100; 40 ml/min). The crude material was purified using Chromabond flash chromatography to give 1-(3-(3-methoxyphenylsulfonyl)quinolin-8-yl)piperidin-4-ol (52 mg, yield 13.1%. purity 95%).

LCMS (ESI$^+$) m/z [M+H]$^+$: 399.10

$^1$H NMR (CDCl$_3$, 500 MHz): δ=9.22 (m, 1H), 8.74 (m, 1H), 7.5-7.7 (m, 4H), 7.41 (m, 1H), 7.26 (s, broad, 1H), 7.09 (dd, J=8.4, 2.0 Hz, 1H), 3.95 (m, 1H), 3.85 (s, 3H), 3.70 (br m, 2H), 3.07 (br m, 2H), 2.13 (br m, 2H), 1.91 (m, broad, 2H).

Example 14

1-[3-(3-Methoxyphenyl)sulfonyl-8-quinolyl]azetidin-3-ol

Sodium sulfite (1.83 g, 14.52 mmol) was dissolved in water (16 ml) and warmed up to 75° C. 3-Methoxybenzene-1-sulfonyl chloride (3 g, 14.52 mmol) was added over 30 min. The reaction mixture was stirred at 80° C. for 7 h and at room temperature overnight and subsequently concentrated. The residue was suspended in MeOH and the precipitate was filtered and washed with MeOH and concentrated to give sodium 3-methoxybenzenesulfinate (2.7 g, yield 96%).

8-Fluoro-3-iodoquinoline (1.406 g, 5.15 mmol), sodium 3-methoxybenzenesulfinate (1 g, 5.15 mmol) and copper(I) trifluoromethanesulfonate benzene complex (2.88 g, 5.15 mmol) were suspended in DMF (20 ml) and warmed up to 65° C. for 4 h. The reaction mixture was stirred at room temperature over the weekend. The reaction mixture was filtered over a fritted funnel and concentrated. The residue was dissolved in DCM and washed several times with 2% aqueous NH$_3$-solution and then several times with brine until neutral. The organic layer was dried with sodium sulfate, filtered and concentrated to give 8-fluoro-3-(3-methoxyphenylsulfonyl)quinoline (1.37 g, yield 80%, purity 95%).

8-Fluoro-3-(3-methoxyphenylsulfonyl)quinoline (200 mg, 0.630 mmol) and azetidin-3-ol (207 mg, 2.84 mmol) were suspended in NMP (8 ml) and K$_2$CO$_3$ (348 mg, 2.52 mmol) was added and flushed with argon. The reaction mixture was stirred in the Microwave at 225° C. for 40 min and subsequently concentrated under high-vacuum. The residue was dissolved in ethyl acetate and washed with water and brine. The organic layer was dried with sodium sulfate, filtered and concentrated. The residue was purified using flash chromatography (40 g column). The crude material was purified twice using Chromabond flash chromatography to give 1-(3-(3-methoxyphenylsulfonyl)quinolin-8-yl)azetidin-3-ol (76.8 mg, yield 31.3%, purity 95%).

LCMS (ESI$^+$) m/z [M+H]$^+$: 371.10

$^1$H NMR (CDCl$_3$, 500 MHz): δ=9.04 (d, J=2.4 Hz, 1H), 8.64 (d, J=2.1 Hz, 1H), 7.57 (d, J=7.9 Hz, 1H), 7.50-7.51 (m, 1H), 7.48 (s, 1H), 7.42 (s, 1H), 7.26 (s, 1H), 7.09 (dd, J=8.2, 1.8 Hz, 1H), 6.65 (s, 1H), 4.62 (m, 1H), 4.06 (m, 1H), 3.85 (s, 3H), 1.59 (br s, 1H), 1.25 (s, 1H).

Example 15

1-[3-(3-Methoxyphenyl)sulfonyl-8-quinolyl]piperidine-4-carboxylic Acid

Sodium sulfite (1.83 g, 14.52 mmol) was dissolved in water (16 ml) and warmed up to 75° C. 3-Methoxybenzene-1-sulfonyl chloride (3 g, 14.52 mmol) was added over 30 min. The reaction mixture was stirred at 80° C. for 7 h and at room temperature overnight and subsequently concentrated. The residue was suspended in MeOH and the precipitate was filtered and washed with MeOH and concentrated to give sodium 3-methoxybenzenesulfinate (2.7 g, yield 96%).

8-Fluoro-3-iodoquinoline (1.406 g, 5.15 mmol), sodium 3-methoxybenzenesulfinate (1 g, 5.15 mmol) and copper(I) trifluoromethanesulfonate benzene complex (2.88 g, 5.15 mmol) were suspended in DMF (20 ml) and warmed up to 65° C. for 4 h. The reaction mixture was stirred at room temperature over the weekend. The reaction mixture was filtered over a fitted funnel and concentrated. The residue was dissolved in DCM and washed several times with 2% aqueous NH$_3$-solution and then several times with brine until neutral. The organic layer was dried with sodium sulfate, filtered and concentrated to give 8-fluoro-3-(3-methoxyphenylsulfonyl)quinoline (1.37 g, yield 80%, purity 95%).

The title compound was prepared using the procedure described in example 15 starting from 8-fluoro-3-(3-methoxyphenylsulfonyl)quinoline (200 mg, 0.630 mmol) and piperidine-4-carboxylic acid (366 mg, 2.84 mmol) to give 1-(3-(3-methoxyphenylsulfonyl)quinolin-8-yl)piperidine-4-carboxylic acid (14.6 mg, yield 5.2%, purity 95%).

LCMS (ESI$^+$) m/z [M+H]$^+$: 427.10

Example 16

1-[3-[[8-(4-Hydroxy-1-piperidyl)-3-quinolyl]sulfonyl]phenyl]piperidin-4-ol

8-Fluoro-3-iodoquinoline (4 g, 14.65 mmol), sodium 3-fluorobenzenesulfinate (4.8 g, 26.4 mmol) and copper(I) trifluoromethanesulfonate benzene complex (8.19 g, 14.65 mmol) were suspended in DMF (80 ml) and warmed up to 65° C. for 4 h. The reaction mixture was stirred at room temperature over the weekend. The reaction mixture was filtered over a fritted funnel and concentrated. The residue was dissolved in DCM and washed several times with 2% aqueous NH$_3$-solution and then several times with brine until neutral. The organic layer was dried with sodium sulfate, filtered and concentrated. The residue was purified using flash chromatography (120 g column; DCM 100%→DCM:MeOH 85:15). The crude material was purified using Chromabond flash chromatography to give 8-fluoro-3-(3-fluorophenylsulfonyl)quinoline (1.4 g, yield 29.7%).

8-fluoro-3-(3-fluorophenylsulfonyl)quinoline (600 mg, 1.966 mmol) and piperidin-4-ol (894 mg, 8.84 mmol) were suspended in NMP (16 ml) and K₂CO₃ (1.086 g, 7.86 mmol) was added and flushed with argon. The reaction mixture was stirred in the Microwave at 225° C. for 40 min and subsequently concentrated under high-vacuum. The residue was purified using flash chromatography (80 g column; DCM 100%→DCM:MeOH 90:10) to give 1-(3-(3-(4-hydroxypiperidin-1-yl)phenylsulfonyl)quinolin-8-yl)piperidin-4-ol (122 mg, yield 13.3%).

LCMS (ESI⁺) m/z [M+H]⁺: 468.20

¹H NMR (CDCl₃, 500 MHz): δ=9.22 (br s, 1H), 8.73 (br s, 1H), 7.5–7.65 (m, 3H), 7.29–7.39 (m, 3H), 7.07 (d, J=7.0 Hz, 1H), 3.85–4.0 (br m, 2H), 3.71 (br m, 2H), 3.57–3.63 (m, broad, 2H), 2.99–3.09 (m, broad, 2H), 2.13 (br. m., 2H), 1.96–2.04 (m, 2H), 1.92 (br m, 2H), 1.64–1.71 (m, 2H), 1.49 (br m, 2H).

Example 17

1-[3-[[8-(4-Carboxy-1-piperidyl)-3-quinolyl]sulfonyl]phenyl]piperidine-4-carboxylic Acid 8-Fluoro-3-(3-fluorophenylsulfonyl)quinoline (200 mg, 0.655 mmol) and piperidine-4-carboxylic acid (381 mg, 2.95 mmol) were suspended in NMP (8 ml) and K₂CO₃ (362 mg, 2.62 mmol) was added and flushed with argon. The reaction mixture was stirred in the Microwave at 225° C. for 40 min and subsequently concentrated under high-vacuum. The residue was dissolved in ethyl acetate and washed with water. The aqueous layer was acidified with 1M HCl to pH 4 and extracted several times with ethyl acetate. The combined organic layers were washed with brine, dried with sodium sulfate, filtered and concentrated. The residue was purified using flash chromatography (40 g column). The crude material was purified using Chromabond flash chromatography to give 1-(3-(3-(4-carboxypiperidin-1-yl)phenylsulfonyl)quinolin-8-yl)piperidine-4-carboxylic acid (9.8 mg, yield 2.7%).

LCMS (ESI⁺) m/z [M+H]⁺: 524.20

¹H NMR (DMSO-d₆, 500 MHz): δ=12.23 (br s, 2H), 9.25 (s, 1H), 9.04 (s, 1H), 7.75 (d, J=7.9 Hz, 1H), 7.62 (t, J=7.6 Hz, 1H), 7.50 (s, 1H), 7.42 (d, J=8.2 Hz, 1H), 7.38–7.40 (m, 1H), 7.33 (d, J=7.6 Hz, 1H), 7.25 (d, J=8.5 Hz, 1H), 3.75 (d, J=11.3 Hz, 4H), 2.85 (t, J=11.7 Hz, 4H), 2.44 (d, J=7.0 Hz, 2H), 1.88–1.98 (m, 4H), 1.83 (d, J=11.0 Hz, 2H), 1.61 (d, J=10.7 Hz, 2H).

Example 18

1-[3-(Benzenesulfonyl)-8-quinolyl]piperidin-4-ol

Sodium hydrogencarbonate (3.81 g, 45.3 mmol) and sodium sulfite (2.85 g, 22.65 mmol) were dissolved in water (20 ml) and warmed up to 75° C. Benzenesulfonyl chloride (2.89 ml, 22.65 mmol) was added in 30 min and stirred at 80° C. for 7 h and at room temperature over the weekend. The reaction mixture was concentrated and dissolved in MeOH (20 ml), stirred, filtered and concentrated to give sodium benzenesulfinate (4.1 g, yield 99%, purity 90%).

8-Fluoro-3-iodoquinoline (2.99 g, 10.97 mmol), sodium benzenesulfinate (2 g, 10.97 mmol) and copper(I) trifluoromethanesulfonate benzene complex (5.52 g, 10.97 mmol) were dissolved in DMF (40 ml) and warmed up to 65° C. and stirred for 6 h. The reaction mixture stirred at room temperature overnight. The reaction mixture was filtered over a fitted funnel and concentrated. The residue was dissolved in DCM and washed 3× with NH₄OH-solution. The organic layer was dried, filtered and concentrated to give 8-fluoro-3-(phenylsulfonyl)quinoline (3.4 g, yield 97%, purity 90%).

The title compound was prepared using the procedure described in example 14 starting from piperidin-4-ol (562 ing, 5.56 mmol) and 8-fluoro-3-(phenylsulfonyl)quinoline (355 mg, 1.236 mmol) to give 1-(3-(phenylsulfonyl)quinolin-8-yl)piperidin-4-ol (188 mg, yield 41.3%).

LCMS (ESI⁺) m/z [M+H]⁺: 369.10

¹H NMR (CDCl₃, 500 MHz): δ=9.23 (br s, 1H), 8.76 (br s, 1H), 8.02 (d, J=7.9 Hz, 2H), 7.51–7.59 (m, 5H), 3.94 (m, broad, 1H), 3.71 (br m, 2H), 3.08 (br m, 2H), 2.14 (br m, 2H), 1.92 (br m, 2H).

Example 19

(3R)-1-[3-[3-(Trifluoromethyl)phenyl]sulfonyl-8-quinolyl]pyrrolidin-3-ol

The title compound was prepared using the procedure described in example 11 starting from 8-fluoro-3-(3-(trifluoromethyl)phenylsulfonyl)quinoline (150 mg, 0.422 mmol) and (R)-pyrrolidin-3-ol (166 mg, 1.900 mmol) to give (R)-1-(3-(3-(trifluoromethyl)phenylsulfonyl)quinolin-8-yl)pyrrolidin-3-ol (31 mg, yield 17.4%).

LCMS (ESI⁺) m/z [M+H]⁺: 423.10

¹H NMR (CDCl₃, 500 MHz): δ=9.06 (d, J=2.1 Hz, 1H), 8.68 (d, J=2.1 Hz, 1H), 8.29 (s, 1H), 8.19–8.22 (m, J=7.9 Hz, 1H), 7.84 (d, J=7.9 Hz, 1H), 7.67–7.71 (m, 1H), 7.50 (t, J=7.9 Hz, 1H), 7.25–7.28 (m, 1H), 6.91–6.94 (m, J=7.6 Hz, 1H), 4.62 (br s, 1H), 4.14 (dd, J=11.9, 4.6 Hz, 1H), 3.92–3.98 (m, 1H), 3.78 (d, J=11.9 Hz, 1H), 3.64–3.69 (m, 1H), 2.19 (m, 1H), 2.09 (m, 1H).

Example 20

(3R)-1-[3-(3-Fluorophenyl)sulfonyl-8-quinolyl]piperidin-3-ol 2,2-Bis(diphenylphosphino)-1,1-binapthyl (BINAP) (15.07 mg, 0.024 mmol), tris(dibenzylideneacetone)dipalladium(0) (11.08 mg, 0.012 mmol), cesium carbonate (867 mg, 2.66 mmol) and (R)-piperidin-3-ol (171 mg, 1,694 mmol) were added and flushed with argon overnight. Then degassed toluene (10 ml) was added and stirred at 50° C. for 10 min. Finally 3-(3-fluorophenylsulfonyl)-8-iodoquinoline (500 mg, 1.210 mmol) was added and stirred at 100° C. overnight. The reaction mixture was concentrated. The residue was dissolved in DCM and water and the aqueous layer was acidified with 0.1M HCl (pH 7). The organic layer was washed several times with water and finally with brine, dried with sodium sulfate, filtered and concentrated. The residue was purified using flash chromatography (40 g column; DCM 100%→DCM:MeOH 90:10) to give (R)-1-(3-(3-fluorophenylsulfonyl)quinolin-8-yl)piperidin-3-ol (170 mg, yield 34.5%, purity 95%).

LCMS (ESI⁺) m/z [M+H]⁺: 387.10

¹H NMR (CDCl₃, 600 MHz): δ=9.18 (d, J=1.9 Hz, 1H), 8.76–8.79 (m, 1H), 7.83 (d, J=7.9 Hz, 1H), 7.72 (d, J=7.7 Hz, 1H), 7.51–7.60 (m, 3H), 7.2–7.35 (several m, 2H), 4.13–4.17 (m, very broad, 1H), 4.09 (br s, 1H), 3.69 (m, 1H), 3.32 (m, 1H), 3.22 (m, 1H), 3.14 (m, 1H), 2.15 (m, 1H), 1.87–1.93 (m, 1H), 1.68–1.76 (m, 2H).

Example 21

1-[3-(2-Methoxyphenyl)sulfonyl-8-quinolyl]piperidin-4-ol

The title compound was prepared using the procedure described in example 13 starting from 8-fluoro-3-(2- methoxyphenylsulfonyl)quinoline (400 mg, 1.260 mmol) and piperidin-4-ol (574 mg, 5.67 mmol) to give 1-(3-(2-methoxyphenylsulfonyl)quinolin-8-yl)piperidin-4-ol (22.4 mg, yield 4.2%, purity 95%).

LCMS (ESI$^+$) m/z [M+H]$^+$: 399.10

$^1$H NMR (CDCl$_3$, 600 MHz): δ=9.22 (br s, 1H), 8.80 (br s, 1H), 8.22-8.25 (m, J=7.7 Hz, 1H), 7.52-7.60 (m, 3H), 7.30 (br s, 1H), 7.15 (t, J=7.6 Hz, 1H), 6.87-6.91 (m, J=8.3 Hz, 1H), 3.95 (br s, 1H), 3.75 (s, 4H), 3.08 (br s, 2H), 2.12-2.18 (m, 2H), 1.92 (m, 2H), 1.49 (br m, 1H).

Example 22

(3S)-1-[3-(Benzenesulfonyl)-8-quinolyl]piperidin-3-ol

The title compound was prepared using the procedure described in example 18 to give (S)-1-(3-(phenylsulfonyl)quinolin-8-yl)piperidin-3-ol (220 mg, yield 54.3%, purity 95%).

LCMS (ESI$^+$) m/z [M+H]$^+$: 369.10

$^1$H NMR (CDCl$_3$, 600 MHz): δ=9.18 (s, 1H), 8.78 (s, 1H), 8.03 (m, 2H), 7.59-7.62 (m, 1H), 7.5-7.6 (m, 4H), 7.25 (m, 1H), 4.21 (br s, 1H), 4.08 (br m, 1H), 3.69 (m, 1H), 3.32 (m, 1H), 3.21 (m, 1H), 3.13 (m, 1H), 2.15 (m, 1H), 1.87-1.93 (m, 1H), 1.67-1.75 (m, 2H).

Example 23

(3R)-1-[3-(Benzenesulfonyl)-8-quinolyl]piperidin-3-ol

The title compound was prepared using the procedure described in example 18 to give (R)-1-(3-(phenylsulfonyl)quinolin-8-yl)piperidin-3-ol (163 mg, yield 42.4%).

LCMS (ESI$^+$) m/z [M+H]$^+$: 369.10

$^1$H NMR (CDCl$_3$, 600 MHz): δ=9.18 (s, 1H), 8.78 (s, 1H), 8.03 (m, 2H), 7.59-7.62 (m, 1H), 7.54 (m, 4H), 7.26 (m, 1H), 4.21 (br s, 1H), 4.08 (br m, 1H), 3.69 (m, 1H), 3.32 (m, 1H), 3.21 (m, 1H), 3.13 (m, 1H), 2.15 (m, 1H), 1.87-1.94 (m, 1H), 1.67-1.75 (m, 2H).

Example 24

1-[3-[(8-Fluoro-3-quinolyl)sulfonyl]phenyl]piperidin-4-ol

8-Fluoro-3-(3-fluorophenylsulfonyl)quinoline (100 mg, 0.328 mmol) and piperidin-4-ol (16.4 mg, 0.360 mmol) were suspended in NMP (25 ml) and K$_2$CO$_3$ (543 mg, 3.93 mmol) was added and flushed with argon. The reaction mixture was stirred at 180° C. for 80 min and then filtered over a fitted funnel and concentrated under high-vacuum. The residue was dissolved in ethyl acetate and washed with water and brine. The organic layer was dried with sodium sulfate, filtered and concentrated. The residue was purified twice using flash chromatography (80 g column; DCM 100%→DCM:MeOH 0:100; 80 g column; cyclohexane 100%→cyclohexane:ethyl acetate 0-100). The crude product was purified using Chromabond flash chromatography to give 1-(3-(8-fluoroquinolin-3-ylsulfonyl)phenyl)piperidin-4-ol (28 mg, yield 2.5%, purity 92%).

LCMS (ESI$^+$) m/z [M+H]$^+$: 387.10

$^1$H NMR (CDCl$_3$, 600 MHz): δ=9.32 (d, J=1.7 Hz, 1H), 8.83 (s, 1H), 7.78 (d, J=8.3 Hz, 1H), 7.64 (m, 1H), 7.51-7.59 (m, 2H), 7.38 (m, 2H), 7.26 (s, 8H), 7.12 (br m, 1H), 3.92 (br m, 1H), 3.60-3.64 (m, 2H), 3.05 (m, 2H), 2.02 (br m, 2H), 1.66-1.71 (m, 2H).

Example 25

1-[2-[(8-Fluoro-3-quinolyl)sulfonyl]phenyl]piperidin-4-ol

The title compound was prepared using the procedure described in example 25 starting with 8-fluoro-3-(2-fluorophenylsulfonyl)quinoline (500 mg, 1.638 mmol) and piperidin-4-ol (182 mg, 1.802 mmol) to give 1-(2-(8-fluoroquinolin-3-ylsulfonyl)phenyl)-piperidin-4-ol (238 mg, yield 37.6%).

LCMS (ESI$^+$) m/z [M+H]$^+$: 387.10

$^1$H NMR (DMSO-d$_6$, 600 MHz): δ=9.28 (d, J=1.9 Hz, 1H), 9.03 (s, 1H), 8.26 (d, J=7.9 Hz, 1H), 8.10 (d, J=8.1 Hz, 1H), 7.79-7.83 (m, 1H), 7.75-7.79 (m, 2H), 7.54 (t, J=7.6 Hz, 1H), 7.49 (d, J=7.9 Hz, 1H), 4.66 (br s, 1H), 3.51 (br s, 1H), 2.66 (br m, 2H), 2.49-2.57 (m, 1H), 1.58 (d, J=9.8 Hz, 2H), 1.27-1.35 (m, 2H).

Example 26

(3S)-1-[3-(3-Fluorophenyl)sulfonyl-8-quinolyl]pyrrolidin-3-ol 2,2-Bis(diphenylphosphino)-1,1-binapthyl (BINAP) (7.53 mg, 0.012 mmol), tris(dibenzylideneacetone)dipalladium(0) (11.08 mg, 0.012 mmol), cesium carbonate (867 mg, 2.66 mmol) and 3-(3-fluorophenylsulfonyl)-8-iodoquinoline (500 mg, 1.210 mmol), were added and flushed with argon for 6 h. Then degassed toluene (10 ml) was added and stirred at 50° C. for 10 min. Finally 3-(3-fluorophenylsulfonyl)-8-iodoquinoline (105 mg, 1.210 mmol) was added and stirred at 100° C. over the weekend. The reaction mixture was concentrated. The residue was dissolved in DCM and water. The aqueous layer was washed twice with DCM. The combined organic layers were washed with brine, dried with sodium sulfate, filtered and concentrated. The residue was purified twice using flash chromatography (24 g column; DCM 100%→DCM:MeOH 90:10) to give (S)-1-(3-(3-fluorophenylsulfonyl)quinolin-8-yl)pyrrolidin-3-ol (148 mg, yield 31.2%, purity 95%).

LCMS (ESI$^+$) m/z [M+H]$^+$: 373.10

$^1$H NMR (CDCl$_3$, 500 MHz): δ=9.02 (s, 1H), 8.57 (s, 1H), 7.9 (d, 1H), 7.7 (1, 1H), 7.45-7.6 (m, 2H), 7.2-7.3 (m, 2H), 6.9 (m, broad, 1H), 4.6 (m, broad, 1H), 4.1 (m, 1H), 3.95 (m, 1H), 3.75 (m, 1H), 3.65 (m, 1H), 2.7 (m, 1H), 2.6 (m, 1H).

Example 27

(3S)-1-[3-(3-Fluorophenyl)sulfonyl-8-quinolyl]piperidin-3-ol

The title compound was prepared using the procedure described in example 20 starting from 3-(3-fluorophenylsulfonyl)-8-iodoquinoline (500 mg, 1.210 mmol) and (S)-piperidin-3-ol (171 mg, 1.694 mmol) to give (S)-1-(3-(3-fluorophenylsulfonyl)quinolin-8-yl)piperidin-3-ol (32.5 mg, yield 6.4%, purity 92%).

LCMS (ESI$^+$) m/z [M+H]$^+$: 387.10

$^1$H NMR (CDCl$_3$, 600 MHz): δ=9.20 (br s, 1H), 8.79 (br s, 1H), 7.83 (d, J=7.7 Hz, 1H), 7.72 (d, J=7.5 Hz, 1H), 7.60 (br s, 1H), 7.52-7.58 (m, 2H), 7.31 (t, J=7.7 Hz, 1H), 7.26

(m, 1H), 4.11 (br s, 1H), 3.69 (br s, 1H), 3.0-3.45 (m, broad, 3H), 2.17 (m, broad, 1H), 1.91 (br s, 1H), 1.74 (br s, 2H).

Example 28

1-[3-(2-Hydroxy-5-methyl-phenyl)sulfonyl-8-quinolyl]piperidin-4-ol

The title compound was prepared using the procedure described in example 14 starting from 8-fluoro-3-(2-methoxy-5-methylphenylsulfonyl)quinoline (400 mg, 1.207 mmol), piperidin-4-ol (549 mg, 5.43 mmol) to give 1-(3-(2-hydroxy-5-methylphenylsulfonyl)-quinolin-8-yl)piperidin-4-ol (62.5 mg, yield 12.3%, purity 95%).

LCMS (ESI$^+$) m/z [M+H]$^+$: 399.10

$^1$H NMR (DMSO-d$_6$, 600 MHz): δ=10.70 (br s, 1H), 9.13-9.15 (s, 1H), 8.93 (s, 1H), 7.80 (s, 1H), 7.75 (d, J=8.1 Hz, 1H), 7.59 (t, J=7.9 Hz, 1H), 7.32 (m, 2H), 6.77 (d, J=7.9 Hz, 1H), 4.70-4.73 (m, 1H), 3.63-3.71 (m, 3H), 2.94 (m, 2H), 2.31 (s, 3H), 1.91 (d, J=10.4 Hz, 2H), 1.65 (q, J=9.1 Hz, 2H).

Example 29

1-[3-[3-(Difluoromethoxy)phenyl]sulfonyl-8-quinolyl]piperidin-4-ol

Sodium hydrogencarbonate (1.385 g, 16.49 mmol) and sodium sulfite (1.039 g, 8.24 mmol) were dissolved in water (10 ml) and warmed up to 75° C. for 30 min. 3-(Difluoromethoxy)benzene-1-sulfonyl chloride (2 g, 8.24 mmol) was added dropwise in 30 min and warmed up to 80° C. for 6 h. The reaction mixture was stirred at room temperature overnight. The reaction mixture was concentrated and dried under high-vacuum. The residue was suspended twice in MeOH (10 ml) and stirred for 10 min. The solid was filtered. The filtrates were combined and concentrated to give sodium 3-(difluoromethoxy)benzenesulfinate (1.206 g, yield 63.6%).

8-Fluoro-3-iodoquinoline (1.431 g, 5.24 mmol), copper (I)trifluoromethanesulfonate benzene complex (2.64 g, 5.24 mmol) and sodium 3-(difluoromethoxy)benzenesulfinate (1.206 g, 5.24 mmol) were suspended in DMF (20 ml) and warmed up to 65° C. for 6 h. The reaction mixture was stirred at room temperature over the weekend. The reaction mixture was filtered over a fritted funnel and washed with DCM. The filtrates were combined and concentrated. The residue was purified using flash chromatography (40 g column; DCM 100%→DCM:MeOH 20:80). One part of the product crystallized over 3 weeks. These crystals were filtered and washed with MeOH and dried under vacuum. The filtrate was concentrated and twice purified using flash chromatography to give 3-(3-(difluoromethoxy)phenylsulfonyl)-8-fluoroquinoline (1.83 g, yield 99%). 3-(3-(Difluoromethoxy)phenylsulfonyl)-8-fluoroquinoline (270 mg, 0.764 mmol), piperidin-4-ol (348 mg, 3.44 mmol) and cesium carbonate (996 mg, 3.06 mmol) were suspended in NMP (5 ml) and flushed with argon and stirred at 210° C. for 30 min. Silica gel was added and purified using flash chromatography (80 g column; DCM 100%→DCM:MeOH 20:80). The crude product was dissolved in ethyl acetate and washed 3× with water. The organic layer was dried and concentrated and purified by preparative HPLC chromatography on a reversed phase column to give 1-(3-(3-(difluoromethoxy)-phenylsulfonyl)quinolin-8-yl)piperidin-4-ol (24 mg, yield 7.2%)

LCMS (ESI$^+$) m/z [M+H]$^+$: 435.10

$^1$H NMR (CDCl$_3$, 600 MHz): δ=9.33-9.35 (m, 1H), 8.91-8.94 (m, 1H), 8.08 (d, J=8.1 Hz, 1H), 7.89 (d, J=7.3 Hz, 1H), 7.80 (br m, 2H), 7.77 (br m, 1H), 7.59 (m, 1H), 7.41 (m, 1H), 6.59 (t, 1H), 4.47 (br s, 2H), 4.30 (br m, 1H), 3.80 (br m, 2H), 2.62 (br m, 2H), 2.15 (br m, 2H).

Example 30

(3S)-1-[3-(Benzenesulfonyl)-8-quinolyl]pyrrolidin-3-ol

The title compound was prepared using the procedure described in example 6 starting from 8-fluoro-3-(phenylsulfonyl)quinoline (300 mg, 1.044 mmol) and (S)-(−)-3-pyrrolidinol (409 mg, 4.70 mmol) to give (S)-1-(3-(phenylsulfonyl)quinolin-8-yl)pyrrolidin-3-ol (150 mg, yield 38.1%, purity 94%).

LCMS (ESI$^+$) m/z [M+H]$^+$: 355.10

$^1$H NMR (CDCl$_3$, 600 MHz): δ=9.07 (br s, 1H), 8.67 (br s, 1H), 8.02 (m, 2H), 7.59 (m, 1H), 7.47-7.56 (m, 3H), 7.26 (m, 1H), 6.92 (br s, 1H), 4.62 (br m, 1H), 4.13 (br m, 1H), 3.92-3.99 (m, 1H), 3.77 (m, 1H), 3.66 (br m, 1H), 2.21 (br m, 1H), 2.10 (br m, 1H).

Example 31

1-[3-[3-(Difluoromethoxy)phenyl]sulfonyl-8-quinolyl]piperidine-4-carboxylic Acid The title compound was prepared using the procedure described in example 29 to give 1-(3-(3-(difluoromethoxy)phenylsulfonyl)quinolin-8-yl)piperidine-4-carboxylic acid (52.2 mg, yield 14.8%).

LCMS (ESI$^+$) m/z [M+H]$^+$: 463.10

$^1$H NMR (DMSO-d$_6$, 600 MHz): δ=12.26 (br s, 1H), 9.29 (br s, 1H), 9.10 (br s, 1H), 7.98 (m, 1H), 7.88 (br s, 1H), 7.77 (m, 1H), 7.72 (m, 1H), 7.64 (m, 1H), 7.54 (m, 1H), 7.41 (t, 1H), 7.35 (m, 1H), 3.77 (m, 2H), 2.86 (m, 2H), 2.45 (m, 1H), 1.96 (m, 2H), 1.82 (m, 2H).

Example 32

(3S,4S)-1-[3-(Benzenesulfonyl)-8-quinolyl]pyrrolidine-3,4-diol 2,2-Bis(diphenylphosphino)-1,1-binapthyl (BINAP) (6.30 mg, 10.12 µmol), tris(dibenzylideneacetone)dipalladium(0) (9.27 mg, 10.12 µmol), cesium carbonate (725 mg, 2.227 mmol) and 8-iodo-3-(phenylsulfonyl)quinoline (400 mg, 1.012 mmol), were added and flushed with argon for 3 h. Then trans-3,4-dihydroxypyrrolidin (104 mg, 1.012 mmol) was dissolved in degassed DMF (5 ml) and added to the reaction mixture. The reaction mixture was stirred at 100° C. over the weekend and subsequently filtered over a fitted funnel and concentrated under high-vacuum. The residue was dissolved in ethyl acetate and acidified with 5% NH$_4$Cl-solution to pH 7, washed with water and several times with brine. The organic layer was dried with sodium sulfate, filtered and concentrated. The residue was purified using flash chromatography (12 g column; DCM 100%→DCM:MeOH 80:20). The crude product was purified using Chromabond flash chromatography to give trans-1-(3-(phenylsulfonyl)quinolin-8-yl)pyrrolidine-3,4-diol (9.8 mg, yield 2.6%).

LCMS (ESI$^+$) m/z [M+H]$^+$: 371.10

¹H NMR (CDCl₃, 600 MHz): δ=9.07 (s, 1H), 8.70 (s., 1H), 7.97-8.05 (m, 2H), 7.5-7.7 (several m, 5H), 7.36 (br s, 1H), 4.37 (br m, 2H), 4.23-4.26 (m, 2H), 3.72 (m, 2H).

Example 33

(3R)-1-[3-(3-Fluorophenyl)sulfonyl-8-quinolyl]pyrrolidin-3-ol

The title compound was prepared using the procedure described in example 26 starting from 3-(3-fluorophenylsulfonyl)-8-iodoquinoline (200 mg, 0.484 mmol) and (R)-pyrrolidin-3-ol (42.2 mg, 0.484 mmol) to give (R)-1-(3-(3-fluorophenylsulfonyl)-quinolin-8-yl)pyrrolidin-3-ol (9.1 mg, yield 4.7%, purity 93%).
LCMS (ESI⁺) m/z [M+H]⁺: 373.10
¹H NMR (CDCl₃, 600 MHz): δ=9.05 (s, 1H), 8.66 (br s, 1H), 7.81 (m, 1H), 7.72 (m, 1H), 7.48-7.56 (m, 2H), 7.23-7.31 (m, 2H), 6.94 (br s, 1H), 4.62 (br m, 1H), 4.09-4.17 (m, 1H), 3.92-3.99 (m, 1H), 3.77 (m, 1H), 3.66 (br m, 1H), 2.24-2.27 (m, 1H), 2.09 (m, 1H).

Example 34

(3R,4R)-1-[3-(Benzenesulfonyl)-8-quinolyl]piperidine-3,4-diol

The title compound was prepared using the procedure described in example 32 starting from 8-iodo-3-(phenylsulfonyl)quinoline (400 mg, 1,012 mmol) and (3S,4S)-pyrrolidine-3,4-diol (110 mg, 1,012 mmol) to give (3R,4R)-1-(3-(phenylsulfonyl)quinolin-8-yl)piperidine-3,4-diol (42 mg, yield 10.8%).
LCMS (ESI⁺) m/z [M+H]⁺: 385.10

Example 35

1-[3-(2-Methoxy-5-methyl-phenyl)sulfonyl-8-quinolyl]piperidin-4-ol

8-Fluoro-3-(2-methoxy-5-methylphenylsulfonyl)quinoline (200 mg, 0.604 mmol), piperidin-4-ol (61 mg, 0.604 mmol) and K₂CO₃ (100 mg, 0.724 mmol) were suspended in n-propanol and stirred at 100° C. for 24 h. The reaction mixture was concentrated and dissolved in DCM and water. The aqueous layer was twice washed with DCM. The organic layer was acidified with 5% NH₄Cl-solution (pH 7), washed with brine, dried with sodium sulfate, filtered and concentrated. The residue was purified twice using flash chromatography (12 g column; n-heptane 100%→n-heptane:ethyl acetate 0:100) to give 1-(3-(2-methoxy-5-methylphenylsulfonyl)quinolin-8-yl)piperidin-4-ol (10.5 mg, yield 4%, purity 95%).
LCMS (ESI⁺) m/z [M+H]⁺: 413.10
¹H NMR (CDCl₃, 600 MHz): δ=9.22 (s, 1H), 8.79 (s, 1H), 8.02 (s, 1H), 7.54 (m, 2H), 7.35 (m, 1H), 7.24-7.32 (m, 1H), 6.78 (m, 1H), 3.95 (br m, 1H), 3.71 (m, 2H), 3.71 (s, 3H), 3.07 (br m, 2H), 2.39 (s, 3H), 2.11-2.20 (m, 2H), 1.92 (m, 2H), 1.26 (m, 1H).

Example 36

(3R,5S)-1-[3-(Benzenesulfonyl)-8-quinolyl]piperidine-3,5-diol

The title compound was prepared using the procedure described in example 32 starting from 8-iodo-3-(phenylsulfonyl)quinoline (400 mg, 1.012 mmol) and (3S,4S)-pyrrolidine-3,4-diol (110 mg, 1.012 mmol) to give (3R,5S)-1-(3-(phenylsulfonyl)quinolin-8-yl)piperidine-3,5-diol (33.5 mg, yield 8.2%, purity 95%).
LCMS (ESI⁺) m/z [M+H]⁺: 385.10
¹H NMR (CDCl₃, 600 MHz): δ=9.12 (s, 1H), 8.81 (s, 1H), 8.04 (m, 2H), 7.5-7.65 (several m, 5H), 7.29 (m, 1H), 4.16 (m., 2H), 3.94 (m, 2H), 3.23 (m, 2H), 2.37 (m, 1H), 1.76 (m, 1H).

Example 37

1-[3-(Benzenesulfonyl)-8-quinolyl]piperidine-4-carboxylic Acid

The title compound was prepared using the procedure described in example 14 starting from piperidine-4-carboxylic acid (607 mg, 4.70 mmol) and 8-fluoro-3-(phenylsulfonyl)quinoline (300 mg, 1.044 mmol). The product was obtained by preparative HPLC chromatography on a reversed phase column to give 1-(3-(phenylsulfonyl)quinolin-8-yl)piperidine-4-carboxylic acid (84 mg, yield 20.3%).
LCMS (ESI⁺) m/z [M+H]⁺: 397.10
¹H NMR (DMSO-d₆, 600 MHz): δ=9.23 (br s, 1H), 9.04 (br s, 1H), 8.10 (m, 2H), 7.5-7.8 (several m, 5H), 7.31 (br m, 1H), 3.73 (br m, 2H), 2.84 (m, 2H), 2.31 (br m, 1H), 1.89-1.95 (m, 2H), 1.78-1.86 (m, 2H).

Example 38

1-[2-[(8-Fluoro-3-quinolyl)sulfonyl]phenyl]azetidin-3-ol

The title compound was prepared using the procedure described in example 35 starting from 8-fluoro-3-(2-fluorophenylsulfonyl)quinoline (300 mg, 0.983 mmol) and azetidin-3-ol (215 mg, 2.95 mmol) to give 1-(2-(8-fluoroquinolin-3-ylsulfonyl)phenyl)azetidin-3-ol (64 mg, yield 18.2%).
LCMS (ESI⁺) m/z [M+H]⁺: 359.05
¹H NMR (CDCl₃, 500 MHz): δ=9.26 (s, 1H), 8.73 (s, 1H), 7.99 (d, J=7.9 Hz, 1H), 7.76 (d, J=8.2 Hz, 1H), 7.61-7.66 (m, 1H), 7.55-7.60 (m, 1H), 7.48 (t, J=7.8 Hz, 1H), 6.98 (t, J=7.6 Hz, 1H), 6.72 (d, J=8.2 Hz, 1H), 4.61 (m, 1H), 4.28 (m, 2H), 3.82 (m, 2H), 2.11 (m, 1H).

Example 39

1-[3-(2-Methoxyphenyl)sulfonyl-8-quinolyl]azetidin-3-ol

The title compound was prepared using the procedure described in example 35 starting from 8-fluoro-3-(2-methoxyphenylsulfonyl)quinoline (200 mg, 0.630 mmol) and azetidin-3-ol (138 mg, 1.891 mmol to give 1-(3-(2-methoxyphenylsulfonyl)quinolin-8-yl)azetidin-3-ol (21 mg, yield 8.4%, purity 93%).
LCMS (ESI⁺) m/z [M+H]⁺: 371.10
¹H NMR (CDCl₃, 600 MHz): δ=9.08 (s, 1H), 8.68 (s, 1H), 8.21 (d, 1H), 7.52-7.60 (m, 1H), 7.45 (t, J=7.9 Hz, 1H), 7.20-7.28 (m, 1H), 7.14 (t, J=7.6 Hz, 1H), 6.89 (d, J=8.3 Hz, 1H), 6.67 (d, J=7.5 Hz, 1H), 4.81 (m, 1H), 4.66-4.72 (m, 2H), 4.06 (m, 2H), 3.76 (s, 3H), 3.76 (m, 1H).

Example 40

1-[3-(2-Methoxy-5-methyl-phenyl)sulfonyl-8-quinolyl]azetidin-3-ol

The title compound was prepared using the procedure described in example 35 (change temperature from 100° C.

to 80° C.) starting from 8-fluoro-3-(2-methoxy-5-methylphenylsulfonyl)quinoline (150 mg, 0.453 mmol) and azetidin-3-ol (99 mg, 1.358 mmol) to give 1-(3-(2-methoxy-5-methylphenylsulfonyl)quinolin-8-yl)azetidin-3-ol (11.2 mg, yield 6.4%).

LCMS (ESI$^+$) m/z [M+H]$^+$: 385.10

$^1$H NMR (CDCl$_3$, 600 MHz): δ=9.08 (s, 1H), 8.67 (s, 1H), 8.01 (s, 1H), 7.45 (t, J=7.9 Hz, 1H), 7.32-7.40 (m, 1H), 7.22-7.29 (m, 1H), 6.78 (d, J=8.3 Hz, 1H), 6.67 (d, J=7.7 Hz, 1H), 4.82 (m, 1H), 4.59-4.67 (m, 2H), 4.06 (m, 2H), 3.72 (s, 3H), 2.39 (s, 3H).

Example 41

(3S,4R)-1-[3-(Benzenesulfonyl)-8-quinolyl]piperidine-3,4-diol

The title compound was prepared using the procedure described in example 32 (change temperature from 100° C. to 80° C.) starting from 8-iodo-3-(phenylsulfonyl)quinoline (800 mg, 2.024 mmol) and (3S,4R)-piperidine-3,4-diol (261 mg, 2.227 mmol) to give trans-1-(3-(phenylsulfonyl)quinolin-8-yl)piperidine-3,4-diol (38 mg, yield 4.9%).

LCMS (ESI$^+$) m/z [M+H]$^+$: 385.10

$^1$H NMR (CDCl$_3$, 600 MHz): δ=9.19 (s, 1H), 8.80 (s, 1H), 8.03 (d, J=7.5 Hz, 2H), 7.59-7.64 (m, 1H), 7.52-7.59 (m, 4H), 7.26 (s, 1H), 4.03 (br. s., 1H), 3.95 (br s, 1H), 3.72 (br s, 1H), 3.44 (br s, 1H), 3.16 (br s, 1H), 3.02 (br s, 1H), 2.41 (br s, 1H), 2.03 (br s, 1H).

Example 42

(3R,4S)-1-[3-(Benzenesulfonyl)-8-quinolyl]pyrrolidine-3,4-diol

The title compound was prepared using the procedure described in example 26 starting from 8-iodo-3-(phenylsulfonyl)quinoline (400 ing, 1.012 mmol) and (3S,4S)-pyrrolidine-3,4-diol (110 mg, 1.012 mmol) to give (3S,4R)-1-(3-(phenylsulfonyl)quinolin-8-yl)pyrrolidine-3,4-diol (7 mg, yield 1.8%, purity 90%).

LCMS (ESI$^+$) m/z [M+H]$^+$: 371.10

$^1$H NMR (CDCl$_3$, 600 MHz): δ=9.05 (s, 1H), 8.66 (s, 1H), 8.02 (m, 2H), 7.45-7.65 (several m, 4H), 7.23-7.31 (m, 1H), 6.87 (m, 1H), 4.42 (br. m., 2H), 4.02 (m, 2H), 3.77 (m, 2H).

Example 43 cis-1-[3-(Benzenesulfonyl)-8-quinolyl]-3-fluoropiperidin-4-ol

Rac cis tert-butyl 3-fluoro-4-hydroxypiperidine-1-carboxylate (1.5 g, 6.84 mmol) was stirred with hydrogen chloride 4M in dioxane at room temperature overnight and subsequently concentrated to give (3R,4S)-3-fluoropiperidin-4-ol hydrochloride (1 g, yield 94%).

Rac cis-3-fluoropiperidin-4-ol hydrochloride (1.065 g, 6.84 mmol) was agitated with MP-carbonate (Macroporous triethylammonium methylpolystyrene carbonate resin from Biotage) (8.35 g, 27.4 mmol, 3.28 mmol/g) at room temperature overnight, filtered, washed and concentrated to give (3R,4S)-3-fluoropiperidin-4-ol (815 mg, yield 100%). 2,2-Bis(diphenylphosphino)-1,1-binapthyl (BINAP) (4.73 mg, 7.59 μmop, tris(dibenzylideneacetone)dipalladium(0) (3.48 mg, 3.8 μmol), cesium carbonate (272 mg, 835 μmol), (3R,4S)-3-fluoropiperidin-4-ol (63.3 mg, 531 μmol) and 8-iodo-3-(phenylsulfonyl)quinoline (150 mg, 380 μmol), were added and flushed with argon. To the reaction mixture was added degassed toluene (5 ml) and stirred at 100° C. for 9 h. The reaction mixture was diluted with ethyl acetate, filtered, washed and concentrated. The residue was purified using flash chromatography (12 g column; DCM 100%→DCM:MeOH 0:100). The product was obtained by preparative HPLC chromatography on a reversed phase column to give to give (3R,4S)-3-fluoro-1-(3-(phenylsulfonyl)quinolin-8-yl)piperidin-4-ol (12.9 mg, yield 7.9%, purity 90%).

LCMS (ESI$^+$) m/z [M+H]$^+$: 387.10

$^1$H NMR (CDCl$_3$, 600 MHz): δ=9.23 (s, 1H), 8.76-8.78 (s, 1H), 8.02 (m, 2H), 7.5-7.65 (several m, 5H), 7.35 (m, broad, 1H), 4.9-5.05 (br m, 1H), 4.19 (m, broad, 1H), 3.75 (br m, 1H), 3.58-3.66 (m, 1H), 3.45 (br m, 1H), 3.33-3.38 (m, 1H), 2.05-2.2 (m, broad, 2H).

Example 44

1-[3-[3-(Trifluoromethyl)phenyl]sulfonyl-8-quinolyl]azetidine-3-carboxylic Acid 2,2-Bis(diphenylphosphino)-1,1-binapthyl (BINAP) (5.38 mg, 8.64 μmop, tris(dibenzylideneacetone)dipalladium(0) (7.91 mg, 8.64 μmol), cesium carbonate (619 mg, 1.900 mmol) and 8-iodo-3-(3-(trifluoromethyl)phenylsulfonyl)quinoline (400 mg, 0.864 mmol) were added and flushed with argon for 6 h. Then tert-butyl azetidine-3-carboxylate (136 mg, 0.864 mmol) were dissolved in degassed toluene (5 ml) and added to the reaction mixture and stirred at 80° C. over the weekend. The reaction mixture was filtered, washed with DCM and concentrated. The residue was dissolved in DCM and washed several times with water. The organic layer was washed with brine, dried with sodium sulfate, filtered and concentrated. The residue was purified twice using flash chromatography (12 g column; DCM 100%→DCM:MeOH 0:100) to give tert-butyl 1-(3-(3-(trifluoromethyl)phenylsulfonyl)quinolin-8-yl)azetidine-3-carboxylate (53 mg, yield 11.8%, purity 95%).

To a solution of tert-butyl 1-(3-(3-(trifluoromethyl)phenylsulfonyl)quinolin-8-yl)azetidine-3-carboxylate (40 mg, 0.081 mmol) in DCM (2 ml) was added TFA (370 mg, 3.25 mmol) at 0° C. and stirred at room temperature for 2 h. The reaction mixture was concentrated and washed several times with DCM and finally concentrated under high-vacuum. The residue was dissolved in DCM and washed with brine. The organic layer was dried with sodium sulfate, filtered and concentrated. The residue was stirred 3 times with n-pentane and decanted. The residue was concentrated under high-vacuum to give 1-(3-(3-(trifluoromethyl)phenylsulfonyl)quinolin-8-yl)azetidine-3-carboxylic acid (7.1 mg, yield 18.6%, purity 93%).

LCMS (ESI$^+$) m/z [M+H]$^+$: 437.00

$^1$H NMR (CDCl$_3$, 600 MHz): δ=9.05 (s, 1H), 8.70 (s, 1H), 8.28 (s, 1H), 8.20 (m, 1H), 7.85 (m, 1H), 7.69 (m, 1H), 7.51 (m, 1H), 7.3 (m, 1H), 6.69 (m, 1H), 4.54-4.59 (m, 2H), 4.47 (m, 2H), 3.63-3.69 (m, 1H).

Example 45

(3R,4R)-1-[3-(Benzenesulfonyl)-8-quinolyl]pyrrolidine-3,4-diol

The title compound was prepared using the procedure described in example 32 (change temperature from 100° C. to 80° C.) starting from 8-iodo-3-(phenylsulfonyl)quinoline (400 mg, 1.012 mmol) and (3R,4R)-pyrrolidine-3,4-diol (104 mg, 1.012 mmol) to give (3R,4R)-1-(3-(phenylsulfonyl)quinolin-8-yl)pyrrolidine-3,4-diol (20.8 mg, yield 5.6%).

LCMS (ESI+) m/z [M+H]+: 371.10

$^1$H NMR (CDCl$_3$, 600 MHz): δ=9.08 (s, 1H), 8.70 (br s, 1H), 8.02 (m, 2H), 7.5-7.6 (several m, 4H), 7.33-7.37 (m, 1H), 6.97 (m, very broad, 1H), 4.36 (br m, 2H), 4.23 (m, 2H), 3.71 (m, 2H).

Example 46

1-[3-(3-Trifluoromethyl-benzenesulfonyl)-quinolin-8-yl]-piperidine-3-carboxylic Acid Amide Example 47

1-[3-(3-Cyanophenyl)sulfonyl-8-quinolyl]piperidine-4-carboxylic Acid 47.1 Preparation of Ethyl 1-[3-(3-cyanophenyl)sulfonyl-8-quinolyl]piperidine-4-carboxylate To a solution of PdCl$_2$(dppf) (5.81 mg, 7.95 µmol), zinc (0.519 mg, 7.95 µmol), ethyl 1-[3-(3-bromophenyl)sulfonyl-8-quinolyl]piperidine-4-carboxylate (20 mg, 0.040 mmol) and dicyanozinc (2.80 mg, 0.024 mmol) in 1-methylpyrrolidin-2-one (5 mL) was heated to 140° C. with stirring for 16 h. TLC showed the starting compound had been consumed. Then water (5 mL) was added, and the mixture was extracted with dichloromethane 3 times (3×5 mL). The combined organic phases were washed with brine (3 mL), dried over Na$_2$SO$_4$ (1 g), then concentrated to give a residue, which was purified by Prep-TLC to give the title compound (10 mg, yield 47.9%) as a yellow solid.

47.2 Preparation of 1-[3-(3-cyanophenyl)sulfonyl-8-quinolyl]piperidine-4-carboxylic Acid To a solution of ethyl 1-[3-(3-cyanophenyl)sulfonyl-8-quinolyl]piperidine-4-carboxylate (10 mg, 0.022 mmol) from step 47.2 in tetrahydrofuran (1 mL) was added an aqueous solution of LiOH (1 mL, 1.0 mol/L), and the mixture was stirred at 25° C. for 3 h. LCMS showed that the starting compound had been consumed. The reaction was adjusted to pH=6-7 with HCl (1M), then extracted with ethyl acetate 3 times (3×10 mL). The combined organic phases were washed with brine (10 mL), dried over Na$_2$SO$_4$ (1 g), then concentrated to give a residue, which was purified by Prep-TLC to give the title compound (4 mg, yield 40.6%) as yellow solid.

$^1$H NMR (methanol-d$_4$ 400 MHz): δ=9.26 (s, 1H), 9.01 (s, 1H), 8.53 (s, 1H), 8.38 (br d, J=8.2 Hz, 1H), 8.03 (d, J=8.2 Hz, 1H), 7.80 (t, J=8.0 Hz, 1H), 7.74-7.70 (m, 1H), 7.65 (t, J=8.0 Hz, 1H), 7.45 (d, J=7.1 Hz, 1H), 3.77 (br d, J=13.0 Hz, 2H), 2.88 (br s, 2H), 2.49 (br s, 1H), 2.07 (br s, 4H)

LCMS (ESI+): m/z 422.1 (M+H)+

Example 48

1-[3-(3-Carbamoylphenyl)sulfonyl-8-quinolyl]piperidine-4-carboxylic Acid

To a solution of ethyl 1-[3-(3-cyanophenyl)sulfonyl-8-quinolyl]piperidine-4-carboxylate (20 mg, 0.044 mmol) from step 47.1 of example 47 in tetrahydrofuran (2 mL) was added an aqueous solution of NaOH (1 mL, 4.00 mmol), and the mixture was stirred at 25° C. for 3 h. LCMS showed that the starting compound had been consumed. The mixture was purified with Prep-HPLC to give the title compound (3.5 mg, yield 17.61%) as yellow solid.

$^1$H NMR (methanol-d$_4$ 400 MHz): δ=12.20 (br s, 1H), 9.28 (d, J=2.2 Hz, 1H), 9.07 (d, J=2.2 Hz, 1H), 8.52 (s, 1H), 8.30 (s, 1H), 8.25 (br d, J=8.4 Hz, 1H), 8.17 (d, J=7.9 Hz, 1H), 7.78-7.74 (m, 2H), 7.68-7.61 (m, 2H), 7.34 (d, J=7.5 Hz, 1H), 3.76 (br d, J=11.9 Hz, 2H), 2.85 (br t, J=10.7 Hz, 2H), 2.44 (br s, 1H), 1.98-1.93 (m, 2H), 1.87-1.72 (m, 3H).

LCMS (ESI+): ink 440.0 (M+H)+

Example 49

1-[3-(3-Carboxyphenyl)sulfonyl-8-quinolyl]piperidine-4-carboxylic Acid

To a solution of ethyl 1-[3-(3-cyanophenyl)sulfonyl-8-quinolyl]piperidine-4-carboxylate (30 mg, 0.067 mmol) from step 47.1 of example 47 in tetrahydrofuran (1 mL) was added an aqueous solution of LiOH (1 mL, 1.0 mol/L), and the mixture was stirred at 25° C. for 3 h. LCMS showed that the starting compound had been consumed. The reaction was purified with Prep-HPLC to give the title compound (6 mg, yield 20.4%) as yellow solid.

$^1$H NMR: (methanol-d$_4$ 400 MHz): δ=9.44 (d, J=2.4 Hz, 1H), 9.22 (d, J=2.2 Hz, 1H), 8.67 (t, J=1.7 Hz, 1H), 8.33 (ddd, J=1.8, 8.0, 9.9 Hz, 2H), 8.21 (d, J=7.7 Hz, 1H), 8.08 (d, J=6.8 Hz, 1H), 7.89-7.84 (m, 1H), 7.77 (t, J=7.8 Hz, 1H), 3.90 (br d, J=12.3 Hz, 2H), 3.61 (br s, 2H), 2.79 (td, J=5.1, 10.1 Hz, 1H), 2.33-2.25 (m, 4H)

LCMS (ESI+): m/z 441.0 (M+H)+

Example 50

1-[3-(m-Tolylsulfonyl)-8-quinolyl]piperidine-4-carboxylic Acid 50.1 Preparation of Ethyl 1-[3-(m-tolylsulfonyl)-8-quinolyl]piperidine-4-carboxylate To a solution of ethyl 1-(3-((3-bromophenyl)sulfonyl)quinolin-8-yl)piperidine-4-carboxylate (100 mg, 0.199 mmol) in 1,4-dioxane (2 mL) and water (0.2 mL) was added methylboronic acid (17.84 mg, 0.298 mmol), XPhos Pd G2 catalyst (3.13 mg, 3.97 µmol) and Cs$_2$CO$_3$ (194 mg, 0.596 mmol). The mixture was heated at 90° C. with stirring for 16 h under N$_2$. TLC showed the reaction was completed. The reaction was filtered and concentrated to give crude product, which was purified by Prep-HPLC (TFA) to give the title compound (100 mg, yield 95%) as yellow powder.

50.2 Preparation of 1-[3-(m-tolylsulfonyl)-8-quinolyl]piperidine-4-carboxylic Acid To a solution of ethyl 1-[3-(m-tolylsulfonyl)-8-quinolyl]piperidine-4-carboxylate (70 mg, 0.160 mmol) from step 50.1 in 1,4-dioxane (2 mL) and water (2 mL) was added NaOH (12.77 mg, 0.319 mmol). The mixture was stirred for 2 h at 70° C. LCMS showed the reaction was completed. The reaction mixture was adjusted to pH 4-5 with HCl (1M), then extracted with dichlormethane (3×4 mL), and the combined organic layers were concentrated to dryness to give crude product. The crude product was purified by Prep-HPLC (TFA) to give the title compound (7 mg, yield 10.68%) as yellow powder. $^1$H NMR (DMSO-d, 400 MHz): δ=9.24 (d, J=2.4 Hz, 1H), 9.04 (d, J=2.2 Hz, 1H), 7.92 (s, 1H), 7.90-7.86 (m, 1H), 7.79 (d, J=7.9 Hz, 1H), 7.64 (t, J=7.9 Hz, 1H), 7.55-7.51 (m, 2H), 7.38 (d, J=7.5 Hz, 1H), 3.76 (br d, J=11.9 Hz, 2H), 2.90 (br t, J=10.7 Hz, 2H), 2.54 (t, J=5.5 Hz, 1H), 2.39 (s, 3H), 2.00-1.94 (m, 2H), 1.90-1.78 (m, 2H)

LCMS (ESI+): m/z 411.0 (M+H)$^+$

Example 51

1-[3-[3-(Trifluoromethoxy)phenyl]sulfonyl-8-quinolyl]piperidine-4-carboxylic Acid 51.1 Preparation of Tert-Butyl 1-[3-[3-(trifluoromethoxy)phenyl]sulfonyl-8-quinolyl]piperidine-4-carboxylate To a solution of 8-iodo-3-[3-(trifluoromethoxy)phenyl]sulfonyl-quinoline (70.0 mg, 0.146 mmol) in toluene (5 mL) was added tert-butyl piperidine-4-carboxylate (27.1 mg, 0.146 mmol), (S)—N,N-dimethyl-1-[(R)-2-(diphenylphosphino)ferrocenyl]ethylamine (12.9 mg, 0.029 mmol), sodium 2-methylpropan-2-olate (21.1 mg, 0.219 mmol) and tris(dibenzylideneacetone)dipalladium(0) (13.4 mg, 0.015 mmol). The mixture was stirred for 12 h at 90° C. under $N_2$. TLC (petroleum ether/ethyl acetate=3:1, Rf=0.4) showed the reaction worked well. The solution was concentrated to afford the crude product, which was purified by Prep-TLC to give the title compound (50 mg, yield 63.8%) as a yellow solid.

51.2 Preparation of 1-[3-[3-(trifluoromethoxy)phenyl]sulfonyl-8-quinolyl]piperidine-4-carboxylic Acid To a solution of tert-butyl 1-[3-[3-(trifluoromethoxy)phenyl]sulfonyl-8-quinolyl]-piperidine-4-carboxylate (40 mg, 0.172 mmol) from step 51.1 in $CH_2Cl_2$ (10 mL) was added 2,2,2-trifluoroacetic acid (2 mL). The mixture was stirred for 2 h at 25° C. TLC (dichloromethane:methanol=20:1, Rf=0.3) showed the reaction was completed. The mixture was filtered and concentrated in vacuum. The residue was purified by Prep-HPLC to afford the title compound (23 mg, yield 64.2%) as a light yellow solid.

$^1$H NMR (methanol-$d_4$, 400 MHz): δ=9.32 (d, J=2.2 Hz, 1H), 9.08 (d, J=2.2 Hz, 1H), 8.13 (d, J=7.5 Hz, 1H), 8.04 (s, 1H), 7.89 (br d, J=8.6 Hz, 1H), 7.75 (td, J=8.0, 12.3 Hz, 2H), 7.69-7.61 (m, 2H), 3.82 (br d, J=11.7 Hz, 2H), 3.12 (br s, 2H), 2.63-2.59 (m, 1H), 2.18-2.13 (m, 4H)

LCMS (ESI+): m/z 481.2 (M+H)$^+$

Example 52

1-[3-(3-Fluorophenyl)sulfonyl-8-quinolyl]piperidine-4-carboxylic Acid 52.1 Preparation of 3-(3-fluorophenyl)sulfonyl-8-iodo-quinoline A solution of 3-(3-fluorophenyl)sulfonylquinolin-8-amine (530 mg, 1.753 mmol) in trifluoroacetic acid (2 mL) was stirred at 25° C. for 20 min. Then the mixture was concentrated under reduced pressure to afford a residue, which was dissolved in acetonitrile (20 mL). tert-Butyl nitrite (271 mg, 2.63 mmol) was added at 0° C., and after stirring for 15 min, copper(I) iodide (668 mg, 3.51 mmol) was added to the mixture at 0° C. Then the mixture was stirred at 25° C. for 1 h. TLC (petroleum ether:ethyl acetate=2:1, Rf=0.5) showed that the starting compound (530 mg, 1.753 mmol) had been consumed and product had formed. The mixture was diluted with water (100 mL) and extracted with $CH_2Cl_2$ (3×200 mL). The organic extracts were dried over $Na_2SO_4$, filtered, and concentrated under reduced pressure to give the crude product, which was purified by column chromatography on silica gel (petroleum ether:ethyl acetate=80:1~3:1) to give the title compound (500 mg, yield 69.0%) as a yellow solid.

52.2 Preparation of Ethyl 1-[3-(3-fluorophenyl)sulfonyl-8-quinolyl]piperidine-4-carboxylate To a mixture of 3-(3-fluorophenyl)sulfonyl-8-iodo-quinoline (300 mg, 0.726 mmol) from step 52.1 in toluene (10 mL) and was added sodium tert-butoxide (140 mg, 1.452 mmol), $Pd_2(dba)_3$ (tris(dibenzylideneacetone)dipalladium (0)) (66.5 mg, 0.073 mmol), ethyl piperidine-4-carboxylate (342 mg, 2.178 mmol) at 25° C. Nitrogen was bubbled through the mixture for 30 min. Then the mixture was heated at 110° C. for 12 h. LCMS showed the reaction worked well. The mixture was concentrated under reduced pressure and the residue was purified by column chromatography on silica gel eluted with petroleum ether:ethyl acetate=100:1 to 3:1 to give the title compound (100 mg, yield 31.1%) as a yellow solid.

LCMS (ESI+): m/z 443 (M+H)$^+$, Rt: 1.263 min.

52.3 Preparation of 1-[3-(3-fluorophenyl)sulfonyl-8-quinolyl]piperidine-4-carboxylic Acid To a mixture of ethyl 1-[3-(3-fluorophenyl)sulfonyl-8-quinolyl]piperidine-4-carboxylate (0.030 g, 0.068 mmol) from step 52.2 in 1, 4-dioxane (6.25 mL) and $H_2O$ (6.25 mL) was added NaOH (1.0 g, 25.00 mmol) at 25° C. The solution was stirred at 68° C. for 1 h. LCMS showed the reaction worked well. The organic phase was purified by Prep-HPLC to give the title compound (10 mg, yield 35.6%) as a yellow solid.

$^1$H NMR (CDCl$_3$, 400 MHz): δ=9.25 (d, J=2.4 Hz, 1H), 8.79 (d, J=2.4 Hz, 1H), 8.07-8.01 (m, 2H), 7.76-7.72 (m, 1H), 7.71-7.60 (m, 2H), 7.23-7.18 (m, 2H), 3.92 (br d, J=11.9 Hz, 2H), 3.37 (br s, 2H), 2.76-2.66 (m, 1H), 2.32-2.19 (m, 4H)

LCMS (ESI+): m/z 415 (M+H)$^+$

Example 53

1-[3-(3-Pyrrolidin-1-ylphenyl)sulfonyl-8-quinolyl]piperidine-4-carboxylic Acid 53.1 Preparation of Ethyl 1-[3-(3-pyrrolidin-1-ylphenyl)sulfonyl-8-quinolyl]piperidine-4-carboxylate To a solution of ethyl 1-[3-(3-bromophenyl)sulfonyl-8-quinolyl]piperidine-4-carboxylate (100 mg, 0.199 mmol) in toluene (2 mL) was added pyrrolidine (141 mg, 1.986 mmol), sodium 2-methylpropan-2-olate (38.2 mg, 0.397 mmol), BINAP (12.37 mg, 0.020 mmol) and $Pd_2(dba)_3$ (18.19 mg, 0.020 mmol) into the reaction mixture under $N_2$ atmosphere. The reaction was stirred for 16 h at 110° C. TLC showed that the starting compound had been consumed. Then water (5 mL) was added, and the mixture was extracted with dichloromethane 3 times (3×5 mL). The combined organic phases were washed with brine (3 mL), dried over $Na_2SO_4$ (1 g), and concentrated to give a residue which was purified by Prep-TLC to give the title compound (20 mg, yield 20.4%) as a yellow solid.

53.2 Preparation of 1-[3-(3-pyrrolidin-1-ylphenyl)sulfonyl-8-quinolyl]piperidine-4-carboxylic Acid To a solution of ethyl 1-[3-(3-pyrrolidin-1-ylphenyl)sulfonyl-8-quinolyl]piperidine-4-carboxylate (15 mg, 0.030 mmol) from step 53.1 in dioxane (1 mL) was added an aqueous solution of NaOH (1 mL, 4 M), and the mixture was stirred at 65° C. for 1 h. LCMS showed that the starting compound had been consumed. The reaction was purified by Prep-HPLC to give the title compound (9 mg, yield 62.3%) as yellow solid. $^1$H NMR (CDCl$_3$, 400 MHz): δ=9.29 (s, 1H), 8.81 (s, 1H), 7.75 (br d, J=7.9 Hz, 1H), 7.66-7.61 (m, 1H), 7.35-7.30 (m, 2H), 7.24-7.20 (m, 1H), 7.12 (s, 1H), 6.70 (br d, J=8.4 Hz, 1H), 3.95 (br s, 3H), 3.32 (br s, 5H), 2.29 (br s, 5H), 2.04 (br s, 5H)

LCMS (ESI+): m/z 466.0 (M+H)$^+$

Example 54

1-[3-[3-(3-Methoxypyrrolidin-1-yl)phenyl]sulfonyl-8-quinolyl]piperidine-4-carboxylic Acid

54.1 Preparation of Ethyl 1-[3-[3-(3-benzyloxypyrrolidin-1-yl)phenyl]sulfonyl-8-quinolyl]piperidine-4-carboxylate To a solution of ethyl 1-[3-(3-bromophenyl)sulfonyl-8-quinolyl]piperidine-4-carboxylate (100 mg, 0.199 mmol) in toluene (2 mL) was added 3-(benzyloxy)-pyrrolidine (70.4 mg, 0.397 mmol), sodium 2-methylpropan-2-olate (38.2 mg, 0.397 mmol), BINAP (12.37 mg, 0.020 mmol) and Pd$_2$(dba)$_3$ (18.19 mg, 0.020 mmol) under N$_2$ atmosphere. The reaction was stirred for 16 h at 110° C. TLC showed that the starting compound had been consumed. Then water (5 mL) was added, and the mixture was extracted with dichloromethane 3 times (3×5 mL). The combined organic phases were washed with brine (3 mL), dried over Na$_2$SO$_4$ (1 g), and concentrated to give a residue which was purified by Prep-TLC to give the title compound (50 mg, yield 42.0%) as a yellow solid.

54.2 Preparation of 1-[3-[3-(3-hydroxypyrrolidin-1-yl)phenyl]sulfonyl-8-quinolyl]piperidine-4-carboxylic Acid To a solution of ethyl 1-[3-[3-(3-benzyloxypyrrolidin-1-yl)phenyl]sulfonyl-8-quinolyl]piperidine-4-carboxylate (35 mg, 0.058 mmol) from step 54.1 was added con. HCl (5 mL). The reaction was stirred at 25° C. for 16 h. LCMS showed that the starting compound had been consumed. The reaction was purified with Prep-HPLC to give the title compound (27 mg, yield 50.8%) as a yellow solid.

$^1$H NMR (methanol-d$_4$, 400 MHz): δ=9.33 (s, 1H), 9.06 (s, 1H), 8.05 (br d, J=8.2 Hz, 1H), 7.89 (br d, J=7.7 Hz, 1H), 7.81-7.76 (m, 1H), 7.41-7.36 (m, 1H), 7.26 (d, J=7.3 Hz, 1H), 7.14 (s, 1H), 6.82 (br d, J=7.1 Hz, 1H), 3.84 (br d, J=11.9 Hz, 3H), 3.54-3.35 (m, 7H), 3.23 (br d, J=9.9 Hz, 2H), 2.75-2.67 (m, 1H), 2.28-2.12 (m, 7H), 2.06 (br s, 1H)

54.3 Preparation of Methyl 1-[3-[3-(3-methoxypyrrolidin-1-yl)phenyl]sulfonyl-8-quinolyl]piperidine-4-carboxylate To a stirred solution of 1-[3-[3-(3-hydroxypyrrolidin-1-yl)phenyl]sulfonyl-8-quinolyl]piperidine-4-carboxylic acid (10.00 mg, 0.021 mmol) from step 54.2 in dimethyl formamide (2 mL) was added sodium hydride (0.997 mg, 0.042 mmol) at 0° C. The mixture was stirred for 15 min, then iodomethane (8.84 mg, 0.062 mmol) was slowly added and the reaction was stirred for 10 h at 25° C. TLC showed the reaction was completed. The reaction was diluted with water (2 mL) and extracted with dichloromethane (3×3 mL). The combined organic phases were washed with water (6 mL), brine (3 mL), dried over Na$_2$SO$_4$ (1 g) and concentrated in vacuum to give crude product of the title compound (10 mg, yield 94%), which was used in the next step without any further purification.

54.4 Preparation of 1-[3-[3-(3-methoxypyrrolidin-1-yl)phenyl]sulfonyl-8-quinolyl]-piperidine-4-carboxylic Acid To a stirred solution of methyl 1-[3-[3-(3-methoxypyrrolidin-1-yl)phenyl]sulfonyl-8-quinolyl]piperidine-4-carboxylate (10.00 mg, 0.020 mmol) from step 54.3 in tetrahydrofuran (0.5 mL) and water (0.5 mL) was added lithium hydroxide (0.470 mg, 0.020 mmol). The mixture was stirred for 8 h at 25° C. The reaction was adjusted to pH 4~5 with HCl (1M) and extracted with dichloromethane (3×2 mL). The combined organic phases were washed with water (5 mL), brine (5 mL), dried over Na$_2$SO$_4$ (0.5 g) and concentrated in vacuum. The crude product was purified by Prep-HPLC (TFA) to give the title compound (5.7 mg, yield 58.6%) as a yellow oil.

$^1$H NMR (methanol-d$_4$, 400 MHz): δ=9.35 (d, J=2.2 Hz, 1H), 9.07 (d, J=2.2 Hz, 1H), 8.05 (d, J=8.3 Hz, 1H), 7.89-7.84 (m, 1H), 7.83-7.76 (m, 1H), 7.44-7.38 (m, 1H), 7.29 (d, J=7.9 Hz, 1H), 7.17 (s, 1H), 6.85 (br d, J=7.9 Hz, 1H), 4.17 (br s, 1H), 3.87 (br d, J=12.3 Hz, 2H), 3.53 (dd, J=4.8, 10.5 Hz, 1H), 3.43-3.39 (m, 3H), 3.38 (s, 3H), 2.75-2.69 (m, 1H), 2.31-2.09 (m, 7H)

LCMS (ESI+): m/z 496.1 (M+H)$^+$

Example 55

1-[3-(3-Piperazin-1-ylphenyl)sulfonyl-8-quinolyl]piperidine-4-carboxylic Acid

55.1 Preparation of Ethyl 1-[3-(3-piperazin-1-ylphenyl)sulfonyl-8-quinolyl]-piperidine-4-carboxylate To a solution of ethyl 1-[3-(3-bromophenyl)sulfonyl-8-quinolyl]piperidine-4-carboxylate (100 mg, 0.199 mmol) in toluene (4 mL) was added piperazine (86 mg, 0.993 mmol), sodium 2-methylpropan-2-olate (38.2 mg, 0.397 mmol), BINAP (12.37 mg, 0.020 mmol) and Pd$_2$(dba)$_3$ (18.19 mg, 0.020 mmol) under N$_2$ atmosphere. The mixture was stirred at 110° C. for 16 h. LCMS showed that the starting compound had been consumed. The mixture was filtered, then concentrated and purified with Prep-HPLC to give the title compound (50 mg, yield 43.5%) as a yellow solid.

55.2 Preparation of 1-[3-(3-piperazin-1-ylphenyl)sulfonyl-8-quinolyl]piperidine-4-carboxylic Acid To a solution of ethyl 1-[3-(3-piperazin-1-ylphenyl)sulfonyl-8-quinolyl]piperidine-4-carboxylate (30 mg, 0.059 mmol) from step 55.1 in dioxane (1 mL) was added aqueous NaOH (1 mL, 4 M), and the reaction was stirred at 65° C. for 1 h. LCMS showed that the starting compound was consumed. The reaction was purified with Prep-HPLC to give the title compound (12 mg, yield 41.9%) as a yellow solid.

$^1$H NMR (D$_2$O, 400 MHz): δ=9.38 (s, 1H), 9.19 (d, J=2.2 Hz, 1H), 8.25 (dd, J=8.1, 14.7 Hz, 2H), 7.92 (t, J=8.1 Hz, 1H), 7.73 (s, 1H), 7.69-7.66 (m, 1H), 7.64-7.59 (m, 1H), 7.42 (br d, J=7.9 Hz, 1H), 3.92 (br d, J=12.3 Hz, 2H), 3.82-3.72 (m, 2H), 3.60-3.56 (m, 4H), 3.47-3.43 (m, 4H), 2.83 (br t, J=10.3 Hz, 1H), 2.42-2.24 (m, 4H)

LCMS (ESI+): m/z 481.1 (M+H)$^+$

Example 56

1-[3-[3-(4-Methylpiperazin-1-yl)phenyl]sulfonyl-8-quinolyl]piperidine-4-carboxylic Acid To a solution of ethyl 1-[3-(3-bromophenyl)sulfonyl-8-quinolyl]piperidine-4-carboxylate (100 mg, 0.199 mmol) in toluene (2 mL) was added 1-methylpiperazine (99 mg, 0.993 mmol), sodium 2-methylpropan-2-olate (38.2 mg, 0.397 mmol), BINAP (12.37 mg, 0.020 mmol) and Pd$_2$(dba)$_3$ (18.19 mg, 0.020 mmol) under N$_2$ atmosphere. The reaction was stirred at 110° C. for 16 h. LCMS showed that the starting compound was consumed. The reaction was filtered, then concentrated and purified by Prep-HPLC to give the title compound (6 mg, yield 6.1%) as a yellow solid.

$^1$H NMR (D$_2$O, 400 MHz): δ=9.34 (d, J=2.3 Hz, 1H), 9.14 (d, J=2.3 Hz, 1H), 8.25 (t, J=7.3 Hz, 2H), 7.89 (t, J=8.1 Hz, 1H), 7.65 (d, J=2.1 Hz, 1H), 7.62-7.52 (m, 2H), 7.35 (dd, J=1.8, 8.2 Hz, 1H), 3.95-3.80 (m, 6H), 3.62 (br d, J=11.4 Hz, 2H), 3.28-3.13 (m, 4H), 2.98-2.88 (m, 4H), 2.45-2.25 (m, 4H)

LCMS (ESI+): m/z 495.1 (M+H)$^+$

Example 57

2-[1-[3-[3-(Trifluoromethyl)phenyl]sulfonyl-8-quinolyl]-4-piperidyl]acetic Acid 57.1 Preparation of Methyl 2-[1-[3-[3-(trifluoromethyl)phenyl]sulfonyl-8-quinolyl]-4-piperidyl]acetate To a solution of 8-iodo-3-[3-(trifluoromethyl)phenyl]sulfonyl-quinoline (250 mg, 0.540 mmol) in dimethyl formamide (3 mL) was added methyl 2-(piperidin-4-yl)acetate (255 mg, 1.619 mmol), sodium tert-butoxide (207 mg, 2.159 mmol), Pd$_2$(dba)$_3$ (49.4 mg, 0.054 mmol). Nitrogen was bubbled through the mixture for 30 min. Then the reaction was heated at 120° C. for 12 h. LCMS showed the reaction worked well. The mixture was concentrated under reduced pressure and the residue was purified by Prep-TLC to give the title compound (120 mg, yield 45.1%) as a yellow solid.

LCMS (ESI+): m/z 493.1 (M+H)$^+$, Rt: 2.246 min.

57.2 Preparation of 2-[1-[3-[3-(trifluoromethyl)phenyl]sulfonyl-8-quinolyl]-4-piperidyl]acetic Acid To a solution of methyl 2-[1-[3-[3-(trifluoromethyl)phenyl]sulfonyl-8-quinolyl]-4-piperidyl]acetate (100 mg, 0.203 mmol) from step 57.1 in 1, 4-dioxane (2 mL) and H$_2$O (2 mL) was added NaOH (300 mg, 7.500 mmol). Then the mixture was heated at 65° C. for 1 h. LCMS showed that the starting compound was consumed and the desired product generated. The reaction mixture was purified by Prep-HPLC to give the title compound (37 mg, yield 38.1%).

$^1$H NMR (methanol-d$_4$, 400 MHz): δ=9.46 (d, J=2.2 Hz, 1H), 9.26 (d, J=2.2 Hz, 1H), 8.43-8.39 (m, 2H), 8.22 (d, J=7.9 Hz, 1H), 8.13 (d, J=7.9 Hz, 1H), 8.04 (d, J=8.3 Hz, 1H), 7.91-7.83 (m, 2H), 3.87 (br d, J=11.8 Hz, 2H), 3.63 (br t, J=11.6 Hz, 2H), 2.43 (d, J=7.0 Hz, 2H), 2.26-2.12 (m, 3H), 1.97-1.84 (m, 2H)

LCMS (ESI+): m/z 478.5 (M+H)$^+$

Example 58

2-[1-[3-[3-(Trifluoromethyl)phenyl]sulfonyl-8-quinolyl]-3-piperidyl]acetic Acid

The title compound was prepared in analogy to example 57 starting from methyl 2-(piperidin-3-yl)acetate.

LCMS (ESI+): m/z 478.5 (M+H)$^+$

II. Biological Investigations

Displacement of radioligands binding to the following cloned human receptors

1. Preparation of Membranes by Ultrasonic Treatment and Differential Centrifugation Cells from stable clonal cell lines expressing the corresponding receptor (5-HT$_6$, α$_1$-adrenergic, dopamine D$_2$ or histamine H$_1$ receptors) were washed with PBS (w/o Ca$^{++}$, Mg$^{++}$) and harvested in PBS with 0.02% EDTA. The cells were collected by centrifugation at 500 g for 10 min. at 4° C., washed with PBS and centrifuged (500 g, 10 min. 4° C.). The pellets were stored at −80° C. until use. For membrane preparation, the thawed cell pellet was resuspended in ice-cold sucrose buffer (0.25 M sucrose, 10 mM Hepes (pH 7.4), 1 mM Phenylmethylsulfonyl fluoride (PMSF) in DMSO, 5 µg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1.000 g for 10 min. at 4° C. The sucrose buffer supernatant was then centrifuged at 60.000 g for 1 h at 4° C. (Beckman Ultrazentrifuge XL 80). The pellet was resuspended in 30 ml ice-cold Tris buffer (20 mM TRIS (pH 7.4), 5 µg/ml Pepstatin A, 0.1 mM PMSF, 3 mM EDTA) by pipetting through a 10 ml serological pipet and centrifuged for 1 h at 4° C. at 60.000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

2. Receptor Binding Experiments

All receptor binding experiments were carried out in the corresponding assay buffer in a total volume of 200 µl in the presence of various concentrations of test compound (10$^{-5}$ M to 10$^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96 well-plate harvester. After the plates had been dried for 2 h at 55° C. in a drying chamber scintillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980).

a) 5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a $K_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 μM pargyline, pH 7.4) to a concentration of 8 μg protein/assay and homogenized by gentle vortexing For inhibition studies, 1 nM [$^3$H]-Lysergic Acid Diethylamide was incubated in the presence of various concentrations of test compound in assay buffer. Non-specific binding was defined with 1 μM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

b) Dopamine D$_2$ Receptor Binding Assay

HEK293 cells stably expressing the dopamine D$_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a $K_D$ of 0.22 nM for [$^{125}$I]-iodospiperone (PerkinElmer Life Sciences, NEX284) was determined by means of saturation binding experiments. On the day of the assay, the membranes were thawed, diluted in assay buffer (50 mM Tris-HCl, 120 mM NaCl, 5 mM MgCl$_2$, 5 mM KCl, 1.5 mM CaCl$_2$, pH 7.4) to a concentration of 15 μg protein/assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 μM haloperidol. The binding reaction was carried out for 1 h at room temperature and terminated by filtration on Packard Unifilter GF/B (0.1% PEI) plates, followed by 6 wash cycles with an ice-cold 7% polyethylenglycol solution.

c) α$_1$-Adrenergic Receptor Binding Assay

CHO-K$_1$ cells stably expressing the α$_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a $K_D$ of 0.12 nM for [$^3$H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 μg protein/assay and homogenized by gentle vortexing. For inhibition studies, 0.1 nM [$^3$H]-prazosine (PerkinElmer Life Sciences, NET823) was incubated in the presence of various concentrations of test compound in assay buffer. Non-specific binding was defined with 1 μM phentolamine. The binding reaction was carried out for 1 h at room temperature and terminated by filtration on Packard Unifilter GF/C (0.1% PEI) plates, followed by 3 wash cycles with ice-cold assay buffer.

d) H$_1$ Receptor Binding Assay

CHO-K$_1$ cells stably expressing the histamine H$_1$ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a $K_D$ of 0.83 nM for [$^3$H]-pyrilamine (PerkinElmer Life Sciences, NET594) was determined by means of saturation binding experiments. On the day of the assay, the membranes were thawed, diluted in assay buffer (50 mM Na$_2$HPO$_4$, 50 mM KH$_2$PO$_4$, pH 7.4) to a concentration of 6 μg protein/assay and homogenized by gentle vortexing. For inhibition studies, 1 nM [$^3$H]-pyrilamine (PerkinElmer Life Sciences, NET594) was incubated in the presence of various concentrations of test compound in assay buffer. Non-specific binding was defined with 1 μM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). IC$_{50}$, nH and K$_i$ values were expressed as geometrical mean. For receptors with a low affinity for the test compound, where the highest tested compound concentration inhibited less than 30% of specific radioligand binding, K$_i$-values were determined according to the equation of Cheng and Prusoff (Biochem. Pharmacol. 1973, 22, 2099-2108) and expressed as greater than (>).

The results of the receptor binding studies are expressed as receptor binding constants K$_i$(5-HT$_6$), K$_i$(D$_2$), K$_i$(α$_1$-adrenergic) and K$_i$(H$_1$), respectively, as described herein before, and given in table 1.

4. Metabolic Stability

Samples of the tested compounds (0.5 μM) were preincubated together with human liver microsomes (0.25 mg of microsomal protein/mL) in 0.05 M potassium phosphate buffer of pH 7.4 in microtiter plates at 37° C. for 5 minutes. The reaction was started by adding NADPH (1.0 mM). After 0, 5, 10, 15, 20 and 30 minutes, an aliquot was removed, the reaction was cooled and stopped by adding twice the amount of quench solution consisting of acetonitrile/methanol 1:1, and containing 0.2 μM carbutamide as internal standard. The samples were frozen until analyzed. The remaining concentration of undegraded test substance was determined by liquid chromatography-tandem mass spectrometry (LC-MS/MS). The half-life ($t_{1/2}$) was determined from the gradient of the ratio of the signal of (test substance/internal standard)/unit time plot, allowing the calculation of the half-life of the test substance, assuming first order kinetics, from the decrease in the concentration of the compound with time. The microsomal clearance (mClint) was calculated as follows: mClint=((ln(2)/t 1/2)/Microsomal Protein Concentration (mg/ml))*1000, leading to the unit of μL/min/mg.

TABLE 1

| # | Ki (5-HT$_6$) [nM] | mClint [μl/min/mg] |
|---|---|---|
| 1 | +++ | ++ |
| 2 | +++ | + |
| 3 | +++ | +++ |
| 4 | +++ | + |
| 5 | +++ | + |
| 6 | ++ | +++ |

TABLE 1-continued

| | Ki (5-HT6) | mClint |
|---|---|---|
| 7 | +++ | + |
| 8 | +++ | ++ |
| 9 | +++ | +++ |
| 10 | +++ | ++ |
| 11 | ++ | |
| 12 | ++ | +++ |
| 13 | +++ | + |
| 14 | ++ | |
| 15 | + | +++ |
| 16 | ++ | ++ |
| 18 | +++ | +++ |
| 19 | ++ | ++ |
| 20 | +++ | ++ |
| 21 | ++ | + |
| 22 | ++ | ++ |
| 23 | +++ | ++ |
| 24 | ++ | + |
| 25 | ++ | |
| 26 | +++ | |
| 27 | +++ | ++ |
| 28 | ++ | ++ |
| 29 | +++ | +++ |
| 30 | +++ | + |
| 31 | ++ | +++ |
| 32 | +++ | ++ |
| 33 | +++ | ++ |
| 34 | +++ | +++ |
| 35 | ++ | |
| 36 | +++ | +++ |
| 37 | ++ | +++ |
| 38 | + | |
| 39 | ++ | + |
| 40 | ++ | |
| 41 | +++ | +++ |
| 42 | +++ | +++ |
| 44 | ++ | +++ |
| 45 | +++ | +++ |
| 46 | +++ | |
| 47 | | +++ |
| 49 | | +++ |
| 50 | | +++ |
| 51 | | ++ |
| 52 | | ++ |
| 53 | | ++ |
| 54 | | +++ |
| 55 | | +++ |
| 56 | | +++ |
| 57 | | +++ |
| 58 | | ++ |

Key:
| | Ki (5-HT6) | mClint |
|---|---|---|
| + | 100-<500 nM | from 60 to <120 µl/min/mg |
| ++ | 10-<100 nM | from 30 to <60 µl/min/mg |
| +++ | <10 nM | <30 µl/min/mg |

5. Blocking the hERG Channel

Cell Culture System

Human embryonic kidney (HEK-293) cells, stably transfected with the hERG channel, were obtained from Dr. C. W. January, Cardiology Division, University of Wisconsin. Cells were maintained at 37° C. (5% $CO_2$ atmosphere) in MEM media, supplemented with 2 mM L-glutamine, 0.1 mM nonessential amino acids, 1 mM sodium pyruvate, 1% penicillin/streptomycin, 10% FBS and 0.2 mg/mL Geneticin. Cells were cryo-preserved in 90% FBS 10% DMSO at a concentration of 10 million cells per mL. For electrophysiological studies, cells were thawed, resuspended in CHO serum free media and immediately added to the instrument on the day of study.

Experimental Solutions

The bath solution contained (in mM): 140 NaCl, 5 KCl, 1 $MgCl_2$, 2 $CaCl_2$, 5 glucose, 20 HEPES, pH=7.4. The internal solution contained (in mM): 125 K-aspartate, 20 KCl, 10 EGTA, 5 MgATP, 1 $MgCl_2$, 5 HEPES, pH=7.3. Stock solution (100 mM) of the tested compounds was prepared fresh. An aliquot of stock solution was added to the bath solution to attain targeted compound concentrations of 10, 30 or 100 µM. The DMSO concentration never exceeded 0.1% in the superfusate.

Electrophysiology Workstation and Experimental Protocol

Currents were recorded using PatchXpress (Molecular Devices), an automated planar patch-clamp system and a 16-well Sealchip positioned directly on top of the headstage. To obtain high resistant seals, cells were added to each chamber and allowed to settle for 10 s. Negative pressure was then applied to promote cell delivery to the patch chip openings on the chamber bottom. After formation of gigaohm seals, negative pressure ramps were applied to obtain intracellular access. Access resistance was initially optimized by additional pressure ramps to assure the intracellular access was adequate for voltage clamp experiments (targeted access resistance <10 MΩ). Whole-cell compensation and series resistance compensation were used at 60%. Experiments using PatchXpress were conducted at room temperature; however, the temperature inside the instrument was slightly elevated at the headstage owing to unavoidable heat generated by the instrument. During a five-minute equilibration period, a two-second depolarizing pulse to +40 mV, followed by a two-second repolarizing pulse to −50 mV was applied once every 15 seconds from a holding potential of −80 mV. Cells were exposed to three ascending concentrations of drug.

The compounds of following examples were tested: 3, 5, 8, 9, 13, 18, 23, 24, 27, 34, 41 and 45. All compounds had values of more than 10 µM.

We claim:

1. A compound of formula (I)

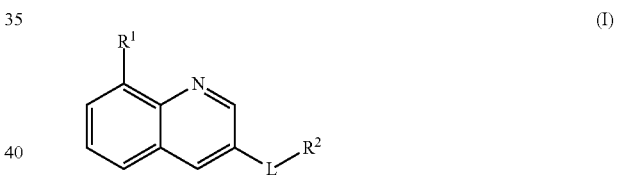

wherein $R^1$ is selected from the group consisting of a ring $R^a$ and halogen;

$R^2$ is a phenyl ring, which may carry one ring $R^a$ and/or one or two substituents $R^5$;

with the proviso that $R^1$ is $R^a$ if the ring $R^2$ is not substituted by $R^a$;

each $R^4$ is independently selected from the group consisting of halogen, $C_1$-$C_6$-alkyl and $C_1$-$C_6$-haloalkyl;

each $R^5$ is independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, aminocarbonyl; and a 3-, 4-, 5-, 6-, 7- or 8-membered saturated heterocyclic ring containing 1, 2 or 3 heteroatoms or heteroatom groups selected from the group consisting of N, O, S, NO, S(O) and $S(O)_2$ as ring members, where the heterocyclic ring may carry one or more substituents $R^7$;

each $R^7$ is independently selected from the group consisting of halogen, $C_1$-$C_6$-alkyl and $C_1$-$C_6$-haloalkyl;

$R^8$ and $R^9$, independently of each other and independently of each occurrence, are hydrogen;

L is $S(O)_2$ $R^a$ is an N-bound saturated 4-, 5-, or 6-membered heteromonocyclic ring containing one nitrogen atom as ring member, where the heteromonocyclic ring carries 1 or 2 substituents $R^b$ and optionally 1 further substituent $R^4$; and $R^b$ is an oxygen-containing radical independently selected from the group consisting of hydroxyl, $C_1$-$C_4$-alkoxy, —C(O)OH, —CH$_2$—C(O)OH and —C(O)N($R^8$)$R^9$;

or an N-oxide, tautomer, or stereoisomer thereof; or a pharmaceutically acceptable salt thereof.

2. The compound as claimed in claim 1, where $R^1$ is $R^a$.

3. The compound as claimed in claim 1, where $R^1$ is halogen; and the phenyl ring $R^2$ carries one substituent $R^a$ and optionally also one or two substituents $R^5$.

4. The compound as claimed in claim 1, where the oxygen-containing radical $R^b$ is selected from the group consisting of hydroxyl (—OH), carboxyl (—C(O)OH), —CH$_2$—C(O)OH and —C(O)NH$_2$.

5. The compound as claimed claim 4, where the oxygen-containing radical $R^b$ is selected from the group consisting of —OH, —C(O)OH and —C(O)NH$_2$.

6. The compound as claimed in claim 1, where
  $R^1$ is $R^a$, where $R^a$ is an N-bound saturated heterocyclic ring selected from the group consisting of azetidin-1-yl, pyrrolidin-1-yl and piperidine-1-yl, where the ring carries one or two substituents $R^b$; and carries optionally one or two substituents $R^4$; and
  $R^2$ is phenyl which may be substituted by 1 or 2 substituents selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, COOH, CONH$_2$ and an N-bound saturated heterocyclic ring selected from the group consisting of azetidin-1-yl, pyrrolidin-1-yl, piperidine-1-yl and piperazin-1-yl, where the heterocyclic ring carries one or two substituents selected from the group consisting of $C_1$-$C_6$-alkyl, $C_1$-$C_6$-haloalkyl, $C_1$-$C_6$-alkoxy, OH and COOH.

7. A compound selected from the group consisting of
1-[3-(3-Trifluoromethyl-benzenesulfonyl)-quinolin-8-yl]-piperidin-4-ol;
1-[3-(3-Trifluoromethyl-benzenesulfonyl)-quinolin-8-yl]-pyrrolidin-3-ol;
1-[3-(3-Trifluoromethyl-benzenesulfonyl)-quinolin-8-yl]-piperidine-4-carboxylic acid;
(S)-1-[3-(3-Trifluoromethyl-benzenesulfonyl)-quinolin-8-yl]-piperidin-3-ol;
(R)-1-[3-(3-Trifluoromethyl-benzenesulfonyl)-quinolin-8-yl]-piperidin-3-ol;
1-[3-(3-Trifluoromethyl-benzenesulfonyl)-quinolin-8-yl]-piperidine-3-carboxylic acid;
4-Methyl-1-[3-[3-(trifluoromethyl)phenyl]sulfonyl-8-quinolyl]piperidin-4-ol;
1-[3-[3-(Trifluoromethyl)phenyl]sulfonyl-8-quinolyl]azetidin-3-ol;
1-[3-(3-Fluorophenyl)sulfonyl-8-quinolyl]piperidin-4-ol;
1-[3-(3-Fluorophenyl)sulfonyl-8-quinolyl]azetidin-3-ol;
(3S)-1-[3-[3-(Trifluoromethyl)phenyl]sulfonyl-8-quinolyl]pyrrolidine-3-carboxylic acid;
(3R)-1-[3-[3-(Trifluoromethyl)phenyl]sulfonyl-8-quinolyl]pyrrolidine-3-carboxylic acid;
1-[3-(3-Methoxyphenyl)sulfonyl-8-quinolyl]piperidin-4-ol;
1-[3-(3-Methoxyphenyl)sulfonyl-8-quinolyl]azetidin-3-ol;
1-[3-(3-Methoxyphenyl)sulfonyl-8-quinolyl]piperidine-4-carboxylic acid;
1-[3-[[8-(4-Hydroxy-1-piperidyl)-3-quinolyl]sulfonyl]phenyl]piperidin-4-ol;
1-[3-[[8-(4-Carboxy-1-piperidyl)-3-quinolyl]sulfonyl]phenyl]piperidine-4-carboxylic acid;
1-[3-(Benzenesulfonyl)-8-quinolyl]piperidin-4-ol;
(3R)-1-[3-[3-(Trifluoromethyl)phenyl]sulfonyl-8-quinolyl]pyrrolidin-3-ol;
(3R)-1-[3-(3-Fluorophenyl)sulfonyl-8-quinolyl]piperidin-3-ol;
1-[3-(2-Methoxyphenyl)sulfonyl-8-quinolyl]piperidin-4-ol;
(3S)-1-[3-(Benzenesulfonyl)-8-quinolyl]piperidin-3-ol;
(3R)-1-[3-(Benzenesulfonyl)-8-quinolyl]piperidin-3-01;
1-[3-[(8-Fluoro-3-quinolyl)sulfonyl]phenyl]piperidin-4-ol;
1-[2-[(8-Fluoro-3-quinolyl)sulfonyl]phenyl]piperidin-4-ol;
(3S)-1-[3-(3-Fluorophenyl)sulfonyl-8-quinolyl]pyrrolidin-3-ol,
(3S)-1-[3-(3-Fluorophenyl)sulfonyl-8-quinolyl]piperidin-3-ol;
1-[3-(2-Hydroxy-5-methyl-phenyl)sulfonyl-8-quinolyl]piperidin-4-ol;
1-[3-[3-(Difluoromethoxy)phenyl]sulfonyl-8-quinolyl]piperidin-4-ol;
(3S)-1-[3-(Benzenesulfonyl)-8-quinolyl]pyrrolidin-3-ol;
1-[3-[3-(Difluoromethoxy)phenyl]sulfonyl-8-quinolyl]piperidine-4-carboxylic acid;
(3 S,4S)-1-[3-(Benzenesulfonyl)-8-quinolyl]pyrrolidine-3,4-diol;
(3R)-1-[3-(3-Fluorophenyl)sulfonyl-8-quinolyl]pyrrolidin-3-ol;
(3R,4R)-1-[3-(Benzenesulfonyl)-8-quinolyl]piperidine-3,4-diol;
1-[3-(2-Methoxy-5-methyl-phenyl)sulfonyl-8-quinolyl]piperidin-4-ol;
(3R,5S)-1-[3-(Benzenesulfonyl)-8-quinolyl]piperidine-3,5-diol;
1-[3-(Benzenesulfonyl)-8-quinolyl]piperidine-4-carboxylic acid;
1-[2-[(8-Fluoro-3-quinolyl)sulfonyl]phenyl]azetidin-3-ol;
1-[3-(2-Methoxyphenyl)sulfonyl-8-quinolyl]azetidin-3-ol;
1-[3-(2-Methoxy-5-methyl-phenyl)sulfonyl-8-quinolyl]azetidin-3-ol;
(3 S,4R)-1-[3-(Benzenesulfonyl)-8-quinolyl]piperidine-3,4-diol;
(3R,4S)-1-[3-(Benzenesulfonyl)-8-quinolyl]pyrrolidine-3,4-diol;
(3R,4S)-1-[3-(Benzenesulfonyl)-8-quinolyl]-3-fluoro-piperidin-4-ol;
1-[3-[3-(Trifluoromethyl)phenyl]sulfonyl-8-quinolyl]azetidine-3-carboxylic acid;
(3R,4R)-1-[3-(Benzenesulfonyl)-8-quinolyl]pyrrolidine-3,4-diol;
1-[3-(3-Trifluoromethyl-benzenesulfonyl)-quinolin-8-yl]-piperidine-3-carboxylic acid amide;
1-[3-(3-Cyanophenyl)sulfonyl-8-quinolyl]piperidine-4-carboxylic acid;
1-[3-(3-Carbamoylphenyl)sulfonyl-8-quinolyl]piperidine-4-carboxylic acid;
1-[3-(3-Carboxyphenyl)sulfonyl-8-quinolyl]piperidine-4-carboxylic acid;
1-[3-(m-Tolylsulfonyl)-8-quinolyl]piperidine-4-carboxylic acid;
1-[3-[3-(Trifluoromethoxy)phenyl]sulfonyl-8-quinolyl]piperidine-4-carboxylic acid;

1-[3-(3-Fluorophenyl)sulfonyl-8-quinolyl]piperidine-4-carboxylic acid;

1-[3-(3-Pyrrolidin-1-ylphenyl)sulfonyl-8-quinolyl]piperidine-4-carboxylic acid;

1-[3-[3-(3-Methoxypyrrolidin-1-yl)phenyl]sulfonyl-8-quinolyl]piperidine-4-carboxylic acid;

1-[3-(3-Piperazin-1-ylphenyl)sulfonyl-8-quinolyl]piperidine-4-carboxylic acid;

1-[3-[3-(4-Methylpiperazin-1-yl)phenyl]sulfonyl-8-quinolyl]piperidine-4-carboxylic acid;

2-[1-[3-[3-(Trifluoromethyl)phenyl]sulfonyl-8-quinolyl]-4-piperidyl]acetic acid; and 2-[1-[3-[3-(Trifluoromethyl)phenyl]sulfonyl-8-quinolyl]-3-piperidyl]acetic acid;

or an N-oxide, tautomer, stereoisomer, or stereoisomeric mixture thereof; or a pharmaceutically acceptable salt thereof.

8. A pharmaceutical composition comprising a therapeutically effective amount of at least one compound as claimed in claim 1 or an N-oxide, a tautomeric form, a stereoisomer or a pharmaceutically acceptable salt thereof, in combination with at least one pharmaceutically acceptable carrier and/or auxiliary substance.

9. The compound as claimed in claim 5, where the oxygen-containing radical $R^b$ is —OH or —C(O)OH.

10. The compound as claimed in claim 6, where the oxygen-containing radical $R^b$ is -OH, -C(O)OH, or -C(O)NH$_2$.

11. The compound as claimed in claim 6, where $R^2$ is phenyl which may be substituted by 1 or 2 substituents selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, and an N-bound saturated heterocyclic ring selected from the group consisting of azetidin-1-yl, pyrrolidin-1-yl and piperidine-1-yl, where the heterocyclic ring carries one or two substituents selected from the group consisting of $C_1$-$C_6$-alkyl, $C_1$-$C_6$-haloalkyl, OH and COOH.

12. The compound as claimed in claim 7, wherein the compound is 1-[3-(3-Trifluoromethyl-benzenesulfonyl)-quinolin-8-yl]-piperidin-4-ol; or an N-oxide, tautomer, stereoisomer, or stereoisomeric mixture therof; or a pharmaceutically accetable sallt thereof.

13. The compound as claimed in claim 7, wherein the compound is 1-[3-(3-Flurophenyl(sulfonyl-8-quinolyl]piperidin-4-ol; or an N-oxide, tautomer, stereoisomer, or stereoisomeric mixture therof; or a pharmaceutically acceptable salt thereof.

14. The compound as claimed in claim 7, wherein the compound is 1-[3-(Benzenesulfonyl)-8-quinolyl]piperidin-4-ol; or an N-oxide, tautomer, stereoisomer, or stereoisomeric mixture thereof; or a pharmaceutically acceptable salt thereof.

15. The compound as claimed in claim 7, wherein the compound is (3R)-1-[3-(Benzenesulfonyl)-8-quinolyl]piperidin-3-ol; or N-oxide, tautomer, stereoisomer, or stereoisomeric mixture thereof; or a pharmaceutically acceptable salt thereof.

16. The compound as claimed in claim 7, wherein the compound is (3R, 4S)-1-[3-(Benzenesulfonyl)-8-quinolyl]pyrrolidine-3, 4-diol; or an N-oxide, tautomer, stereoisomer, or stereoisomeric mixture thereof; or a pharmaceutically acceptable salt thereof.

17. The compound as claimed in claim 7, wherein the compound is (3R, 4R)-1-[3-(Benzenesulfonyl)-8-quinolyl]pyrrolidine-3,4-diol; or an N-oxide, tautomer, stereoisomer, or stereoisomeric mixture thereof; or a pharmaceutically acceptable salt thereof.

* * * * *